(12) United States Patent
Vanotti et al.

(10) Patent No.: US 8,207,180 B2
(45) Date of Patent: Jun. 26, 2012

(54) TRICYCLIC INDOLES AND (4,5-DIHYDRO) INDOLES

(75) Inventors: Ermes Vanotti, Milan (IT); Marina Caldarelli, Milan (IT); Francesco Casuscelli, Milan (IT); Barbara Forte, Milan (IT); Maria Menichincheri, Milan (IT); Alessandra Scolaro, Milan (IT); Gabriella Traquandi, Milan (IT); Paola Vianello, Milan (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 359 days.

(21) Appl. No.: 12/516,712

(22) PCT Filed: Nov. 23, 2007

(86) PCT No.: PCT/EP2007/062762
§ 371 (c)(1),
(2), (4) Date: May 28, 2009

(87) PCT Pub. No.: WO2008/065054
PCT Pub. Date: Jun. 5, 2008

(65) Prior Publication Data
US 2010/0075998 A1   Mar. 25, 2010

(30) Foreign Application Priority Data
Nov. 28, 2006  (EP) .................................. 06124947

(51) Int. Cl.
| A61K 31/517 | (2006.01) |
| A61K 31/519 | (2006.01) |
| A61K 31/505 | (2006.01) |
| A61K 31/4353 | (2006.01) |
| A61K 31/416 | (2006.01) |
| A61K 31/4162 | (2006.01) |
| C07D 487/12 | (2006.01) |
| C07D 471/12 | (2006.01) |

(52) U.S. Cl. ........ 514/267; 514/292; 514/406; 544/250; 546/84; 548/359.5

(58) Field of Classification Search .................. 514/267, 514/292, 406; 544/250; 546/84; 548/359.5
See application file for complete search history.

(56) References Cited

FOREIGN PATENT DOCUMENTS
WO   WO 2006/039718 A2   4/2006

OTHER PUBLICATIONS
Golub et al. Science (1999), vol. 286 531-537.*
Lala et al. Cancer and Metastasis Reviews (1998), 17(1), 91-106.*

* cited by examiner

*Primary Examiner* — Rebecca Anderson
*Assistant Examiner* — Samantha Shterengarts
(74) *Attorney, Agent, or Firm* — Scully, Scott, Murphy & Presser, P.C.

(57) ABSTRACT

The present invention provides tricyclic indoles and (4,5-dihydro) indoles of the formula (I) or a pharmaceutically acceptable salt thereof: wherein the ring A represents a fused pyrazole, pyridine or pyrimidine, ═══means either simple or double carbon-carbon bond and $R_1$, $R_2$ and $R_3$ are as defined in the specification. Further objects of the invention are a process for the preparation of the compounds of the formula (I), pharmaceutical compositions comprising them and methods for treating cell proliferative disorders. As a matter of fact, the compounds of the formula (I) are useful, in therapy, in the treatment of diseases associated with a disregulated protein kinase activity, in particular Cdc7 and AKT kinase activity, like cancer.

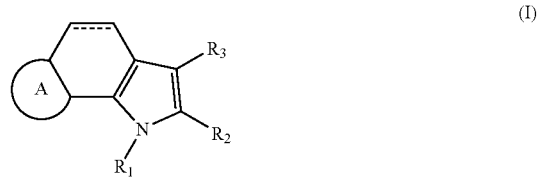

(I)

13 Claims, No Drawings

TRICYCLIC INDOLES AND (4,5-DIHYDRO) INDOLES

The present invention relates to tricyclic indoles and (4,5-dihydro) indoles, a process for their preparation, pharmaceutical compositions comprising them and their use as therapeutic agents, particularly in the treatment of cancer and cell proliferation disorders. These compounds are useful, in therapy, as agents against a host of diseases caused by and/or associated to a disregulated protein kinase activity and, more particularly, Cdc7 or Cdc7/Cdks and AKT activity.

In particular, the present invention provides tricyclic indoles and (4,5-dihydro) indoles that are endowed with protein kinase inhibiting activity, especially Cdc7 or Cdc7/Cdks and AKT inhibiting activity.

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases. For a general reference to PKs malfunctioning or disregulation see, for instance, *Current Opinion in Chemical Biology* 1999, 3, 459-465. Several compounds are known in the art as protein kinase inhibitors. In particular we refer to indoles, for instance the pyrazolyl-indole derivatives disclosed in WO05/005414, the hydroxy-indole derivatives disclosed in WO05/105788 and the indole-carboxamides described in WO01/030774, to quinazolines and isoquinolines, represented by the aminopyrimidine derivatives claimed in US2005148603 and WO05/037843, the thiazolo-, oxazolo- and imidazolo-quinazoline compounds presented in WO05/005438, the beta-carboline compounds and analogues claimed in WO05/009370 and the pyrazoloquinazolines described in WO04/104007. Finally we refer to indazoles, for instance 3-(carbonyl)-1H-indazoles reported in WO04/014922 and the tricyclic pyrazoles claimed in WO03/070706 and WO03/070236. DNA replication is a fundamental process for cell proliferation. Mechanisms that control entry in the S-phase and proper execution of DNA synthesis are often altered in malignant cells and at the same time are attractive targets for the development of antitumoral agents. DNA replication is a two-step process: first, during the initiation reaction, proteins bound to origin DNA are activated by phosphorylation in order to assemble replication forks and, second, during elongation, DNA polymerases, together with accessory factors, synthesize new DNA strands. Cdc7 kinase, a key cell cycle regulator, is an evolutionary conserved serine-threonine kinase, which plays a pivotal role in linking cell cycle regulation to genome duplication. In S-phase Cdc7 allows the firing of DNA replication origins by phosphorylating proteins that are recruited at origin sequences during the previous G1. Cdc7-dependent phosphorylation is therefore essential for converting a dormant pre-replicative complex into two active replication forks (Bell, S. P. and Dutta, A. *Annu. Rev. Biochem.* 2002, 71, 333-374. The Cdc7 kinase, like cyclin-dependent kinases, is activated by the binding of alternative regulatory subunits, Dbf4 and Drf1 (Kumagai, H., Sato, N., Yamada, M., Mahony, D., Seghezzi, W., Lees, E., Arai, K., and Masai, H. *Mol. Cell Biol.* 1999, 19, 5083-5095; Montagnoli, A., Bosotti, R., Villa, F., Rialland, M., Brotherton, D., Mercurio, C, Berthelsen, J., and Santocanale, C. *EMBO J.* 2002, 21, 3171-3181). Cdc7, Dbf4 and Drf1 mRNA are overexpressed in a number of tumor cell lines (Hess, G. F., Drong, R. F., Weiland, K. L., Slightom, J. L., Sclafani, R. A., and Hollingsworth, R. E. *Gene* 1998, 211, 133-140; Kumagai, H., Sato, N., Yamada, M., Mahony, D., Seghezzi, W., Lees, E., Arai, K., and Masai, H. *Mol. Cell Biol.* 1999, 19, 5083-5095; Montagnoli, A., Bosotti, R., Villa, F., Rialland, M., Brotherton, D., Mercurio, C., Berthelsen, J., and Santocanale, C. *EMBO J.* 2002, 21, 3171-3181). Cdc7 kinase is a potential good target for the development of anti-cancer drugs. In fact Cdc7 function is essential for DNA replication and cell proliferation of human cells: microinjection of specific anti-Cdc7 antibodies prevents DNA replication (Jiang, W., McDonald, D., Hope, T. J., and Hunter, T. *EMBO J.* 1999, 18, 5703-5713) and genetic downregulation of Cdc7 kinase by siRNA block DNA synthesis leading to a p53 independent cell death in several cancer cell lines (Montagnoli, A., Tenca, P., Sola, F., Carpani, D., Brotherton, D., Albanese, C., and Santocanale, C. *Cancer Res.* 2004, 64, 7110-7116). Furthermore Cdc7 inhibition abolishes the phosphorylation of relevant cellular substrate (MCM2 protein) at specific phosphorylation sites (Montagnoli, A., Valsasina, B., Brotherton, D., Troiani, S., Rainoldi, S., Tenca, P., Molinari, A., and Santocanale, C. *J Biol. Chem.* 2006, 281, 10281-10290).The present invention relates also to tricyclic (4,5-dihydro) indole compounds useful for treating diseases mediated by AKT. AKT (also known as protein kinase B (PKB) or Rac-PK-beta), and its gene family products, has been identified as a serine/threonine protein kinase (*Proc. Natl. Acad. Sci.* 2001, 98, 10983-10985; *J. Cell. Sci.* 2001, 114, 2903-2910; *Circ. Res.* 2000, 86, 15-23). Three isoforms of PKB are currently known, PKBα (AKT1), PKBβ (AKT2), and PKBγ (AKT3) (*Proc. Natl. Acad. Sci.* 1992, 89, 9267-9271; *J. Biol. Chem.* 1999, 274, 9133-9136). PKB mediates many effects of IGF-1 and other growth factors on tumor growth and inhibition of apoptosis (*Cell. Signal.* 2002, 14, 381-395). PKB plays an important role in cell proliferation, apoptosis and response to insulin. For these reasons, modulation of PKBs is of interest in the treatment of tumor genesis, abnormal cell proliferation and diabetes. The molecular structure of the PKBs comprises a regulatory site near the carboxy terminus of the polypeptide, a catalytic domain with an activation loop having a threonine, and an amino-terminal pleckstrin homology domain. The pleckstrin homology domain permits anchorage of the enzyme to the cell membrane through interaction with phospholipids, which triggers the activation of the PKBs. The role of pleckstrin homology domain requires phosphorylation of phosphatidylinositol at the D-3 position via phosphatidylinositol 3-kinase PI3K, an SH2 domain protein that associates with activated receptor tyrosine kinases, particularly IGF-1R. In particular, phosphoinositol-3-kinase, when activated by receptor tyrosine kinase, catalyzes the synthesis of phosphoinositol-3,4-diphosphate and phosatidylinositol-3,4,5-triphosphate. The pleckstrin homology domain binds 3-phosphoinositides, which are synthesized by PI3K upon stimulation by growth factors such as platelet derived growth factor (PDGF), nerve growth factor (NGF) and insulin-like growth factor (IGF-1) (*Mol. Cell. Biol.* 1997, 17, 1595-1606; *Science* 1997, 275, 628-630; *Genev. Dev.* 1999, 13, 2905-2927). Lipid binding to the pleckstrin homology domain promotes translocation of PKB to the plasma membrane. Further activation of PKB occurs by phosphorylation by another protein kinase, PDK1 at Thr309, and Thr305 for the PKB isoforms 1, 2 and 3, respectively. A third step of activation is catalyzed by a kinase that phosphorylates Ser473, Ser474 or Ser472 in the C-terminal tails of PKB/AKT-1, -2 and -3 respectively. The Ser473 kinase activity has been identified to be associated with plasma membrane and is not due to PKB and PDK1 kinase activity (*Current Biology* 2002, 12, 1251-1255; *J. Biol. Chem.* 2003, 278, 21615-21622). The process produces the fully activated form of PKB.

Activation of PKB can also occur by inhibiting the D-3 phosphoinositide specific phosphatase, PTEN, which is a membrane associated FYVE finger phosphatase commonly inactivated in many cancers, including prostate cancer (*Eur. J. Biochem.* 1999, 263, 605-611; *Cancer Res.* 1997, 57, 2124-2129).

The catalytic domain of PKB is responsible for the phosphorylation of serine or threonine in the target protein.

Once activated, PKB mediates several cellular functions, including proliferation, cell growth, and promotion of survival.

The anti-apoptotic function of PKB is reported to be mediated by its ability to phosphorylate apoptosis regulatory molecules including BAD, caspase 9, IKK-, and the forkhead transcriptional factor FKHRL1. PKB signal is also implicated in the physiological regulation of organ size (*Nat. Cell. Biol.* 1999, 1, 500-506), glucose homeostasis (*J. Biol. Chem.* 1999, 274, 1865-1868), vasomotor tone (*J. Clin. Invest.* 1999, 106, 493-499), and angiogenesis (*Nat. Med.* 2000, 6, 1004-1010).

Manifestations of altered PKB regulation appear in both injury and disease, the most important role being in cancer. PKB kinase activity is constitutively activated in tumors with PTEN mutation, PI3-kinase4 mutation and overexpression, and receptor tyrosin kinase overexpression. PKB is also a mediator of normal cell functions in response to growth factor signalling. Expression of the AKT gene was found to be amplified in 15% of human ovarian carcinoma cases (*Proc. Natl. Acad. Sci.* 1992, 89, 9267-9271). AKT is also overexpressed in 12% of pancreatic cancers (*Proc. Natl. Acad. Sci.* 1996, 93, 3636-3641). In particular, AKT-2 is over-expressed in 12% of ovarian carcinomas and in 50% of undifferentiated tumors, suggesting that PKB may be associated with tumor aggressiveness (*Int. J. Cancer* 1995, 64, 280-285). PKB is also a mediator of normal cell functions (*Nature* 1999, 401, 33-34; *Oncogene* 2000, 19, 2324-2330; *Neurosci.* 2000, 20, 2875-2886).

Elucidation of the role of PKB in the increase of growth and inhibition of apoptosis is complicated by the many protein substrates of PKB, including BAD, Forkhead (FOXO family), GSK3, Tuberin (TSC2), p27 Kip1, p706sk, protein kinase C-, forkhead in rhabdomyosarcoma, Raf, cAMP-responsive element-binding protein, glycogen synthase kinase-3, m-TOR, and the androgen receptor (*Proc. Natl. Acad.* 2001, 98, 7200-7205; *Nature* 2001, 411, 355-365; *Nat. Rev. Cancer* 2002, 2, 489-501).

The various PKBs vary in their abundance in different mammalian cell types. For example, PKBβ are especially abundant in highly insulin-responsive tissues, including brown fat.

Modulation of PKB by small molecules can be achieved by identifying compounds that bind to and activate or inhibiting one or more PKBs.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of PKs in the regulation of cellular proliferation, these tricyclic indoles and (4,5-dihydro) indoles are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

Some pyrrolo(iso)quinoline derivatives are known in the art and were studied as 5-HT2C receptor agonists (see Bioorganic & Medicinal Chemistry Letters (2006), 16(3), 677-680), as cytotoxic agents (European Journal of Pharmaceutical Sciences (2002), 17(3), 139-143), as antiproliferative agents (Farmaco (1991), 46(6), 833-8 and (1989), 44(12), 1141-55). The synthesis of 1H-pyrrolo[2,3-f]isoquinoline and some of its derivatives are described by Ponasenkova, T. F. et al. in Khimiya Geterotsiklicheskikh Soedinenii (1984), (4), 490-4, as for example 1H-Pyrrolo[2,3-f]isoquinoline-2-carboxylic acid, ethyl ester. The present inventors have now discovered that some tricyclic indoles and (4,5-dihydro) indoles, are endowed with multiple protein kinase inhibiting activity and are thus useful in therapy in the treatment of diseases caused by and/or associated with deregulated protein kinases.

In particular, the compounds of the invention can be active as inhibitors of protein kinases such as, for instance, Cdc7, Cdks, AKT, PKA, protein kinase C in different isoforms, Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, VEGF-R, PI3K, wee1 kinase, Src, Abl, ILK, MK-2, IKK-2, Nek, CK2, GSK3, SULU, PKC, PDK, RET, KIT, LCK, TRKA and thus be effective in the treatment of diseases associated with these and other protein kinases.

Accordingly, in a first embodiment, the present invention provides a compound of the formula (I):

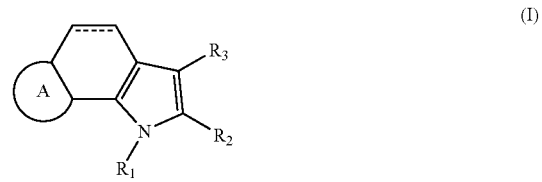

wherein the ring A represents a fused heterocycle of the formula IIa, IIb, III or IV:

-continued

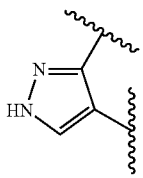
(IIb)

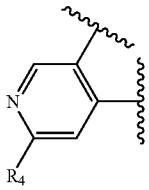
(III)

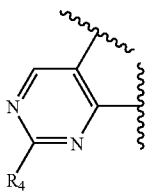
(IV)

R₁ represents hydrogen atom or an optionally substituted group selected from alkyl, cycloalkyl, alkenyl, alkynyl, heterocyclyl, aryl, heterocyclyloxy-alkyl and alkoxycarbonyl group;

R₂ is hydrogen or halogen atom or a group of formula —COOR₅ or —CONHR₅, wherein R₅ represents one of the meanings above defined for R₁, or an optionally substituted aryl or heterocyclyl group;

R₃ is hydrogen atom or a group of formula —CHO, —COOR₅ or —CONHR₅, wherein R₅ is as defined above;

R₄ is hydrogen atom or NHR₆, wherein R₆ is hydrogen atom or an optionally substituted alkyl, aryl or heterocyclyl group;

═══ means either simple or double Carbon-Carbon bond (—CH₂—CH₂— or —CH═CH—);

or a pharmaceutically acceptable salt thereof;

with the provisos that
if R₂ is hydrogen or halogen atom or an optionally substituted aryl or heterocyclyl group, then R₃ is not hydrogen atom, and
if the ring A is a fused heterocycle of the formula III, R₃ and R₄ are hydrogen atoms, and ═══ means double Carbon-Carbon bond (—CH═CH—), then R₂ is not COOH, COOMe or COOEt and
the compound 1H-pyrrolo[2,3-f]isoquinoline-3-carboxaldehyde is excluded.

The compounds of formula (I), object of the invention, are obtainable through a synthetic process comprising well known reactions carried out according to conventional techniques, comprised within the scope of the invention.

The present invention also provides a pharmaceutical composition comprising a compound of formula (I) as defined above and at least one pharmaceutically acceptable excipient, carrier or diluent.

There is also provided a method for treating cell proliferative disorders caused by and/or associated with an altered protein kinase activity which comprises administering to a mammal in need thereof, preferably a human, an effective amount of a compound of formula (I) as above defined. The cell proliferative disorders to be treated are preferably those caused by and/or associated with an altered Cdc7 or AKT kinase.

The method of the present invention can also further comprise subjecting the mammal in need thereof to a radiation therapy or chemotherapy regimen in combination with at least one cytostatic or cytotoxic agent.

The present invention also provides a product or kit comprising a compound of formula (I), a pharmaceutically acceptable salt thereof, or pharmaceutical compositions thereof as above defined, and one or more chemotherapeutic agent, as a combined preparation for simultaneous, separate or sequential use in anticancer therapy.

It is another object of the present invention to provide a compound of formula (I) or a pharmaceutically acceptable salt thereof, as above defined, for use as a medicament, preferably for treating cell proliferative disorders caused by and/or associated with an altered protein kinase activity.

Preferably, a compound of the formula (I) is characterized in that R₂ represents hydrogen or halogen atom or an optionally substituted aryl or heterocyclyl group or a —C(O)NHR₅ group and R₃ represents hydrogen atom or a —CONHR₅ group, wherein R₅ is as defined above.

More preferably, a compound of the formula (I) is characterized in that R₁ represents hydrogen atom or an optionally substituted alkyl; R₂ represents hydrogen atom or an optionally substituted aryl or heterocyclyl group or a —CONHR₅ group, wherein R₅ represents (S)-3-phenyl-propane-1-amino-2-yl group; R₃ represents hydrogen atom or a —CONHR₅ group, wherein R₅ represents hydrogen atom or (S)-3-phenyl-propane-1-amino-2-yl group; R₄ represents hydrogen atom or NH₂.

Specific, not limiting, preferred compounds of formula (I) of the invention, whenever appropriate in the form of pharmaceutically acceptable salts, are the following:

1-methyl-1,6-dihydro-1,6,7-triaza-as-indacene-3-carboxylic acid (B2);

1-methyl-1,7-dihydro-1,6,7-triaza-as-indacene-3-carboxylic acid amide (B3);

2-chloro-1-methyl-1,6-dihydro-1,6,7-triaza-as-indacene-3-carboxylic acid amide (C1);

1-methyl-2-phenyl-1,7-dihydro-1,6,7-triaza-as-indacene-3-carboxylic acid amide (C2);

4,5-dihydro-1H-pyrrolo[2,3-f]isoquinoline-3-carboxylic acid (E6);

1-(2,2,2-trifluoroethyl)-4,5-dihydro-1H-pyrrolo[2,3-f]isoquinoline-3-carboxylic acid (E7);

4,5-dihydro-1H-pyrrolo[2,3-f]isoquinoline-3-carboxylic acid amide (E10);

tert-butyl {(2S)-2-[(4,5-dihydro-1H-pyrrolo[2,3-f]isoquinolin-3-ylcarbonyl)amino]-3-phenylpropyl}carbamate (E11);

tert-butyl [(2S)-3-phenyl-2-({[1-(2,2,2-trifluoroethyl)-4,5-dihydro-1H-pyrrolo[2,3-f]isoquinolin-3-yl]carbonyl}amino)propyl]carbamate (E12);

N-[(1S)-2-amino-1-benzylethyl]-1-(2,2,2-trifluoroethyl)-4,5-dihydro-1H-pyrrolo[2,3-f]isoquinoline-3-carboxamide (E14);

N-[(1S)-2-amino-1-benzylethyl]-4,5-dihydro-1H-pyrrolo[2,3-f]isoquinoline-3-carboxamide (E15);

N-[(1S)-2-amino-1-benzylethyl]-1-(2-hydroxyethyl)-4,5-dihydro-1H-pyrrolo[2,3-f]isoquinoline-3-carboxamide (E21);

2-bromo-4,5-dihydro-1H-pyrrolo[2,3-f]isoquinoline-3-carboxylic acid ethyl ester (F1);

1-methyl-2-o-tolyl-4,5-dihydro-1H-pyrrolo[2,3-f]isoquinoline-3-carboxylic acid amide (F5);

2-phenyl-1H-pyrrolo[2,3-f]isoquinoline-3-carboxylic acid amide (G3);

2-(4-bromo-phenyl)-1H-pyrrolo[2,3-f]isoquinoline-3-carboxylic acid (G5);
2-(4-bromo-phenyl)-1H-pyrrolo[2,3-f]isoquinoline-3-carboxylic acid amide (G6);
2-(4-morpholin-4-yl-phenyl)-1H-pyrrolo[2,3-f]isoquinoline-3-carbaldehyde (G7);
2-phenyl-1H-pyrrolo[2,3-f]isoquinoline-3-carboxylic acid ((S)-2-amino-1-benzyl-ethyl)-amide (G9);
2-pyridin-4-yl-1H-pyrrolo[2,3-f]isoquinoline-3-carbaldehyde (H1);
2-pyridin-4-yl-1H-pyrrolo[2,3-f]isoquinoline-3-carboxylic acid amide (H3);
4,5-dihydro-1H-pyrrolo[2,3-f]isoquinoline-2-carboxylic acid (L2);
N-[(1S)-2-amino-1-benzylethyl]-4,5-dihydro-1H-pyrrolo[2,3-f]isoquinoline-2-carboxamide (L6);
N-[(1S)-2-amino-1-benzylethyl]-1-(2,2,2-trifluoroethyl)-4,5-dihydro-1H-pyrrolo[2,3f]isoquinoline-2-carboxamide (L9);
8-amino-1-methyl-2-phenyl-4,5-dihydro-1H-1,7,9-triaza-cyclopenta[a]naphthalene-3-carboxylic acid amide (N4);
8-amino-2-phenyl-1H-1,7,9-triaza-cyclopenta[a]naphthalene-3-carboxylic acid amide (N9) and
8-amino-1-methyl-2-phenyl-1H-1,7,9-triaza-cyclopenta[a]naphthalene-3-carboxylic acid amide (N10).

AS stated above, a method of treating cell proliferative disorders caused by and/or associated with an altered kinase activity by administering to a mammal in need thereof an effective amount of a compound of formula I as defined above is also provided.

In a preferred embodiment of the method described above, the cell proliferative disorder is cancer.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer, and Kaposi's sarcoma.

In the present description, unless otherwise specified, the following terms have the following meanings.

Aryl, cycloalkyl and heterocyclyl groups sometimes will be collectively defined as "cyclyl" for convenience.

The term "alkyl" or "Alk" refers to straight or branched monovalent saturated aliphatic hydrocarbyl groups having from 1 to 6 carbon atoms. This term is exemplified by groups such as methyl, ethyl, n-propyl, iso-propyl, n-butyl, isobutyl, sec-butyl, t-butyl, n-pentyl, n-hexyl, and the like. "Substituted alkyl" refers to an alkyl group having from 1 to 3 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogens, hydroxyl, nitro, carboxyl, carboxyl esters, cycloalkyl, substituted cycloalkyl, heterocyclyl, and substituted heterocyclyl.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclohexyl, cyclooctyl and the like.

"Substituted cycloalkyl" refers to a cycloalkyl, having from 1 to 5 substituents selected from the group consisting of oxo (=O), thioxo (=S), alkyl substituted alkyl alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heterocyclyl, and substituted heterocyclyl.

"Alkenyl" refers to alkenyl groups having from 2 to 6 carbon atoms. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heterocyclyl, and substituted heterocyclyl with the proviso that any hydroxyl substitution is not attached to a vinyl (unsaturated) carbon atom.

"Alkynyl" refers to alkynyl groups having from 2 to 6 carbon atoms. "Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heterocyclyl, and substituted heterocyclyl with the proviso that any hydroxyl substitution is not attached to an acetylene (unsaturated) carbon atom.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like. "Substituted alkoxy" refers to the group "substituted alkyl-O—".

"Acyl" refers to the groups H—C(O)—, alkyl-C(O)—, substituted alkyl-C(O)—, cycloalkyl-C(O)—, substituted cycloalkyl-C(O)—, aryl-C(O)—, substituted aryl-C(O)—, heterocyclyl-C(O)— and substituted heterocyclyl-C(O)—, wherein alkyl, substituted alkyl, cycloalkyl, substituted cycloalkyl, aryl, substituted aryl, heterocyclyl and substituted heterocyclyl are as defined herein.

"Acylamino" refers to the group —C(O)NR'R' where each R' is independently selected from the group consisting of hydrogen, alkyl, substituted alkyl, substituted aryl, cycloalkyl, substituted cycloalkyl, heteroaryl, substituted heteroaryl, heterocyclyl, substituted heterocyclyl and where each R' can be joined to form together with the nitrogen atom a heterocyclyl or substituted heterocyclyl ring and wherein alkyl, substituted alkyl, cycloalkyl, substituted cycloalkyl, aryl, substituted aryl, heterocyclyl and substituted heterocyclyl are as defined herein;

"Acyloxy" refers to the groups alkyl-C(O)O—, substituted alkyl-C(O)O—, aryl-C(O)O—, substituted aryl-C(O)O—, cycloalkyl-C(O)O—, substituted cycloalkyl-C(O)O—, heterocyclyl-C(O)O—, and substituted heterocyclyl-C(O)O— wherein alkyl, substituted alkyl, cycloalkyl, substituted cycloalkyl, aryl, substituted aryl, heterocyclyl and substituted heterocyclyl are as defined herein.

"Substituted amino" refers to the group —NR'R' wherein R' are as defined above provided that both R' are not hydrogen. When R' is hydrogen and the other R' is alkyl, the substituted amino group is sometimes referred to herein as alkylamino. When both of R' are alkyl, the substituted amino group is sometimes referred to herein as dialkylamino. When referring to a monosubstituted amino, it is meant that either R' is hydrogen but not both. When referring to a disubstituted amino, it is meant that neither R' is hydrogen.

"Aminoacyl" refers to the groups —NR'C(O)alkyl, —NR'C(O) substituted alkyl, —NR'C(O)cycloalkyl, —NR'C(O) substituted cycloalkyl, —NR'C(O)aryl, —NR'C(O) substituted aryl, —NR'C(O)heterocyclyl, and —NR'C(O) substituted heterocyclyl where R' is as defined above.

"Carboxyl" refers to —COOH or salts thereof.

"Carboxyl ester" or simply "ester" refer to the groups —C(O)O-alkyl, —C(O)O— substituted alkyl, —C(O)O— aryl, and —C(O)O— substituted aryl wherein alkyl, substituted alkyl, aryl and substituted aryl are as deemed herein.

"Halo" or "halogen" or "X" refer to fluoro, chloro, bromo and iodo and preferably is fluoro, chloro or bromo.

"Aryl" or "Ar" refer to a monovalent aromatic carbocyclic group of from 6 to 14 carbon atoms having a single ring (e.g. phenyl) or multiple condensed rings (e.g. naphthyl or anthryl) which condensed rings may or may not be aromatic (e.g. 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, selected from the group consisting of hydroxy, acyl, acylamino, acyloxy, alkyl, substituted alkyl, alkoxy, substituted alkoxy, amino, substituted amino, aminoacyl, aryl, substituted aryl, aryloxy, substituted aryloxy, carboxyl, carboxyl esters, cyano, cycloalkyl, substituted cycloalkyl, halo, nitro, heterocyclyl, substituted heterocyclyl, heterocyclyloxy, substituted heterocyclyloxy, amino sulfonyl ($NH_2$—$SO_2$—), and substituted aminosulfonyl.

"Aryloxy" refers to the group aryl-O— that includes, by way of example, phenoxy, naphthoxy, and the like.

"Substituted aryloxy" refers to substituted aryl-O— groups.

"Heterocyclyl" or "heterocyclic" or "heterocycloalkyl" refer to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the heterocyclic ring. "Substituted heterocyclyl" or "substituted heterocycloalkyl" refers to heterocyclyl groups that are substituted with from 1 to 3 of the same substituents as defined for substituted cycloalkyl.

Examples of heterocyclyls include, but are not limited to, pyridinyl, pyrrolyl, indolyl, thienyl, furyl, benzothienyl, benzofuranyl, imidazolyl, benzoimidazolyl, pyrazolyl, thiazolyl, benzothiazolyl, isothiazolyl, oxazolyl, isoxazolyl, pyrazinyl, pyrimidinyl, pyridazinyl, isoindolyl, purinyl, quinolyl, isoquinolyl, dihydroquinolinyl, 2,3-dihydro-1H-indolyl, quinoxalinyl, benzodioxolyl, indanyl, indenyl, triazolyl, azetidinyl, indolizinyl, dihydroindolyl, indazolyl, quinolizinyl, phthalazinyl, naphthylpyridinyl, quinazolinyl, cinnolinyl, pteridinyl, carbazolyl, carbolinyl, phenanthridinyl, acridinyl, phenanthrolinyl, phenazinyl, phenoxazinyl, phenothiazinyl, imidazolidinyl, imidazolinyl, piperidinyl, piperazinyl, indolinyl, phthalimidyl, 1,2,3,4-tetrahydro-isoquinolinyl, 4,5,6,7-tetrahydrobenzo[b]thiophenyl, thiazolidinyl, morpholinyl, thiomorpholinyl (also referred to as thiamorpholinyl), piperidinyl, pyrrolidinyl, pyrrolinyl, pyrazolinyl, pyrazolidinyl and tetrahydrofuranyl.

It should be noted that when referring to heterocyclyl and substituted heterocyclyl, any nitrogen or sulfur atoms that might be present may optionally be oxidized.

From all of the above, it is clear to the skilled man that any of the groups or substituents being defined, for instance, as haloalkyl, alkoxy, alkoxycarbonyl, aryloxy, heteroaryloxy, aminoalkyl, alkylamino, alkylaminoalkyl, dialkylaminoalkyl, and the like, have to be construed from the names of the groups from which they originate.

In this respect, as an example, any group which is identified as an arylalkyl has to be intended as an alkyl group which is further substituted by aryl, wherein both aryl and alkyl are as above defined.

The compounds of formula (I) of the invention may have asymmetric carbon atoms and may therefore exist as individual optical isomers, as racemic admixtures or as any other admixture including a majority of one of the two optical isomers, which are all to be intended as comprised within the scope of the present invention.

In cases when compounds may exist in tautomeric forms, for instance keto-enol tautomers, each tautomeric form is contemplated as being included within this invention whether existing in equilibrium or predominantly in one form.

Likewise, the use as an antitumor agent of all the possible isomers and their admixtures and of both the metabolites and the pharmaceutically acceptable bio-precursors (otherwise referred to as pharmaceutically acceptable pro-drugs) of the compounds of formula (I) are also within the scope of the present invention.

As used herein, the term "pharmaceutically acceptable salts" refers to the nontoxic acid or alkaline earth metal salts of the compounds of formula I. These salts can be prepared in situ during the final isolation and purification of the compounds of formula I, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, malonate, methanesulfonate, nicotinate, 2-napthalenesulfonate, oxalate, palmoate, pectinate, persulfate, 3-phenylpropionate, picrate, pivalate, propionate, succinate, sulfate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides, dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid, nitric acid, hydrobromic acid, perchloric acid and phosphoric acid and such organic acids as oxalic acid, maleic acid, methanesulfonic acid, succinic acid and citric acid, acetic acid, trifluoroacetic acid, propionic acid, glycolic acid, lactic acid, malonic acid, malic acid, tartaric acid, benzoic acid, cinnamic acid, mandelic acid, isethionic acid and salicylic acid.

Basic addition salts can be prepared in situ during the final isolation and purification of the compounds of formula I, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The terms "pharmaceutically acceptable prodrug" and "pharmaceutically acceptable bio-precursors" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the active parent drug, according to formula (I), in vivo, for example by hydrolysis in blood. A discussion is provided in T. Higuchi and V. Stella, Pro-drugs as Novel Delivery Systems, Vol. 14 of the A.C.S. Symposium Series, and in Edward B. Roche, ea., Bioreversible Carriers in Drug Design, American Pharmaceutical Association and Pergamon Press, 1987, both of which are incorporated herein by reference.

As formerly indicated, it is a further object of the invention a process for preparing the compounds of the formula (I) as above defined and pharmaceutically acceptable salts thereof, which process comprises starting from readily available starting materials, using general known methods and procedures, if necessary conventionally protecting and then deprotecting certain functional groups for preventing undesired reactions, and optionally converting an obtained compound of the formula I into another different compound of formula I and/or into pharmaceutically acceptable salts thereof by well known reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

It will be appreciated that, where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures.

In more detail, the present invention provides a first process for preparing a compound of formula I wherein A represents a fused heterocycle of the formula IIa or IIb as defined above and $R_1$ is not hydrogen atom, which process comprises:

treating a compound of formula VI

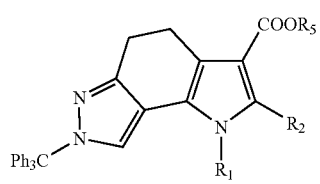

(VI)

wherein $R_5$ is an alkyl group, $R_2$ is a —COOR'$_5$ group wherein R'$_5$ is a labile carboxy-protecting group, and $R_1$ is as defined above, with an acid in a solvent;

optionally N-protecting any of the two nitrogen atoms of the pyrazole ring of the resultant compound of formula I so as to obtain a protected derivative of formula VII:

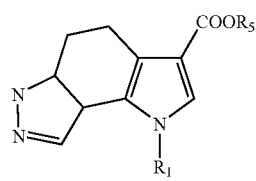

(I)

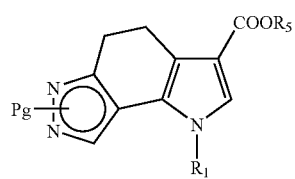

(VII)

wherein Pg is a N-protecting group and $R_1$ and $R_5$ are as defined above;

oxidizing a compound of formula I or the protected compound of the formula VII as defined above;

hydrolyzing the resultant compound of the formula VIII or I:

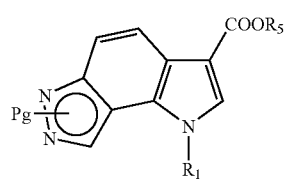

(VIII)

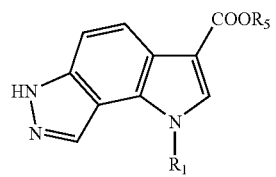

(I)

wherein Pg, $R_1$ and $R_5$ are as defined above, with a base; reacting the resultant compound of the formula IX or I

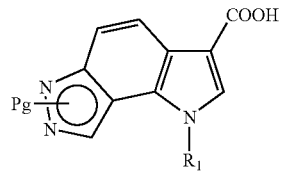

(IX)

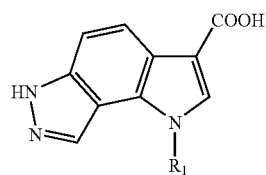

(I)

wherein Pg and $R_1$ are as defined above, with an amine compound of the formula $R_5$—$NH_2$, wherein $R_5$ is hydrogen or alkyl group;

removing the N-protecting group from the resultant compound of the formula X:

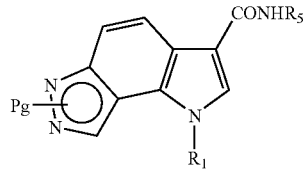

(X)

wherein Pg, $R_1$ and $R_5$ is as defined above, so as to obtain a compound of the formula I wherein A represents a fused heterocycle of the formula IIa or IIb as defined above, $R_1$ is as defined before, $R_2$ is hydrogen atom and $R_3$ is a $CONHR_5$ group wherein $R_5$ is as defined above;

or, alternatively, oxidizing a compound of formula VI as defined above and removing the carboxy-protecting ester group which $R_2$ represents from the resultant compound of the formula I:

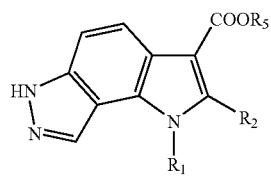

(I)

wherein $R_1$, $R_2$ are as defined above and $R_5$ is an alkyl group, so as to obtain a compound of the formula I wherein A represents a fused heterocycle of the formula IIa or IIb as defined above, $R_1$ is as defined before, $R_2$ is COOH and $R_3$ is $COOR_5$ wherein $R_5$ is as defined above; and optionally converting a resultant compound of formula I into another different compound of formula I and/or into pharmaceutically acceptable salts thereof.

Scheme 1 below shows an example of the preparation of the starting compounds of the formula VI:

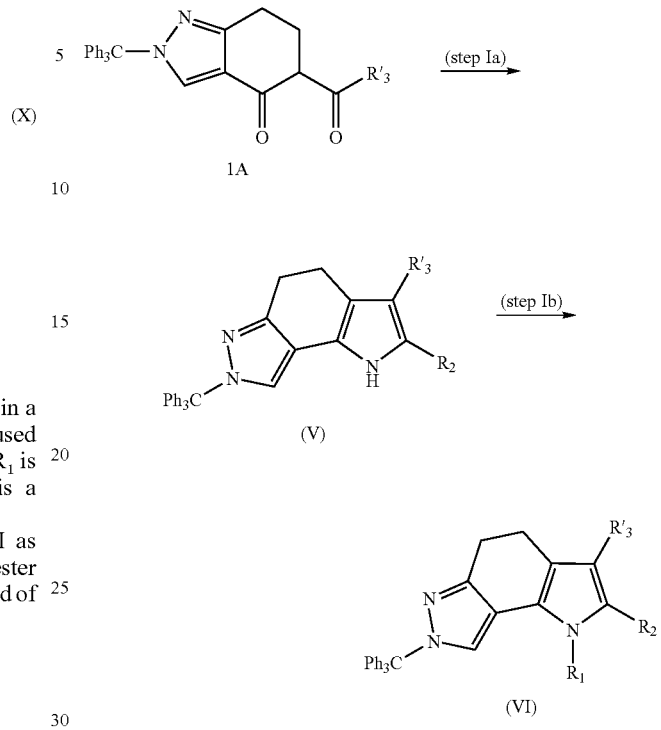

Oxo-(4-oxo-4,5,6,7-tetrahydro-2H-indazol-5-yl)-acetic acid ethyl ester of formula 1A is prepared from 1,3-cyclohexanedione as described by D'Alessio et al. in WO2003070236. The pyrazoloindole nucleus of V originates from a rhodium complex catalyzed cyclocondensation between tert-butylisocyanoacetate and compound 1A (step Ia), as described by Takaya et al. *Organic Letters* 2001, 3, 421. The reaction is run in an aromatic solvent like toluene heating at about 80° C. for 2-5 hours. N-alkylation of pyrrole (step Ib) is performed by treating V with the convenient alkylating agent, most often an alkyl halide in the presence of a base, for instance an alkaline carbonate like caesium carbonate, in aprotic solvents like DMF and heating at about 70° C. for a few hours. This recurring protocol will be hereafter called "the standard method".

Scheme 2 below shows an example of the process described above, wherein the $R'_5$ is tert-butyl group for preparing the ester compounds of the formula I, VII and VIII and Pg is a benzyl group:

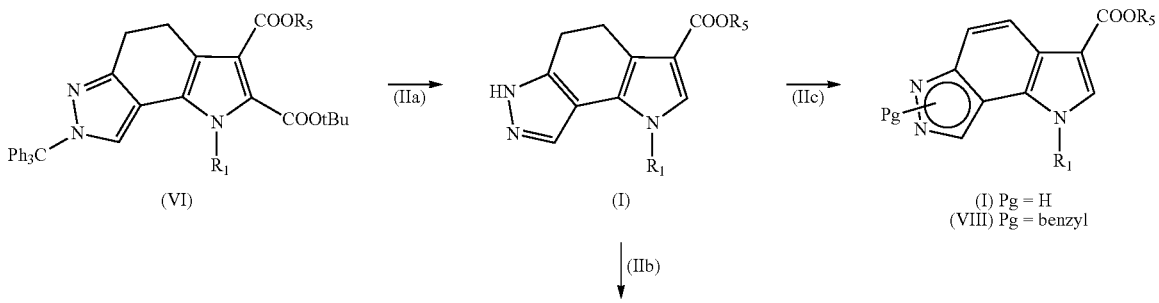

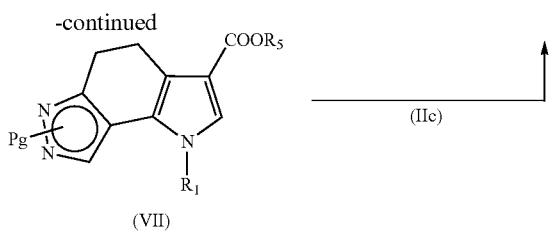

The diester VI is contemporarily deprotected and decarboxylated (step IIa) by heating at reflux in acidic medium, for instance in the presence of 2N hydrochloric acid in ethanol, so providing ester I that can be either directly oxidized to the fully aromatic ester I by means of dichlorodicyanoquinone in refluxing dioxane (step IIc) or can be protected (step IIb) as the benzylated compound VII with the standard method and aromatized to VIII (step IIc).

Scheme 3 below shows an example of the process described above wherein Pg is a benzyl group, for preparing the carboxy and carboxamido compounds of the formula I:

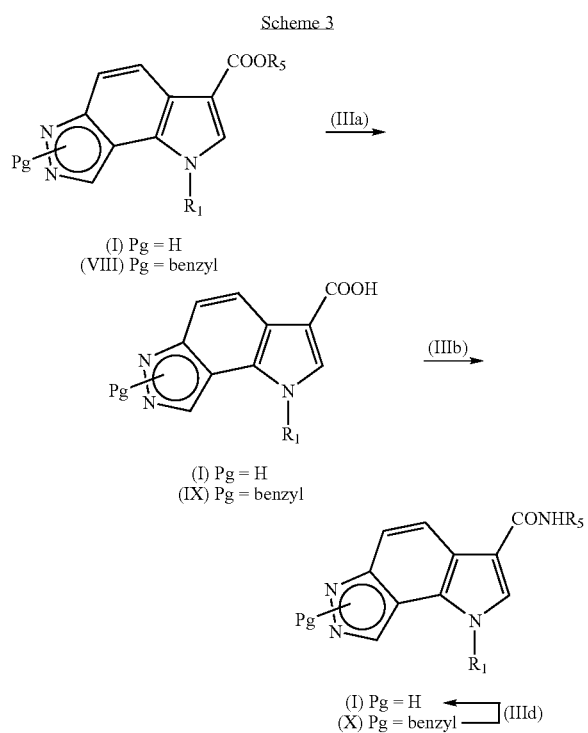

Ester saponification of I or VIII (step IIIa) in basic conditions delivers acids I or IX that can be amidated (step IIIb) by many protocols, for instance with hydroxybenzotriazole-ammonia complex and O-benzotriazol-1-yl-N,N,N',N'-tetramethyluronium tetrafluoroborate in N,N-dimethylformamide at room temperature. This reaction, here employed for the preparation of primary amides, is nevertheless amenable to a variety of amines to form secondary amides, where $R_5$ is not hydrogen. Finally derivative X can be deprotected (step IIId) to I by oxidative removal of the benzyl group in basic conditions, as described by Haddach et al. *Tetr. Lett.* 2002, 43, 399.

An example of the alternative process described above is shown in Scheme 4, in which the compound of formula VI is directly oxidized (step IVc) with the protocol already seen in Scheme 2 and the so obtained diester compound I is selectively hydrolyzed at position 2 using trifluoroacetic acid in dichloromethane at room temperature (step IVd).

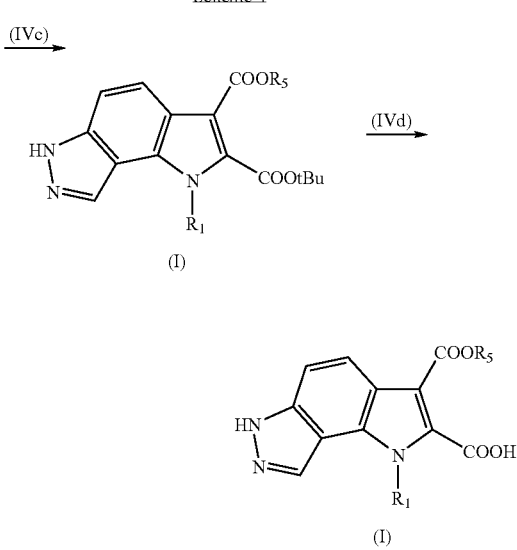

According to the general process above described, the compounds of formula I, wherein A is (IIa) or (IIb), $R_1$ is alkyl, $R_2$ is H or a —$COOR_5$ group and $R_3$ is a —$COOR_5$ or $CONHR_5$ group wherein $R_5$ is as defined above, can be obtained.

Preferably, the compounds that can be prepared according to the processes above described are:

A1: 1-methyl-1,4,5,6-tetrahydro-1,6,7-triaza-as-indacene-3-carboxylic acid ethyl ester;

B1: 1-methyl-1,6-dihydro-1,6,7-triaza-as-indacene-3-carboxylic acid ethyl ester;

B2: 1-methyl-1,6-dihydro-1,6,7-triaza-as-indacene-3-carboxylic acid;

B3: 1-methyl-1,7-dihydro-1,6,7-triaza-as-indacene-3-carboxylic acid amide;

C3: 1-methyl-1,6-dihydro-1,6,7-triaza-as-indacene-2,3-dicarboxylic acid 2-tert-butyl ester 3-ethyl ester;

and C4: 1-methyl-1,6-dihydro-1,6,7-triaza-as-indacene-2,3-dicarboxylic acid 3-ethyl ester.

In more detail, the present invention provides a second process for preparing a compound of formula I wherein A represents a fused heterocycle of the formula IIa or IIb as defined above and $R_1$ is an alkyl group, which process comprises:

alkylating the compound of formula XI on the pyrrole ring:

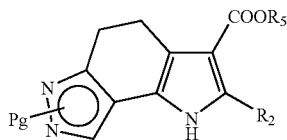 (XI)

wherein Pg is as defined above, $R_2$ is halogen, preferably chloro or bromo, and $R_5$ is an alkyl group, with the standard method;

oxidizing the resultant compound of the formula XII,

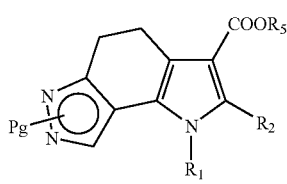 (XII)

wherein $R_1$ is an alkyl group and Pg, $R_2$ and $R_5$ are as defined above;

hydrolyzing the resultant compound of formula XIII:

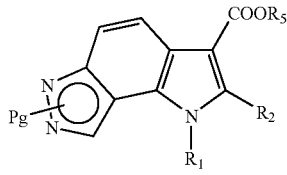 (XIII)

wherein $R_1$, Pg, $R_2$ and $R_5$ are as defined above;

reacting the resultant acid compound of the formula XIV:

(XIV)

wherein $R_1$, Pg and $R_2$ are as defined above, with an amine compound of the formula $R_5$—$NH_2$, wherein $R_5$ is hydrogen or alkyl group;

and optionally (hetero)arylating the resultant compound of the formula XV:

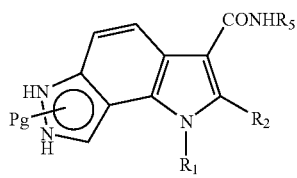 (XV)

$R_2$ = Halogen (XVI)

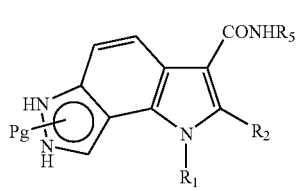

$R_2$ = Aryl or Heteroaryl wherein Pg, $R_1$ and $R_5$ are as defined above, and $R_2$ is halogen atom or aryl or heteroaryl group;

removing the N-protecting group from the compounds of the formula XV or XVI as defined so as to obtain a compound of the formula I wherein A represents a fused heterocycle of the formula IIa or IIb as defined above, $R_1$ is as defined before, $R_2$ is halogen and $R_2$ is or aryl or heteroaryl group and $R_3$ is CONHR$_5$ wherein $R_5$ is as defined above; and optionally converting a resultant compound of formula I into another different compound of formula I and/or into pharmaceutically acceptable salts thereof.

Scheme 5 below shows an example of the preparation of the starting compounds of the formula XI:

Scheme 5

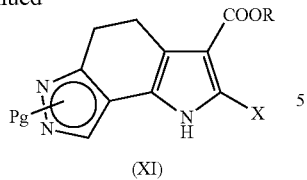

(XI)

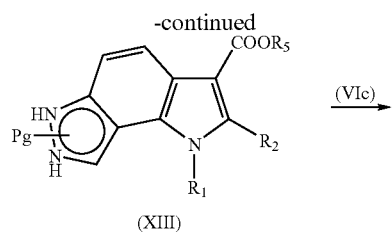

(XIII)

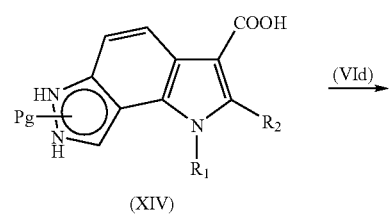

(XIV)

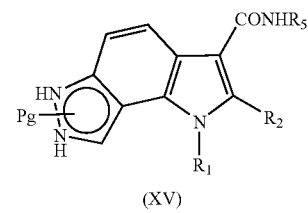

(XV)

Tetrahydro-indazol-4-one 2A is prepared from 1,3-cyclohexanedione as described by D'Alessio et al. in WO2003070236. Bromination of 2A with bromine in acetic acid (step Va), yields bromo-tetrahydro-indazol-4-one 2B that is supplied with a protecting group, for instance a benzyl group (step Vb), to provide 2C. Cyanoester 2D is obtained by replacing bromo with ethylcyanoacetate (step Vc), using a method similar to that described by Murineddu et al. *Chem. Pharm. Bull.* 2002, 50, 754, based on the use of a cyanoacetate in the presence of potassium carbonate in N,N-dimethylformamide. The subsequent cyclization and pyrrole ring formation of compound XI (step Vd) is obtained by a Pinner-like cyclization in acidic medium (with either hydrochloric or hydrobromic acid), a protocol published by Foley et al. *Tetr. Lett.* 1994, 35, 5989.

Scheme 6 below shows an example of the process above described for preparing the critical intermediate compounds of the formula XV:

Scheme 6

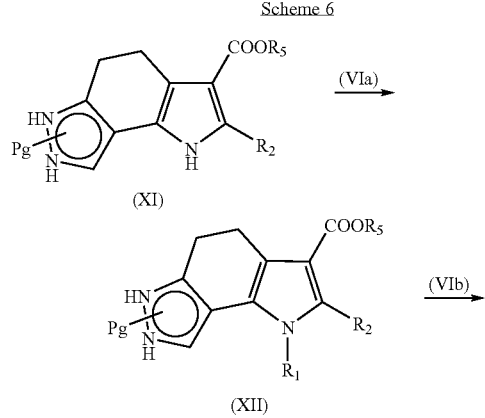

N-alkylation of pyrrole of compound XI (step VIa) is achieved with the standard method, and the oxidation (step VIb) of the obtained compound XII to XIII is obtained by treating with DDQ in dioxane at reflux. Ester saponification (step VIc) in basic conditions delivers acids XIV that can be amidated (step VId) to XV by many protocols, for instance with hydroxybenzotriazole-ammonia complex and O-benzotriazol-1-yl-N,N,N',N'-tetramethyluronium in N,N-dimethylformamide at room temperature. This reaction, here employed for the preparation of primary amides, is nevertheless amenable to a variety of amines to form secondary amides, where $R_5$ is not hydrogen.

Scheme 7 below shows an example of the process above described for preparing the final compounds of the formula I:

Scheme 7

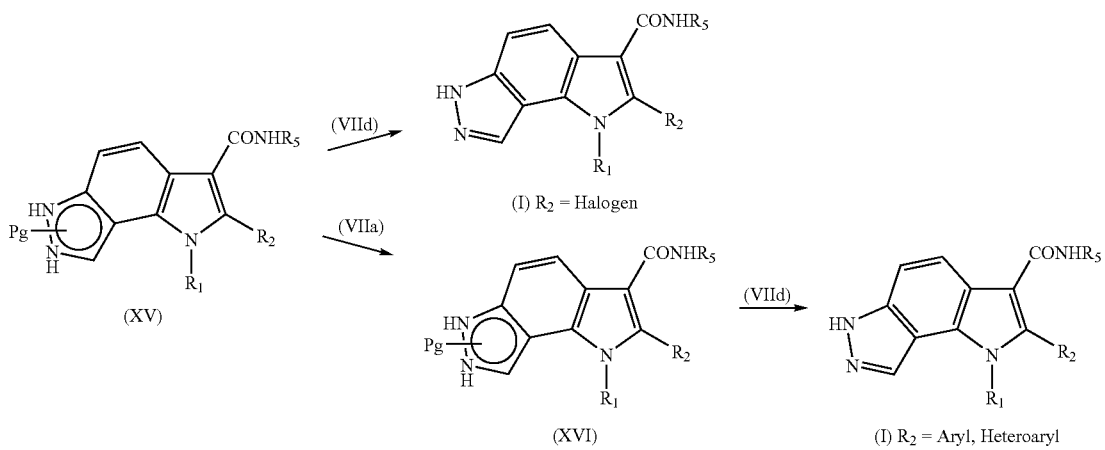

Removal of the benzyl protecting group (step VIId) to yield amide I is performed in basic oxidative conditions with potassium terbutoxide in dimethylsulfoxide.

Access to the 2-aryl or heteroaryl series, represented by compound XVI, is ensured by the biaryl link formation achieved by treating halide XV with a boronic acid derivative in the presence of palladium as the catalyst and sodium carbonate as the base (step VIIa), according to the Suzuki coupling protocols that are well known in the art. The reaction is amenable to a variety of substituted aryl or heteroaryl boronic acids. The sequence is completed by benzyl group removal in order to obtain I (step VIId).

According to the general process above described, the compounds of formula I, wherein A is (IIa) or (IIb), Y is a double bond, $R_1$ is alkyl, $R_2$ is halogen or an (hetero)aryl group and $R_3$ is $CONHR_5$, can be obtained.

Preferably, the compounds that can be prepared according to this method are:

C1: 2-chloro-1-methyl-1,6-dihydro-1,6,7-triaza-as-indacene-3-carboxylic acid amide;

and C2: 1-methyl-2-phenyl-1,7-dihydro-1,6,7-triaza-as-indacene-3-carboxylic acid amide.

In more detail, the present invention provides a third process for preparing a compound of formula I wherein A represents a fused heterocycle of the formula IIa or IIb as defined above and $R_1$ is not hydrogen atom, which process comprises:

alkylating the compound of the formula XVII:

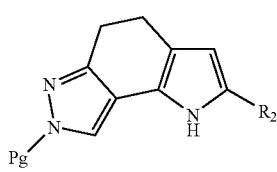

(XVII)

wherein Pg is as defined above and $R_2$ is a —$COOR'_5$ group wherein $R'_5$ is as defined above;

deprotecting the resultant compound of the formula XVIII:

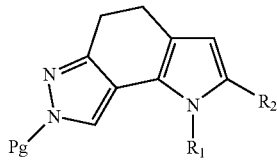

(XVIII)

wherein $R_1$ is alkyl and Pg and $R_2$ are as defined above;

oxidizing the resultant compound I:

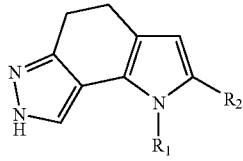

(I)

wherein $R_1$, Pg and $R_2$ are as defined above;

hydrolyzing the resultant compound of the formula I:

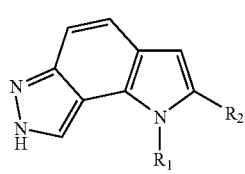

(I)

wherein $R_1$ and $R_2$ are as defined above, with a base;

reacting the resultant compound of the formula I:

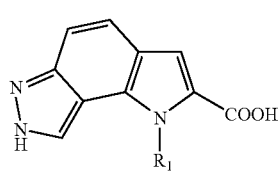

(I)

wherein $R_1$ is as defined above, with an amine compound of the formula $R_5$—$NH_2$, wherein $R_5$ is hydrogen or alkyl group; so as to obtain a compound of the formula I wherein A represents a fused heterocycle of the formula IIa or IIb as defined above, $R_1$ is as defined before, $R_2$ is $CONHR_5$ wherein $R_5$ is as defined above; and optionally converting a resultant compound of formula I into another different compound of formula I and/or into pharmaceutically acceptable salts thereof.

Scheme 8 below shows an example of the preparation of the starting compounds of the formula XVII:

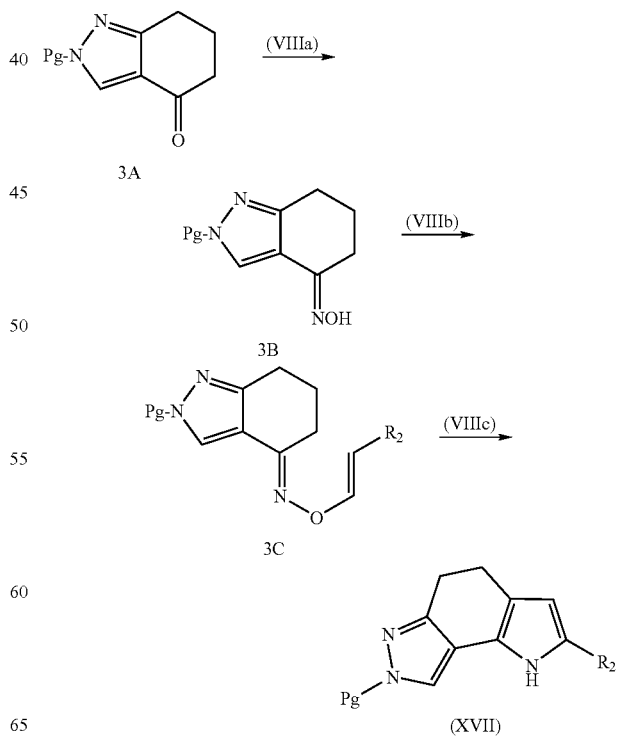

Oxime formation is brought about (step VIIIa) on the protected, for example as the trityl derivative, tetrahydro-indazol-4-one 3A that can be prepared from 1,3-cyclohexanedione as described by D'Alessio et al. in WO2003070236. Oxime 3B is reacted with methylpropiolate (step VIIIb) in dimethylsulfoxide at room temperature, and the resulting O-vinyloxime 3C undergoes rearrangement and cyclization when heated neat at about 150° C. (step VIIIc), thus originating scaffold XVII, in conditions similar to those described by Pinna et al. *Journal of Chemical Research, Synopses* 1990, 11, 360.

Scheme 9 below shows an example of the process described above for preparing the final compounds of the formula I:

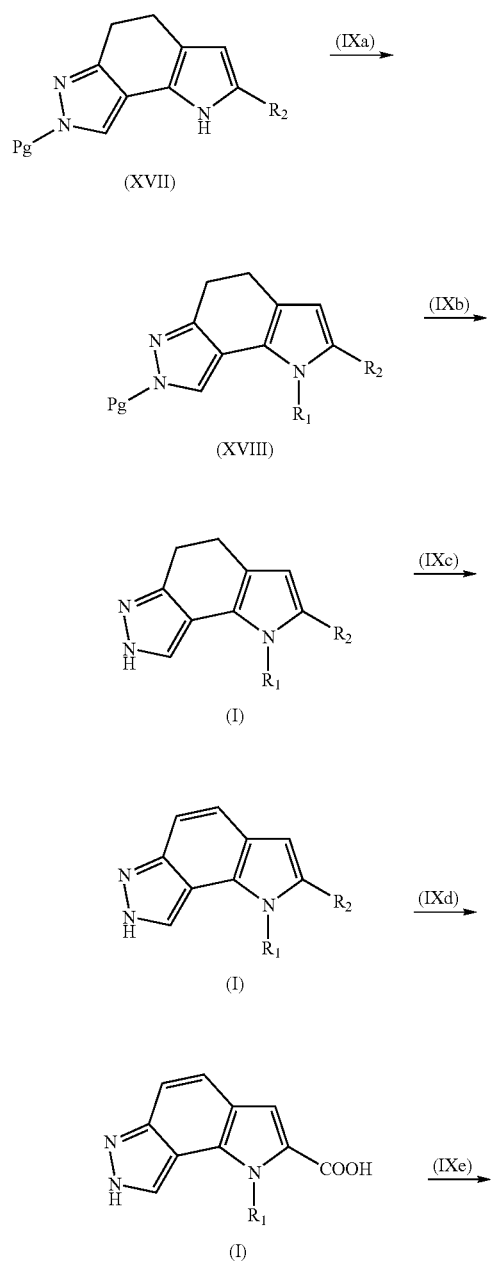

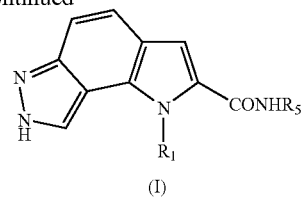

N-methylation at pyrrole of compound XVII (step IXa) occurs by treating with methyl iodide and sodium hydride at room temperature, a reaction that is amenable to a variety of different halides. Standard removal of the trityl group of compound XVIII in acidic medium (step IXb), leads to I that is oxidized (step IXc), by means of dichlorodicyanoquinone in dioxane at reflux. Ester hydrolysis (step IXd) is performed with standard basic hydrolysis with sodium hydroxide in methanol at reflux, while amidation (step IXe) is accomplished with concentrated aqueous ammonia after activation of the acid, for instance with O-benzotriazol-1-yl-N,N,N',N'-tetramethyluronium tetrafluoroborate in acetonitrile. This reaction, here employed for the preparation of primary amides, is nevertheless amenable to a variety of amines to form secondary amides, where $R_5$ is not hydrogen.

According to the general process above described, the compounds of formula I, wherein A is (IIa) or (IIb), $R_1$ is alkyl, $R_2$ is COOR$_5$ or CONHR$_5$ group and $R_3$ is hydrogen, can be obtained.

Preferably, the compounds that can be prepared according to this method are:
A2: 1-methyl-1,4,5,6-tetrahydro-1,6,7-triaza-as-indacene-2-carboxylic acid methyl ester;
D1: 1-methyl-1,6-dihydro-1,6,7-triaza-as-indacene-2-carboxylic acid methyl ester;
D2: 1-methyl-1,6-dihydro-1,6,7-triaza-as-indacene-2-carboxylic acid;
and D3: 1-methyl-1,6-dihydro-1,6,7-triaza-as-indacene-2-carboxylic acid amide.

In more detail, the present invention provides a first process for preparing a compound of formula I wherein A represents a fused heterocycle of the formula III as defined above and $R_1$ is hydrogen atom, which process comprises:
formylating a compound of formula XIX

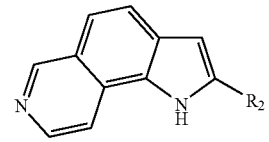

wherein $R_2$ is an aryl or heteroaryl group;
oxidizing the resultant compound of the formula I:

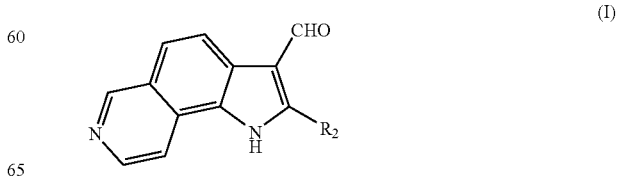

wherein $R_2$ is as defined above, reacting the resultant compound of the formula I:

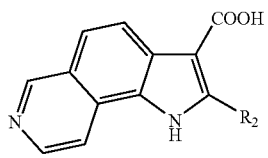

wherein $R_2$ is as defined above, with an amine compound of the formula $R_5$—$NH_2$, wherein $R_5$ is hydrogen atom or alkyl group; so as to obtain a compound of the formula I wherein A represents a fused heterocycle of the formula III as defined above, $R_2$ is as defined before, $R_3$ is CONHR$_5$ wherein $R_5$ is as defined above; and optionally converting a resultant compound of formula I into another different compound of formula I and/or into pharmaceutically acceptable salts thereof.

Scheme 10 below shows an example of the preparation of the starting compounds of the formula XIX:

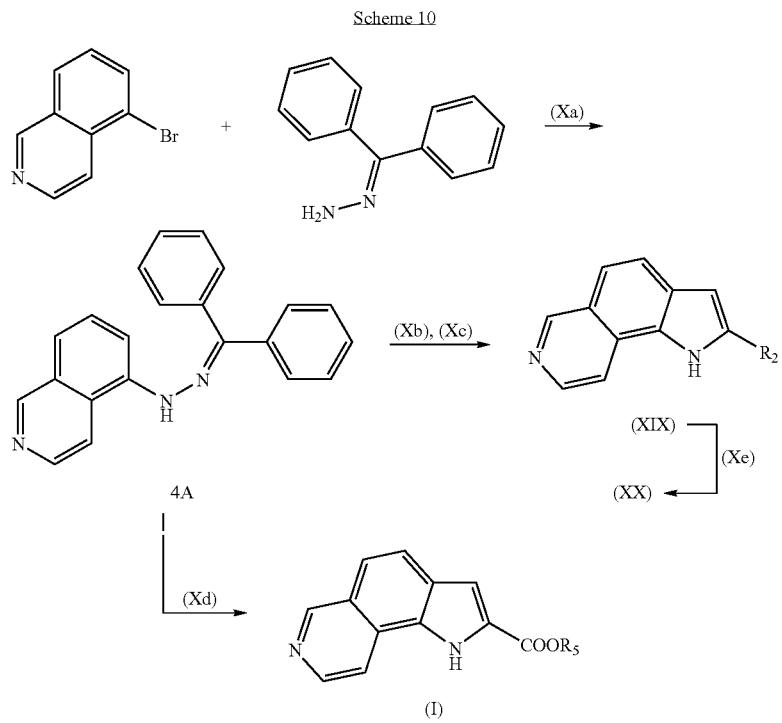

The stable crystalline N-arylbenzophenone hydrazone 4A is prepared (step Xa) from the commercially available 5-bromo-isoquinoline and benzophenone hydrazone, via the Buchwald protocol, employing palladium acetate as the catalyst and sodium ter-butoxide as the base.

When subdued to the Fischer indole synthesis conditions hydrazone 4A produces either compounds XIX, where $R_2$ is an aryl or heteroaryl group, if heated with (hetero)aryl ethanones in acidic conditions (steps Xb and Xc), or compounds I, where $R_2$ is an ester group with $R_5$ alkyl, if heated with ethylpyruvate in acidic medium (step Xd), according to a protocol is similar to that reported by Wagaw et al. *JACS*, 1999, 121, 10251.

When in compounds XIX $R_2$ is haloaryl group, for instance 4-bromophenyl, the halogen radical can be replaced with an amine, for example 4-methyl-piperazine or 4-morpholine, heating compound XIX in the presence of palladium acetate, sodium ter-butoxide and (2-biphenyl)dicyclohexyl phosphine, according to the Buchwald protocol (step Xe), a well known reaction amenable to a variety of different amines, so affording compounds of formula XX where $R_2$ is an aminoaryl group.

Scheme 11 below shows an example of the process described above for preparing the various compounds of the formula I from compounds XIX:

Scheme 11

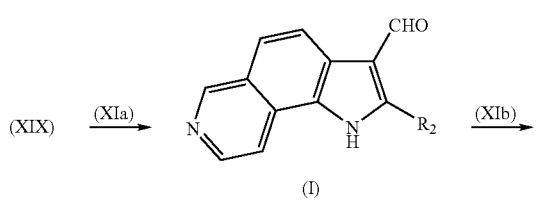

-continued

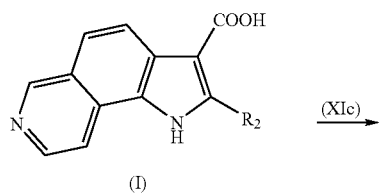

-continued

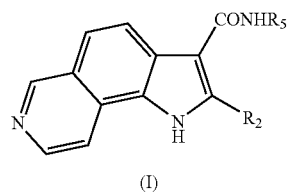

Compounds XIX, where $R_2$ is an aryl or heteroaryl group, are formylated (step XIa) via the Rieche reaction with dichloromethyl methylether and aluminum trichloride. Aldehydes I are oxidized (step XIb) under mild neutral Pinnick conditions with sodium chlorite, sulfamic acid and sodium dihydrogen phosphate to carboxylic acids I. Amidation is finally secured (step XIc) by reacting acids I with 1-(3-dimethylaminopropyl)-3-ethylcarbodiimide hydrochloride and either hydroxybenzotriazole-ammonia complex or a convenient amine in the presence of hydroxybenzotriazole, in N,N-dimethylformamide at room temperature. In the reported case the amine used may contain a protecting group, for instance a Boc group, that can be removed by acid hydrolysis is order to conclude the sequence of reactions.

According to the general process above described, the compounds of formula I, wherein A is III, Y is a double bond, $R_1$ is hydrogen, $R_2$ is $COOR_5$ or (hetero)aryl group and $R_3$ is hydrogen, formyl, $COOR_5$ or $CONHR_5$ can be obtained.

Preferably, the compounds that can be prepared according to this method are:

G1: 2-phenyl-1H-pyrrolo[2,3-f]isoquinoline-3-carbaldehyde;
G2: 2-phenyl-1H-pyrrolo[2,3-f]isoquinoline-3-carboxylic acid;
G3: 2-phenyl-1H-pyrrolo[2,3-f]isoquinoline-3-carboxylic acid amide;
G4: 2-(4-bromo-phenyl)-1H-pyrrolo[2,3-f]isoquinoline-3-carbaldehyde;
G5: 2-(4-bromo-phenyl)-1H-pyrrolo[2,3-f]isoquinoline-3-carboxylic acid;
G6: 2-(4-bromo-phenyl)-1H-pyrrolo[2,3-f]isoquinoline-3-carboxylic acid amide;
G7: 2-(4-morpholin-4-yl-phenyl)-1H-pyrrolo[2,3-f]isoquinoline-3-carbaldehyde;
G8: {(S)-3-phenyl-2-[(2-phenyl-1H-pyrrolo[2,3-f]isoquinoline-3-carbonyl)-amino]-propyl}-carbamic acid tert-butyl ester;
G9: 2-phenyl-7H-pyrrolo[2,3-f]isoquinoline-3-carboxylic acid ((S)-2-amino-1-benzyl-ethyl)-amide;
H1: 2-pyridin-4-yl-1H-pyrrolo[2,3-f]isoquinoline-3-carbaldehyde;
H2: 2-pyridin-4-yl-1H-pyrrolo[2,3-f]isoquinoline-3-carboxylic acid;
H3: 2-pyridin-4-yl-1H-pyrrolo[2,3-f]isoquinoline-3-carboxylic acid amide;

In more detail, the present invention provides a second process for preparing a compound of formula I wherein A represents a fused heterocycle of the formula III as defined above, which process comprises:

separating by chromatography a mixture of compounds of formula $I_{mix}$:

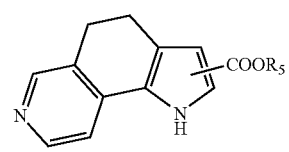

wherein $R_5$ is an alkyl group;

optionally alkylating the resultant two individual regioisomeric ester compounds of the formula I:

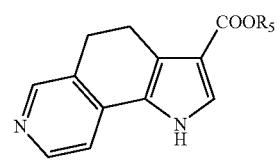

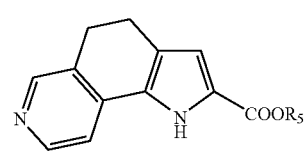

wherein $R_5$ is alkyl group, and hydrolizing the resultant compounds of the formula I:

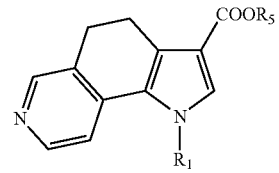

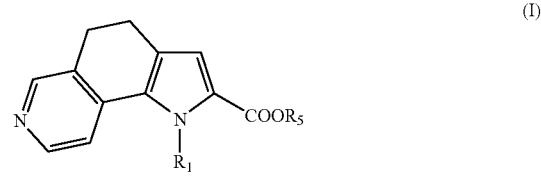

wherein $R_1$ is either hydrogen or alkyl group and $R_5$ is alkyl group;

reacting the resultant compounds of the formula I:

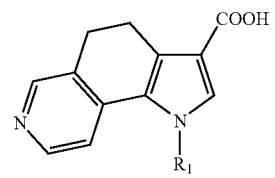

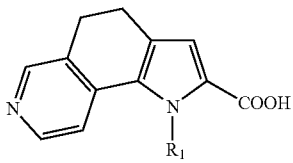
(I)

wherein $R_1$ is as defined above, with an amine compound of the formula $R_5$—$NH_2$, wherein $R_5$ is hydrogen atom or an alkyl group, optionally containing an amino protecting group; and optionally removing the N-protecting group from the $R_5$ group of resultant compound of the formula I:

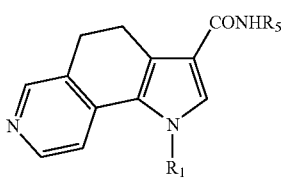
(I)

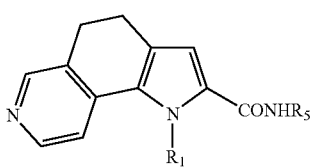
(I)

wherein $R_1$ is as defined above, and $R_5$ is hydrogen atom or an alkyl group, optionally containing an amino protecting group;

so as to obtain a compound of the formula I wherein A represents a fused heterocycle of the formula III as defined above, $R_2$ is either hydrogen atom or $CONHR_5$ group, $R_3$ is either hydrogen atom or $CONHR_5$ group and $R_5$ is hydrogen atom or an alkyl group; and optionally converting a resultant compound of formula I into another different compound of formula I and/or into pharmaceutically acceptable salts thereof;

or reacting the latter regioisomer of formula I:

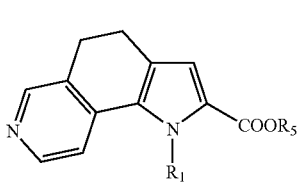
(I)

wherein $R_1$ is either hydrogen or alkyl and $R_5$ is as defined above;

with an amine compound of the formula $R_5$—$NH_2$, wherein $R_5$ is hydrogen; so as to obtain a compound of the formula I wherein A represents a fused heterocycle of the formula III as defined above, $R_1$ is as defined above, $R_2$ is $CONHR_5$ wherein $R_5$ is hydrogen and $R_3$ is hydrogen;

Scheme 12 below shows an example of the preparation of the starting mixture of the frmula $I_{mix}$:

Scheme 12

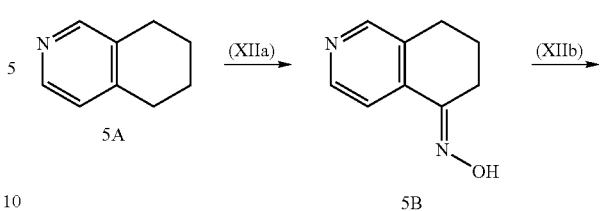

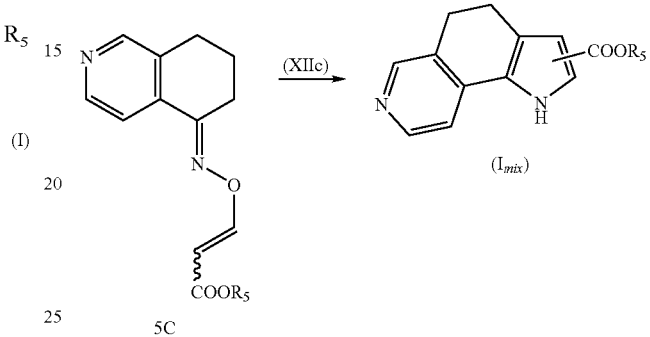

Commercial tetrahydroisoquinoline 5A is directly oxymated (step XIIa) to 5B with tert-butyl nitrite and potassium ter-butoxide by using the procedure described by Lardenois et al. *Synth. Comm.* 1996, 26, 2305. Reaction of 5B (step XIIb) with methylpropiolate in dimethylsulfoxide leads to O-vinyloxime 5C that, upon refluxing in xylene with p-toluensulfonic acid (step XIIc), rearranges and cyclises to yield a 1:1 mixture of the two regioisomeric dihydropyrroloisoquinoline scaffolds $I_{mix}$, in conditions similar to those described by Pinna et al. *Journal of Chemical Research, Synopses* 1990, 11, 360.

Schemes 13, 14 and 15 below show an example of the process described above for preparing the compounds of the formula I and for converting them into other compounds of formula I:

Scheme 13

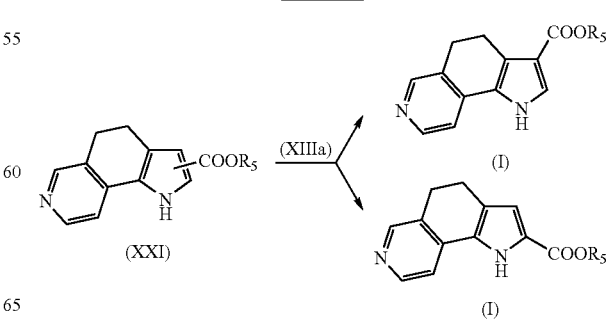

Scheme 14
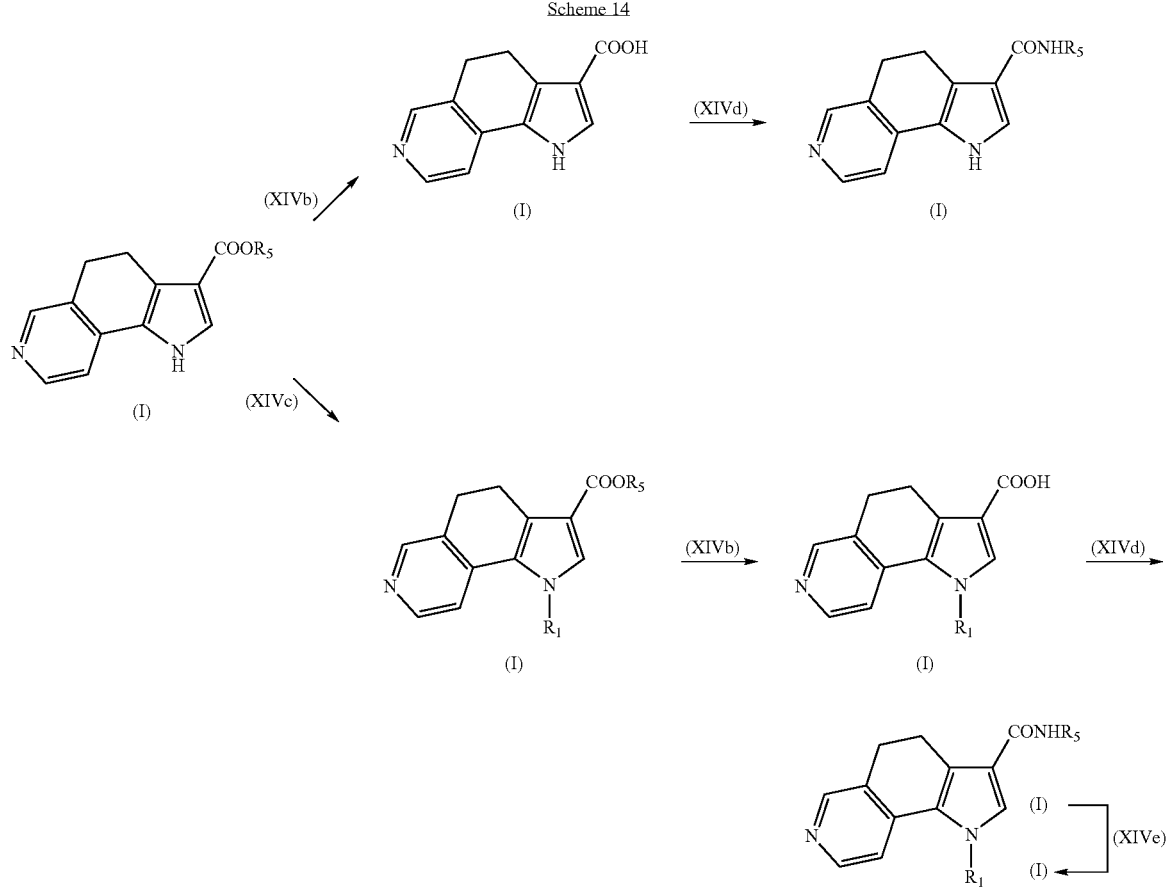
Scheme 15
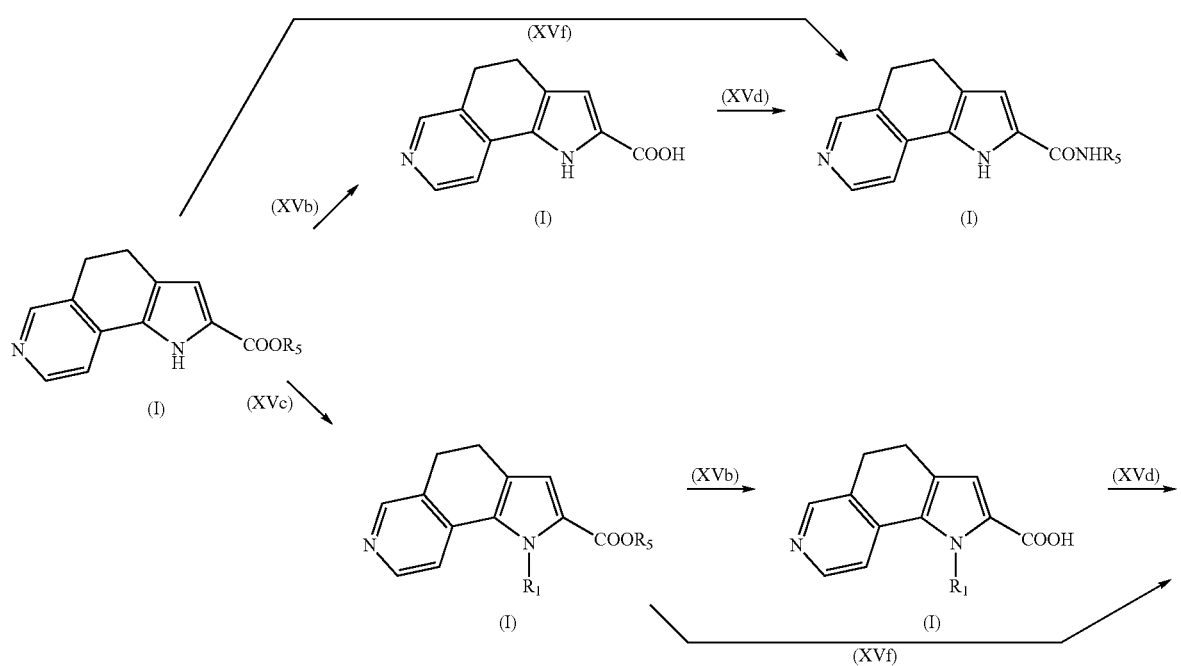

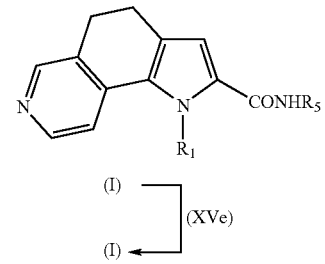

The two positional isomers I can be separated by column chromatography (step XIIIa). Regioisomeric dihydropyrroloisoquinoline esters I are independently transformed into the desired amides I, according to the same procedures that are, in the order, ester hydrolysis in basic conditions (step XIVb and XVb), optionally preceeded (step XIVc and XVc) by N-alkylation of the pyrrole ring, accomplished using alkyl halides or trifluoromethansulfonates and sodium hydride, and amidation (step XIVd and XVd) performed by reacting acids I with 1-(3-dimethylaminopropyl)-3-ethylcarbodiimide hydrochloride and either hydroxybenzotriazole-ammonia complex or a convenient amine in the presence of hydroxybenzotriazole, in N,N-dimethylformamide at room temperature. When required, acid hydrolysis (step XIVe and XVe) of the Boc N-protecting group present in $R_5$ group concludes the sequence of reactions. Alternatively, compound of formula I, having the ester group placed at position 2, can be directly converted into amide I (step XVf), by heating with aqueous concentrated ammonia in a close vessel. According to the general process above described, the compounds of formula I, wherein A is III, Y is a simple bond, $R_1$ is hydrogen atom or alkyl group, $R_2$ is hydrogen atom, $COOR_5$ or $CONHR_5$ group and $R_3$ is hydrogen atom, $COOR_5$ or $CONHR_5$ group can be obtained.

Preferably, compounds that can be the prepared according to this method are:

E1: methyl 4,5-dihydro-1H-pyrrolo[2,3-f]isoquinoline-3-carboxylate;
E3: methyl 1-(2,2,2-trifluoroethyl)-4,5-dihydro-1H-pyrrolo[2,3-f]isoquinoline-3-carboxylate;
E4: methyl 1-(2-amino-2-oxoethyl)-4,5-dihydro-1H-pyrrolo[2,3-f]isoquinoline-3-carboxylate;
E5: methyl 1-{3-[(tert-butoxycarbonyl)amino]propyl}-4,5-dihydro-1H-pyrrolo[2,3f]isoquinoline-3-carboxylate;
E6: 4,5-dihydro-1H-pyrrolo[2,3-f]isoquinoline-3-carboxylic acid;
E7: 1-(2,2,2-trifluoroethyl)-4,5-dihydro-1H-pyrrolo[2,3-f]isoquinoline-3-carboxylic acid;
E8: 1-(carboxymethyl)-4,5-dihydro-1H-pyrrolo[2,3-f]isoquinoline-3-carboxylic acid;
E9: 1-{3-[(tert-butoxycarbonyl)amino]propyl}-4,5-dihydro-1H-pyrrolo[2,3-f]isoquinoline-3-carboxylic acid;
E10: 4,5-dihydro-1H-pyrrolo[2,3-f]isoquinoline-3-carboxylic acid amide;
E11: tert-butyl {(2S)-2-[(4,5-dihydro-1H-pyrrolo[2,3-f]isoquinoline-3-ylcarbonyl)amino]-3-phenylpropyl}carbamate;
E12: tert-butyl [(2S)-3-phenyl-2-({[1-(2,2,2-trifluoroethyl)-4,5-dihydro-1H-pyrrolo[2,3f]isoquinolin-3-yl]carbonyl}amino)propyl]carbamate;
E13: tert-butyl {3-[3-({(1S)-1-benzyl-2-[(tert-butoxycarbonyl)amino]ethyl}carbamoyl)-4,5-dihydro-1H-pyrrolo[2,3-f]isoquinolin-1-yl]propyl}carbamate;
E14: N-[(1S)-2-amino-1-benzylethyl]-1-(2,2,2-trifluoroethyl)-4,5-dihydro-1H-pyrrolo[2,3f]isoquinoline-3-carboxamide;
E15: N-[(1S)-2-amino-1-benzylethyl]-4,5-dihydro-1H-pyrrolo[2,3-f]isoquinoline-3-carboxamide;
E16: N-[(1S)-2-amino-1-benzylethyl]-1-(3-aminopropyl)-4,5-dihydro-1H-pyrrolo[2,3-f]isoquinoline-3-carboxamide;
E17: methyl 1-[2-(tetrahydro-2H-pyran-2-yloxy)ethyl]-4,5-dihydro-1H-pyrrolo[2,3f]isoquinoline-3-carboxylate;
E18: (2-hydroxyethyl)-4,5-dihydro-1H-pyrrolo[2,3-f]isoquinoline-3-carboxylic acid;
E19: 1-[2-(tetrahydro-2H-pyran-2-yloxy)ethyl]-4,5-dihydro-1H-pyrrolo[2,3-f]isoquinoline-3-carboxylic acid;
E20: tert-butyl {(2S)-3-phenyl-2-[({1-[2-(tetrahydro-2H-pyran-2-yloxy)ethyl]-4,5-dihydro-1H-pyrrolo[2,3-f]isoquinolin-3-yl}carbonyl)amino]propyl}carbamate;
E21: N-[(1S)-2-amino-1-benzylethyl]-1-(2-hydroxyethyl)-4,5-dihydro-1H-pyrrolo[2,3f]isoquinoline-3-carboxamide;
L1: methyl 4,5-dihydro-1H-pyrrolo[2,3-f]isoquinoline-2-carboxylate;
L2: 4,5-dihydro-1H-pyrrolo[2,3-f]isoquinoline-2-carboxylic acid;
L3: 4,5-dihydro-1H-pyrrolo[2,3-f]isoquinoline-2-carboxylic acid amide;
L4: 2,2,2-Trifluoroethyl)-4,5-dihydro-1H-pyrrolo[2,3-f]isoquinoline-2-carboxylic acid;
L5: tert-butyl {(2S)-2-[(4,5-dihydro-1H-pyrrolo[2,3-f]isoquinolin-2-ylcarbonyl)amino]-3-phenylpropyl}carbamate;
L6: N-[(1S)-2-amino-1-benzylethyl]-4,5-dihydro-1H-pyrrolo[2,3-f]isoquinoline-2-carboxamide;
L8: tert-butyl [(2S)-3-phenyl-2-({[1-(2,2,2-trifluoroethyl)-4,5-dihydro-1H-pyrrolo[2,3f]isoquinolin-2-yl]carbonyl}amino)propyl]carbamate;
L9: N-[(1S)-2-amino-1-benzylethyl]-1-(2,2,2-trifluoroethyl)-4,5-dihydro-1H-pyrrolo[2,3f]isoquinoline-2-carboxamide;
and L10: methyl 1-(2,2,2-trifluoroethyl)-4,5-dihydro-1H-pyrrolo[2,3-f]isoquinoline-2-carboxylate.

In more detail, the present invention provides a third process for preparing a compound of formula I wherein A represents a fused heterocycle of the formula III as defined above and $R_1$ is hydrogen, which process comprises:

reacting a compound of the formula XXI:

wherein $R_5$ is an alkyl group, with halohydric acids and acetic acid;
either dehalogenating the resultant halopyrrole compound of th formula I:

(Ia)

wherein Hal is an halogen atom and $R_5$ is an alkyl group; and hydrolyzing the resultant compound of the formula I;

(I)

wherein $R_5$ is as described above, so as to obtain a compound of the formula I wherein A represents a fused heterocycle of the formula III as defined above, $R_1$ and $R_2$ are hydrogen, $R_3$ is COOH; and
optionally converting a resultant compound of formula I into another different compound of formula I and/or into pharmaceutically acceptable salts thereof.
or (hetero)arylating the halopyrrole compound of the formula Ia as defined above, so as to obtain a compound of the formula I wherein A represents a fused heterocycle of the formula III as defined above, $R_1$ is hydrogen, $R_2$ is aryl or heteroaryl group and $R_3$ is $COOR_5$ group where $R_5$ is as described above; and
optionally converting a resultant compound of formula I into another different compound of formula I and/or into pharmaceutically acceptable salts thereof.

Scheme 16 below shows an example of the preparation of the starting compounds of the formula XXI and of the process above described for preparing the compounds of the formula Ia:

Scheme 16

The cyclohexanone derivative 8A is isolated after acidic hydrolysis of oxime 5B, (prepared as described above in scheme 12, step XVIa). Bromination (step XVIb) in alpha to the ketone is obtained using bromine in acetic acid or pyridinium bromide perbromide in acetic acid with the aid of microwave irradiation at 100° C. Bromo is replaced (step XVIc) with a C-3 unit by condensation of ethylcyanoacetate in N,N-dimethylformamide at room temperature as described by Murineddu et al. *Chem. Pharm. Bull.* 2002, 50, 754. The subsequent formation (step XVId) of halopyrrole (Ia), where $R_2$ is halogen and $R_5$ is alkyl, is obtained with halohydric acids and acetic acid, by a methodology previously employed by Foley et al. *Tetr. Lett.* 1994, 35, 5989.

Scheme 17 below shows an example of the process above described for preparing the compounds of the formula I:

Scheme 17

-continued

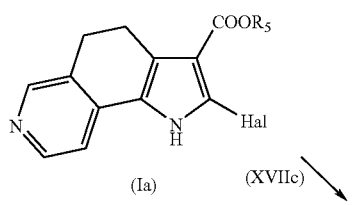

(Ia)    (XVIIc)

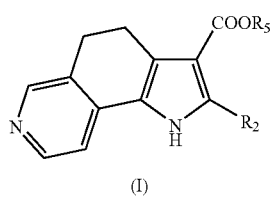

(I)

Halopyrrole (Ia) is either dehalogenated to (I) (step XVIIa), and hydrolized in basic conditions (step XVIIb) to provide acid (I), or (hetero)arylated (step XVIIc) to the 2-(hetero)aryl analog (I) by using the Suzuki coupling methods that are well known in the art. The reaction is amenable to a variety of substituted aryl or heteroaryl boronic acids. According to the general process above described, the compounds of formula I, wherein A is III, Y is a simple bond, $R_1$ is hydrogen, $R_2$ is hydrogen, halogen, aryl or heteroaryl group and $R_3$ is $COOR_5$, where $R_5$ is hydrogen or alkyl group, can be obtained.

Preferably, the compounds that can be prepared according to this method are:

E2: 4,5-dihydro-1H-pyrrolo[2,3-f]isoquinoline-3-carboxylic acid ethyl ester.
E6: 4,5-dihydro-1H-pyrrolo[2,3-f]isoquinoline-3-carboxylic acid.
F1: 2-bromo-4,5-dihydro-1H-pyrrolo[2,3-f]isoquinoline-3-carboxylic acid ethyl ester hydrobromide.
F2: 2-phenyl-4,5-dihydro-1H-pyrrolo[2,3-f]isoquinoline-3-carboxylic acid ethyl ester.
and F3: 2-o-tolyl-4,5-dihydro-1H-pyrrolo[2,3-f]isoquinoline-3-carboxylic acid ethyl ester.

In more detail, the present invention provides a fourth process for preparing a compound of formula I wherein A represents a fused heterocycle of the formula III as defined above and $R_1$ is not hydrogen, which process comprises:

protecting a compound of the formula I:

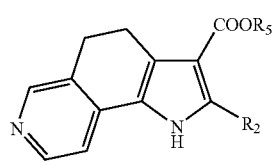

(I)

wherein $R_2$ is either halogen or (hetero)aryl and $R_5$ is alkyl;

alkylating he resultant compound of the formula XXII:

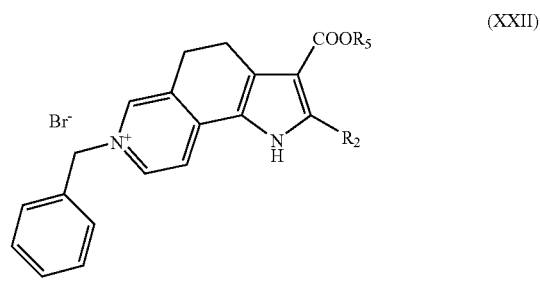

(XXII)

wherein $R_2$ and $R_5$ are as described above;

either deprotecting the resultant compound of the formula XXIII

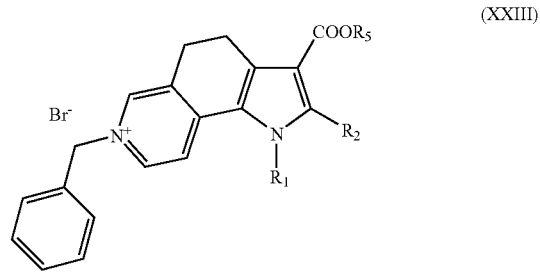

(XXIII)

wherein $R_1$ is alkyl, $R_2$ and $R_5$ are as described above; so as to obtain a compound of the formula I wherein A represents a fused heterocycle of the formula III as defined above, $R_1$ is alkyl, $R_2$ is as described above and $R_3$ is $COOR_5$ where $R_5$ is as described above;

or hydrolyzing a compound of the formula XXIII as defined above in basic medium and reacting the resultant acid compound of the formula XXIV:

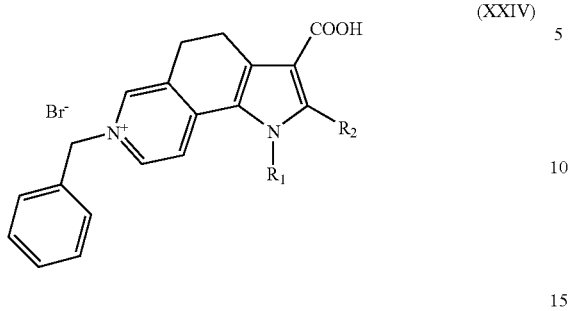

(XXIV)

wherein $R_1$ is as defined above and $R_2$ is aryl or heteroaryl group with an amine compound of the formula $R_5$—$NH_2$, wherein $R_5$ is hydrogen or alkyl group; and removing the protecting group from the resultant compound of the formula XXV:

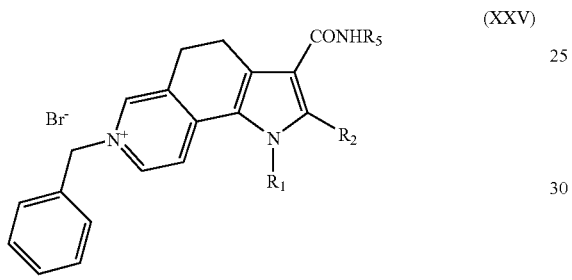

(XXV)

wherein $R_1$, $R_2$ and $R_5$ are as defined above; so as to obtain a compound of the formula I wherein A represents a fused heterocycle of the formula III as defined above, and $R_1$, $R_2$ and $R_5$ are as defined above;

optionally converting a resultant compound of formula I into another different compound of formula I and/or into pharmaceutically acceptable salts thereof.

Scheme 18 below shows an example of the process above described for preparing the compounds of the formula I:

Scheme 18

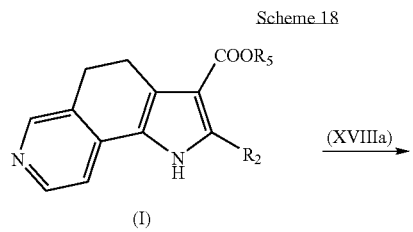

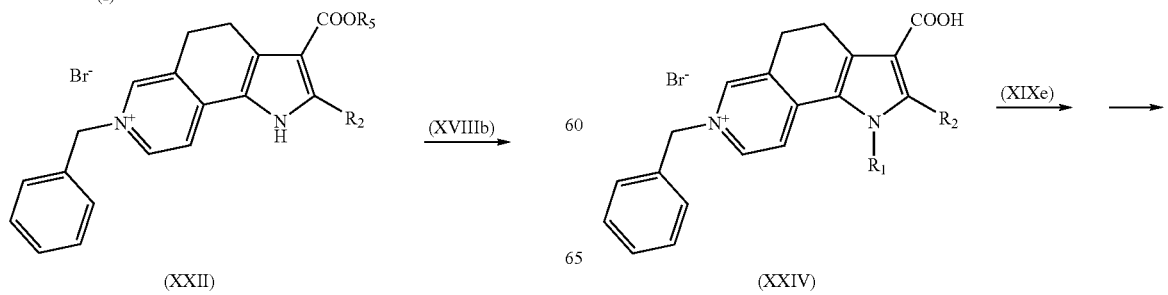

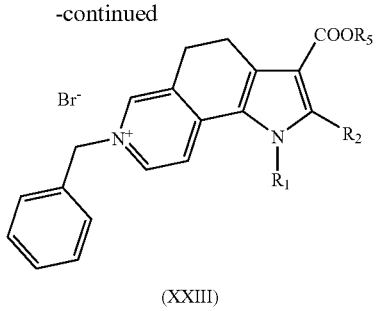

(XXIII)

↓ (XVIIIc)

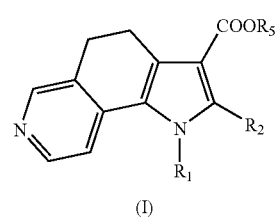

(I)

In order to N-alkylate the pyrrole it is necessary to protect the pyridine nucleus first, a precaution achieved for instance by benzylation (step XVIIIa) with sodium hydride in tetrahydrofuran at room temperature if $R_2$ is halogen, and heating without base with microwaves irradiation if $R_2$ is aryl. After N-methylation (step XVIIIb) with sodium hydride in tetrahydrofuran at room temperature, the benzyl group is oxidatively removed (step XVIIIc) in basic conditions, as reported by Haddach et al. *Tetr. Lett.* 2002, 43, 399.

Scheme 19 below shows an example of the process above described for preparing the compounds of the formula I:

Scheme 19

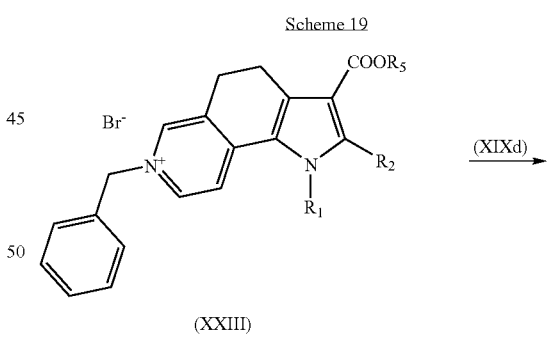

(XXIII)

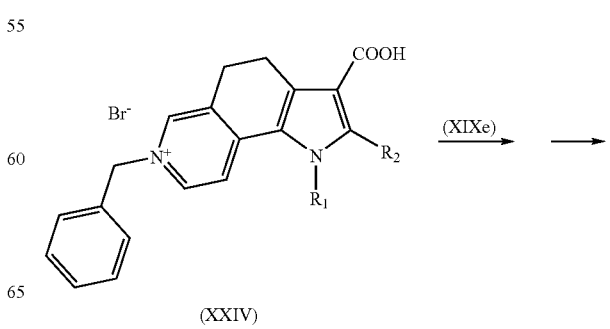

(XXIV)

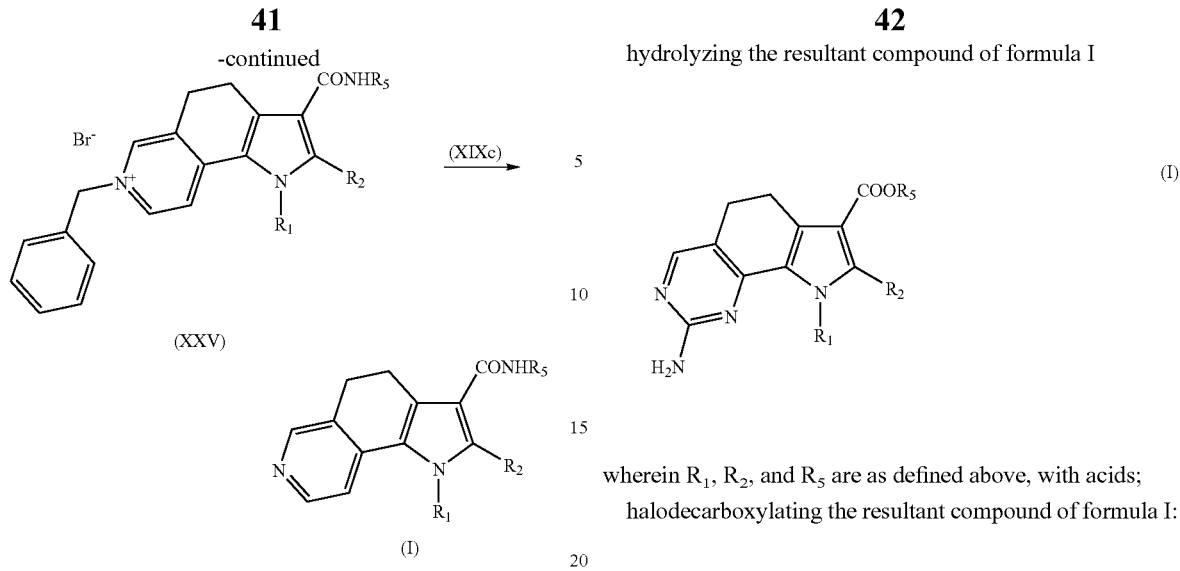

Alternatively compound XXIII is hydrolyzed (step XIXd) in basic conditions to carboxylic acid XXIV and amidated (step XIXe) by reacting the acids with 1-(3-dimethylaminopropyl)-3-ethylcarbodiimide hydrochloride and either hydroxybenzotriazole-ammonia complex or a convenient amine in the presence of hydroxybenzotriazole, in N,N-dimethylformamide at room temperature to compound XXV, a reaction amenable to a variety of amines. Debenzylation (step XIXc), in basic oxidative conditions, delivers final 2-(hetero)aryl compounds I.

According to the general process above described, the compounds of formula I, wherein A is III, Y is a simple bond, $R_1$ is alkyl, $R_2$ is halogen, aryl or heteroaryl group and $R_3$ is $COOR_5$ where $R_5$ is alkyl or $CONHR_5$, where $R_5$ is hydrogen or alkyl group, can be obtained.

Preferably, the compounds that can be prepared according to this method are:

F4: 1-methyl-2-o-tolyl-4,5-dihydro-1H-pyrrolo[2,3-f]isoquinoline-3-carboxylic acid ethyl ester;

F5: 1-methyl-2-o-tolyl-4,5-dihydro-1H-pyrrolo[2,3-f]isoquinoline-3-carboxylic acid amide;

and F6: 2-bromo-1-methyl-4,5-dihydro-1H-pyrrolo[2,3-f]isoquinoline-3-carboxylic acid ethyl ester.

In more detail, the present invention provides a first process for preparing a compound of formula I wherein A represents a fused heterocycle of the formula IV as defined above and $R_1$ is not hydrogen, which process comprises:

activating a compound of the formula XXVI:

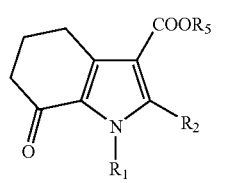

wherein $R_5$ and $R_1$ represent an alkyl group by enamination alpha to the carbonyl, and $R_2$ is a —$COOR'_5$ group wherein $R'_5$ is as defined above; and cyclizing the resultant compound with guanidine;

hydrolyzing the resultant compound of formula I wherein $R_1$, $R_2$, and $R_5$ are as defined above, with acids;

halodecarboxylating the resultant compound of formula I:

wherein $R_1$ and $R_5$ are as defined above;

dehalogenating the resultant compound of formula I with a palladated catalyst:

wherein $R_1$ and $R_5$ are as defined above;

hydrolyzing the resultant compound of formula I:

wherein $R_1$ and $R_5$ are as defined above in basic conditions; and reacting the resultant compound of the formula I:

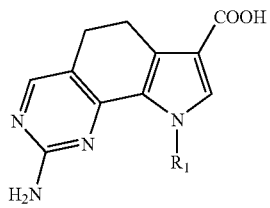

(I)

wherein $R_1$ is as defined above with an amine compound of the formula $R_5$—$NH_2$, wherein $R_5$ is hydrogen or alkyl group; so as to obtain a compound of the formula I wherein A represents a fused heterocycle of the formula IV as defined above, $R_2$ is hydrogen and $R_1$ and $R_5$ are as defined above;

optionally converting a resultant compound of formula I into another different compound of formula I and/or into pharmaceutically acceptable salts thereof.

Scheme 20 below shows an example of the preparation of the starting compounds of the formula XXVI and their conversion into the desired compounds of the formula I according to the process above described:

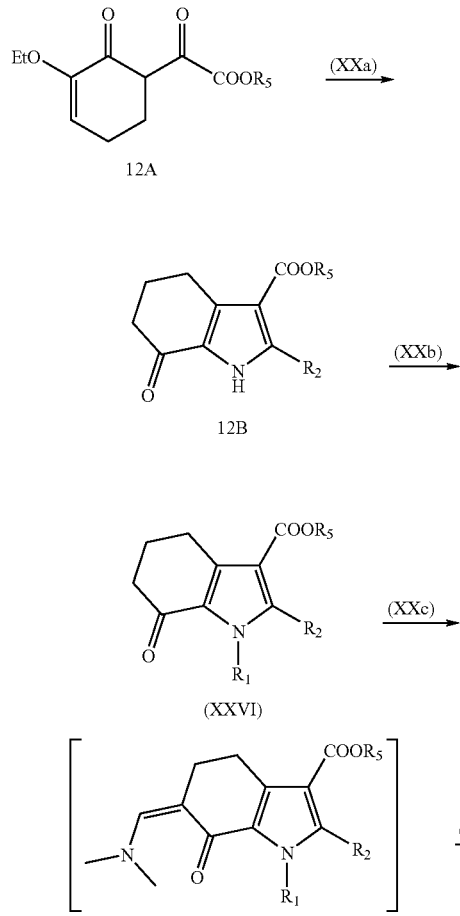

Compound 12A, obtained from commercially available 2-ethoxy-2-cyclohexen-1-one as described by Traquandi et al. in WO2004104007, is transformed (step XXa) into the tetrahydroindolone nucleus of 12B by a rhodium catalyzed cyclocondensation, as described by Takaya et al. *Organic Letters* 2001, 3, 421. Pyrrole is alkylated by the standard method (step XXb) to cyclohexanone derivative XXVI that, after activation (step XXc) by enamination alpha to the carbonyl, using a protocol similar to that of Takeuchi et al. *Chemical & Pharmaceutical Bulletin* 1983, 31, 4355, is cyclized with guanidine (step XXd) to yield the tricycle I. This reaction is amenable to a variety of N-substituted guanidines to form compounds of formula I bearing $R_6$ different from hydrogen.

Scheme 21 below shows an example of the above described process for preparing the compounds of the formula I:

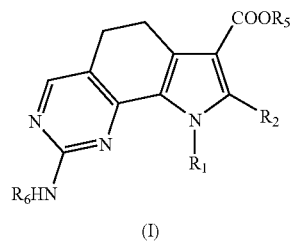

(I)

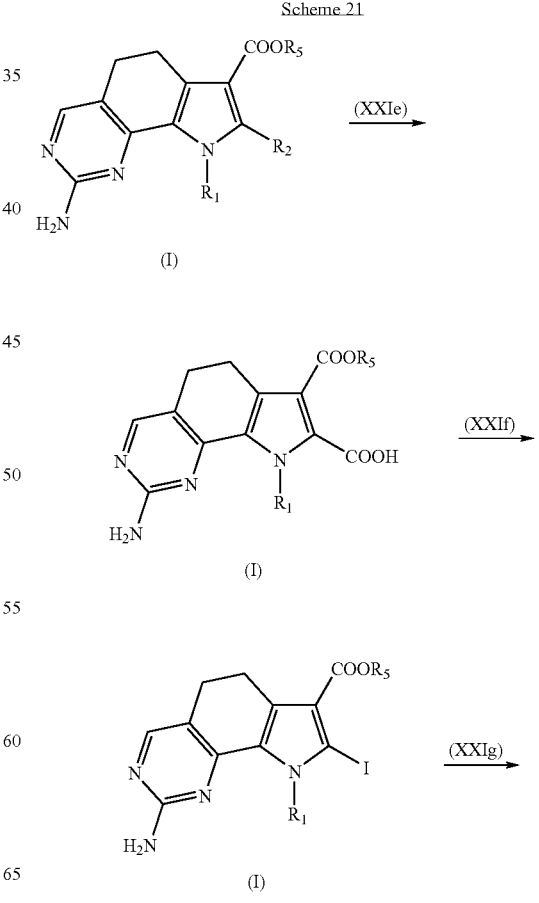

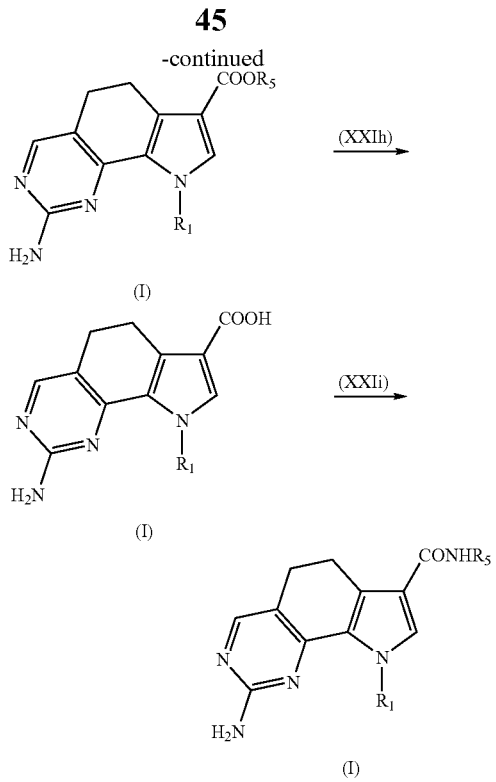

Selective hydrolysis (step XXIe) of the convenient (for example ter-butyl) ester present at position 2 of compound I is obtained in acidic medium, and decarboxylation of I is completed in two steps, via decarboxylative iodination (step XXIf) with iodine, potassium iodide and base in aqueous alcohols, a reaction pioneered by Kleinspehn et al. *JACS* 1954, 76, 5641, followed by deiodination (step XXIg) to I, performed with palladium tetrakis and sodium formate in N,N-dimethylformamide, as described by Leung et al. *Tetr. Lett.* 1999, 40, 7189. Ester saponification (XXIh) is achieved in basic conditions and amidation (step XXIi) is accomplished as usual, by reacting acid I with 1-(3-dimethylaminopropyl)-3-ethylcarbodiimide hydrochloride and either hydroxybenzotriazole-ammonia complex or a convenient amine in the presence of hydroxybenzotriazole, in N,N-dimethylformamide at room temperature.

According to the general process above described, the compounds of formula I, wherein A is IV, Y is a simple bond, $R_1$ is alkyl, $R_2$ is hydrogen, halogen, or $COOR_5$ where $R_5$ is hydrogen or alkyl and $R_3$ is $COOR_5$, where $R_5$ is hydrogen or alkyl, or $CONHR_5$, where $R_5$ is hydrogen, can be obtained.

Preferably, the compounds that can be prepared according to this method are:

M1: 8-amino-1-methyl-4,5-dihydro-1H-1,7,9-triaza-cyclopenta[a]naphthalene-3-carboxylic acid ethyl ester;
M2: 8-amino-1-methyl-4,5-dihydro-1H-1,7,9-triaza-cyclopenta[a]naphthalene-3-carboxylic acid;
M3: 8-amino-1-methyl-4,5-dihydro-1H-1,7,9-triaza-cyclopenta[a]naphthalene-3-carboxylic acid amide;
N1: 8-amino-2-iodo-1-methyl-4,5-dihydro-1H-1,7,9-triaza-cyclopenta[a]naphthalene-3-carboxylic acid ethyl ester;
N5: 8-amino-1-methyl-4,5-dihydro-1H-1,7,9-triaza-cyclopenta[α]naphthalene-2,3-dicarboxylic acid diethyl ester;
N6: 8-amino-1-methyl-4,5-dihydro-1H-1,7,9-triaza-cyclopenta[a]naphthalene-2,3-dicarboxylic acid 2-tert-butyl ester 3-ethyl ester;
and N7: 8-amino-1-methyl-4,5-dihydro-1H-1,7,9-triaza-cyclopenta[a]naphthalene-2,3-dicarboxylic acid 3-ethyl ester.

In more detail, the present invention provides a second process for preparing a compound of formula I wherein A represents a fused heterocycle of the formula IV as defined above and $R_1$ is not hydrogen, which process comprises:
hydrolyzing the compound of formula I

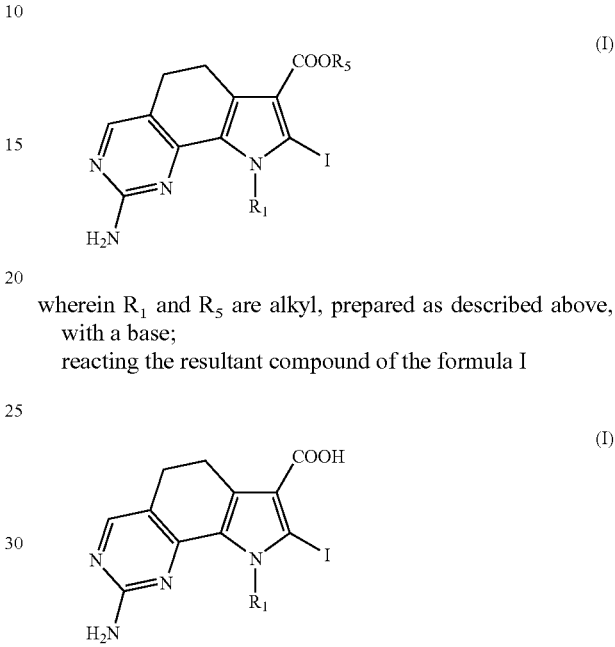

wherein $R_1$ and $R_5$ are alkyl, prepared as described above, with a base;
reacting the resultant compound of the formula I

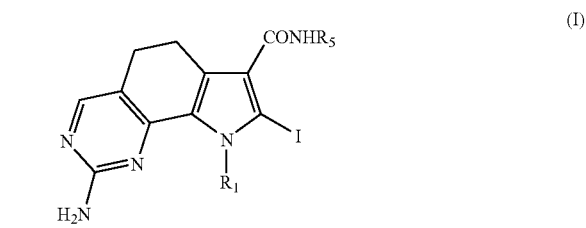

wherein $R_1$ is as defined above, with an amine compound of the formula $R_5$—$NH_2$, wherein $R_5$ is hydrogen or alkyl group;
(hetero)arylating (step c) the resultant compound of the formula I

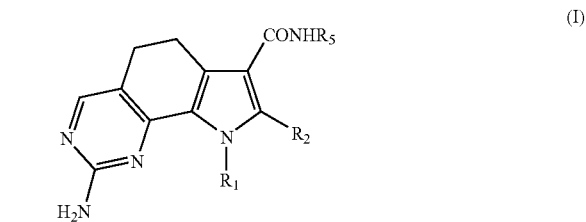

wherein $R_1$ is as defined above and $R_5$ is hydrogen or alkyl group;
oxidizing the resultant compound of formula I wherein $R_1$ and $R_5$ are as defined above and $R_2$ is aryl or heteroaryl group; so as to obtain a compound of the formula I wherein A represents a fused heterocycle of the formula IV as defined above, Y is a double bond, $R_2$ is aryl or heteroaryl group and $R_1$ and $R_5$ are as defined above; and optionally converting a resultant compound of formula I into another different compound of formula I and/or into pharmaceutically acceptable salts thereof.

Scheme 22 below shows an example of the process above described for preparing the compounds of the formula I:

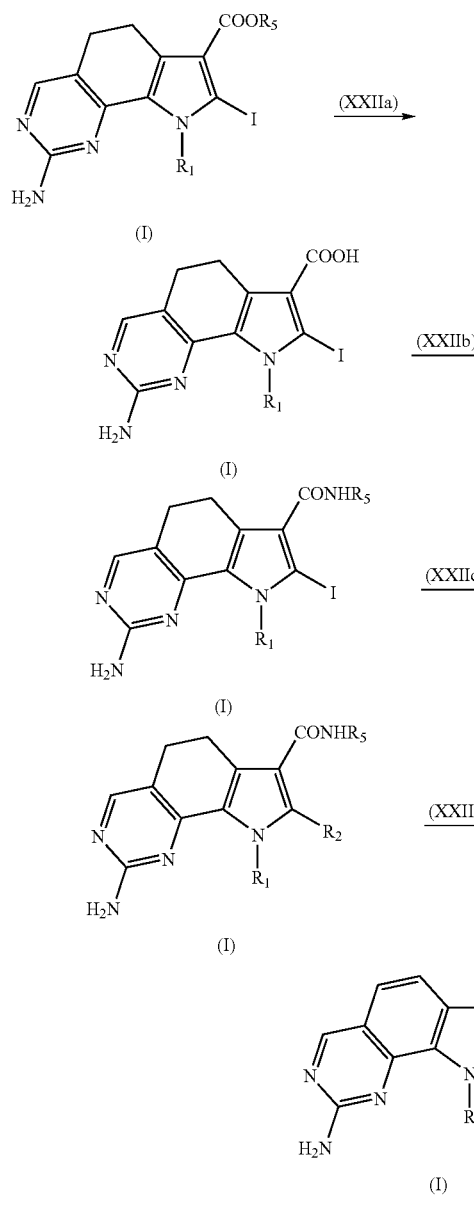

Alternatively to the deiodination reaction shown in Scheme 21, iodoester I is hydrolyzed in basic conditions (step XXIIa) and amidated as usual (step XXIIb) by reacting acid I with 1-(3-dimethylaminopropyl)-3-ethylcarbodiimide hydrochloride and either hydroxybenzotriazole-ammonia complex or a convenient amine in the presence of hydroxybenzotriazole, in N,N-dimethylformamide at room temperature. (Hetero)arylation reaction of iodoamide I (step XXIIc), via well known Suzuki coupling methods, with the convenient boronic acid derivative and a palladated catalyst, for instance dichloroditriphenylphosphinepalladium, supplies compound I. The reaction is amenable to a variety of substituted aryl or heteroaryl boronic acids. The optional oxidation (step XXIId) to the fully aromatic compound I is achieved with palladium on carbon in refluxing xylene. Preferably, the compounds that can be prepared according to this method are:

N2: 8-amino-2-iodo-1-methyl-4,5-dihydro-1H-1,7,9-triaza-cyclopenta[a]naphthalene-3-carboxylic acid;

N3: 8-amino-2-iodo-1-methyl-4,5-dihydro-1H-1,7,9-triaza-cyclopenta[a]naphthalene-3-carboxylic acid amide;

N4: 8-amino-1-methyl-2-phenyl-4,5-dihydro-1H-1,7,9-triaza-cyclopenta[a]naphthalene-3-carboxylic acid amide;

and N10: 8-amino-1-methyl-2-phenyl-1H-1,7,9-triaza-cyclopenta[a]naphthalene-3-carboxylic acid amide. In more detail, the present invention provides a third process for preparing a compound of formula I wherein A represents a fused heterocycle of the formula IV as defined above and $R_2$ is an aryl or heteroaryl group, which process comprises: bridging the heteroaromatic rings of the compound of formula XXVII:

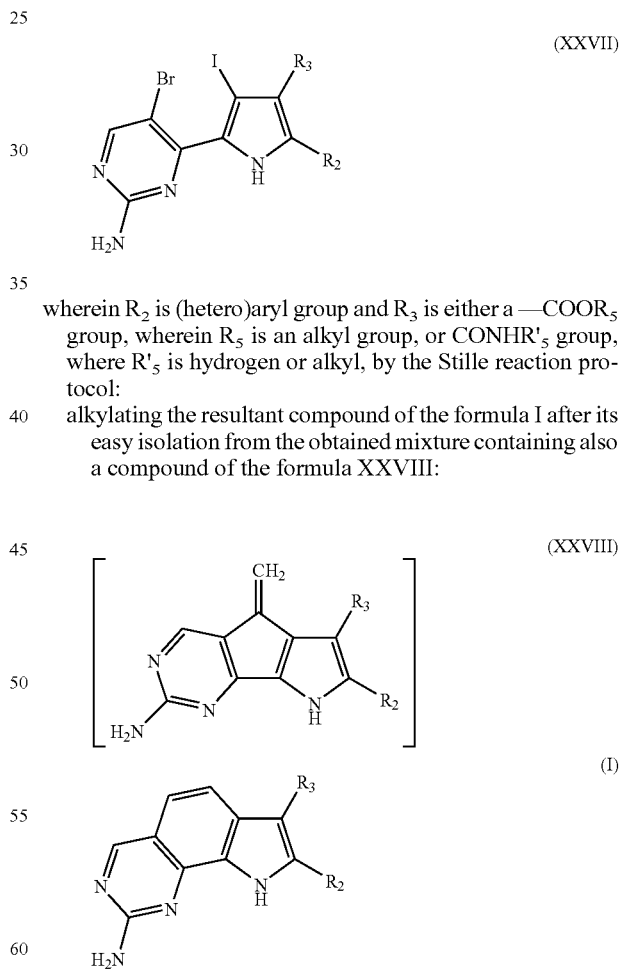

wherein $R_2$ is (hetero)aryl group and $R_3$ is either a —COOR$_5$ group, wherein $R_5$ is an alkyl group, or CONHR'$_5$ group, where R'$_5$ is hydrogen or alkyl, by the Stille reaction protocol:

alkylating the resultant compound of the formula I after its easy isolation from the obtained mixture containing also a compound of the formula XXVIII:

wherein $R_2$ and $R_3$ are as described above, so as to obtain a compound of the formula I wherein A represents a fused heterocycle of the formula IV as defined above, Y is a double bond, $R_1$ is alkyl, $R_2$ and $R_3$ are as defined above; and optionally converting a resultant compound of formula I into another different compound of formula I and/or into pharmaceutically acceptable salts thereof.

Starting iodobromopyrroles XXVII are secured from 1-(2-amino-pyrimidin-4-yl)-2-bromo-ethanone and 3-oxo-3-phenyl-propionic acid ethyl ester, as described in EP06111766.

Scheme 23 below shows an example of the above described process for preparing the compounds of the formula I:

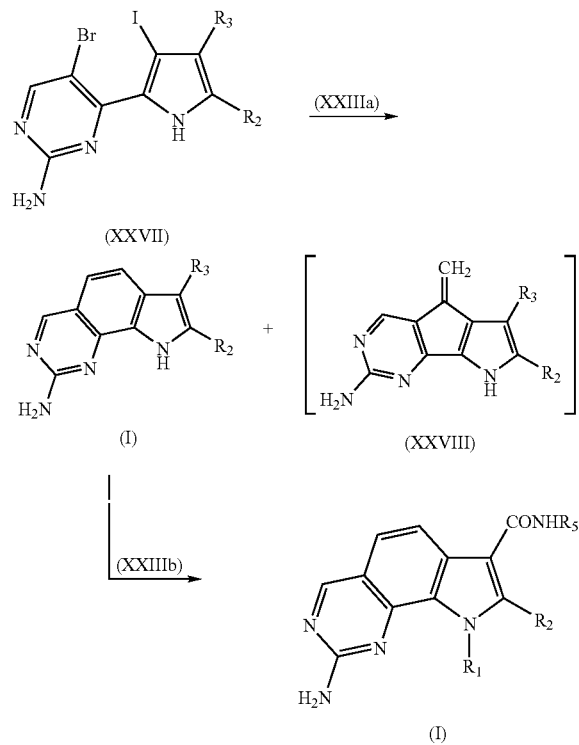

Compounds XXVII, exposed to the Stille reaction conditions (step XXIIIa), originate a 1:1 mixture of the isomeric compounds I and XXVIII, that can be easily separated by chromatography. Eventually, compound of formula I can be alkylated (step XXIIIb) with the standard procedure to give amides I.

Preferably, the compounds that can be prepared according to this method are:

N8: 8-amino-2-phenyl-1H-1,7,9-triaza-cyclopenta[a]naphthalene-3-carboxylic acid ethyl ester;
N9: 8-amino-2-phenyl-1H-1,7,9-triaza-cyclopenta[a]naphthalene-3-carboxylic acid amide;
and N10: 8-amino-1-methyl-2-phenyl-1H-1,7,9-triaza-cyclopenta[a]naphthalene-3-carboxylic acid amide.

PHARMACOLOGY

The compounds of formula (I) are active as protein kinase inhibitors and are therefore useful, for instance, to restrict the unregulated proliferation of tumor cells.

In therapy, they may be used in the treatment of various tumors, such as those formerly reported, as well as in the treatment of other cell proliferative disorders such as psoriasis, vascular smooth cell proliferation associated with atherosclerosis and post-surgical stenosis and restenosis and in the treatment of Alzheimer's disease.

Inhibition Assay of Cdc7 Activity

The inhibiting activity of putative Cdc7 inhibitors and the potency of selected compounds is determined through a method of assay based on the use of Dowex resin capture technology.

The assay consists of the transfer of radioactivity labeled phosphate moiety by the kinase to an acceptor substrate. The resulting 33P-labeled product is separated from unreacted tracer, transferred into a scintillation cocktail and light emitted is measured in a scintillation counter.

The inhibition assay of Cdc7/Dbf4 activity is performed according to the following protocol.

The MCM2 substrate is trans-phosphorylated by the Cdc7/Dbf4 complex in the presence of ATP traced with $\gamma^{33}$-ATP. The reaction is stopped by addition of Dowex resin in the presence of formic acid. Dowex resin particles capture unreacted $\gamma^{33}$-ATP and drag it to the bottom of the well while $^{33}$P phosphorylated MCM2 substrate remains in solution. The supernatant is collected, transferred into Optiplate plates and the extent of substrate phosphorylation is evaluated by β counting.

The inhibition assay of Cdc7/Dbf4 activity was performed in 96 wells plate according to the following protocol.

To each well of the plate were added:

10 μl test compound (10 increasing concentrations in the nM to uM range to generate a dose-response curve). The solvent for test compounds contained 3% DMSO. (final concentration 1%)

10 μl substrate MCM2 (6 μM final concentration), a mixture of cold ATP (2 μM final concentration) and radioactive ATP (1/5000 molar ratio with cold ATP).

10 μl enzyme (Cdc7/Dbf4, 2 nM final concentration) that started the reaction. The buffer of the reaction consisted in 50 mM HEPES pH 7.9 containing 15 mM MgCl$_2$, 2 mM DTT, 3 uM NaVO$_3$, 2 mM glycerophosphate and 0.2 mg/ml BSA.

After incubation for 60 minutes at room temperature, the reaction was stopped by adding to each well 150 μl of Dowex resin in the presence of 150 mM formic acid. After other 60 min incubation, 50 μl of suspension were withdrawn and transferred into 96-well OPTIPLATEs containing 150 μl of MicroScint 40 (Packard); after 5-10 minutes shaking the plates were read for 1 min in a Packard TOP-Count radioactivity reader.

IC50 determination: inhibitors were tested at different concentrations ranging from 0.0005 to 10 μlM. Experimental data were analyzed by the computer program Assay Explorer using the four parameter logistic equation:

$$y=\text{bottom}+(\text{top}-\text{bottom})/(1+10\hat{\,}((\log \text{IC50}-x)*\text{slope}))$$

where x is the logarithm of the inhibitor concentration, y is the response; y starts at bottom and goes to top with a sigmoid shape.

Most compounds of formula (I) of the present invention showed IC$_{50}$ values on Cdc7/Dbf4 in the low micromolar range.

In particular, the compounds coded E6, E7, E10, F1, G7, G9, L2, N4 showed IC$_{50}$ values on Cdc7/Dbf4 lower than 1 micromolar, while the compounds coded B2, B3, C1, C2, F5, G3, G5, G6, H1, H3, N9, N10 showed IC$_{50}$ values on Cdc7/Dbf4 lower than 100 nM.

In addition the selected compounds have been characterized for specificity on a panel of many other kinases, among which Cdk2A, IGF1-R, Aurora-2, AKT1, PLK1, SULU1, ERK2, CK2, GSK3β, PKAα, PKCβ, VEGFR$_3$, PDGFR.

Inhibition Assay of Cdk2/Cyclin A Activity

Kinase reaction: 1.5 µM histone H1 substrate, 25 µM ATP (0.2 µCi P33γ-ATP), 30 ng of baculovirus co-expressed Cdk2/Cyclin A, 10 µM inhibitor in a final volume of 100 µl buffer (TRIS HCl 10 mM pH 7.5, MgCl$_2$ 10 mM, 7.5 mM DTT) were added to each well of a 96 U bottom well plate. After 10 min at 37° C. incubation, reaction was stopped by 20 µl EDTA 120 mM.

Capture: 100 µl were transferred from each well to Multiscreen plate, to allow substrate binding to phosphocellulose filter. Plates were then washed 3 times with 150 µl/well PBS Ca$^{++}$/Mg$^{++}$ free and filtered by Multiscreen filtration system.

Detection: filters were allowed to dry at 37° C., then 100 µl/well scintillant were added and 33P labeled histone H1 was detected by radioactivity counting in the Top-Count instrument.

Results: data were analyzed and expressed as % inhibition referred to total activity of enzyme (=100%).

All compounds showing inhibition ≧50% were further analyzed in order to study and define potency (IC50) as well as the kinetic-profile of inhibitor through Ki calculation.

IC50 determination: the protocol used was the same described above, where inhibitors were tested at different concentrations ranging from 0.0045 to 10 µM. Experimental data were analyzed by the computer program GraphPad Prizm using the four parameter logistic equation:

$$y=\text{bottom}+(\text{top}-\text{bottom})/(1+10^\wedge((\log \text{IC50}-x)*\text{slope}))$$

where x is the logarithm of the inhibitor concentration, y is the response; y starts at bottom and goes to top with a sigmoid shape.

Ki calculation: either the concentration of ATP and histone H1 substrate were varied: 4, 8, 12, 24, 48 µM for ATP (containing proportionally diluted P$^{33}$γ-ATP) and 0.4, 0.8, 1.2, 2.4, 4.8 µM for histone were used in absence and presence of two different, properly chosen inhibitor concentrations.

Experimental data were analyzed by the computer program "SigmaPlot" for Ki determination, using a random bireactant system equation:

$$v = \frac{V\max \frac{(A)(B)}{aKAKB}}{1 + \frac{(A)}{KA} + \frac{(B)}{KB} + \frac{(A)(B)}{aKAKB}}$$

where A=ATP and B=histone H1.

Inhibition Assay of Cdk2/Cyclin E Activity

Kinase reaction: 1.5 µM histone H1 (Sigma #H-5505) substrate, 25 µM ATP (0.2 µCi P$^{33}$γ-ATP), 15 ng of baculovirus co-expressed cdk2/GST-Cyclin E, suitable concentrations of inhibitor in a final volume of 100 µl buffer (TRIS HCl 10 mM pH 7.5, MgCl$_2$ 10 mM, 7.5 mM DTT+0.2 mg/ml BSA) were added to each well of a 96 U bottom well plate. After 10 min at 37° C. incubation, reaction was stopped by 20 µl EDTA 120 mM.

Capture: 100 µl were transferred from each well to Multiscreen plate, to allow substrate binding to phosphocellulose filter. Plates were then washed 3 times with 150 µl/well PBS Ca$^{++}$/Mg$^{++}$ free and filtered by Multiscreen filtration system.

Detection: filters were allowed to dry at 37° C., then 100 µl/well scintillant were added and $^{33}$P labeled histone H1 was detected by radioactivity counting in the Top-Count instrument.

Inhibition Assay of Cdk1/Cyclin B1 Activity

Kinase reaction: 1.5 µM histone H1 (Sigma #H-5505) substrate, 25 µM ATP (0.2 µCi P$^{33}$γ-ATP), 30 ng of baculovirus co-expressed Cdk1/Cyclin B1, suitable concentrations of inhibitor in a final volume of 100 µl buffer (TRIS HCl 10 mM pH 7.5, MgCl$_2$ 10 mM, 7.5 mM DTT+0.2 mg/ml BSA) were added to each well of a 96 U bottom well plate. After 10 min at 37° C. incubation, reaction was stopped by 20 µl EDTA 120 mM.

Capture: 100 µl were transferred from each well to Multiscreen plate, to allow substrate binding to phosphocellulose filter. Plates were then washed 3 times with 150 µl/well PBS Ca$^{++}$/Mg$^{++}$ free and filtered by Multiscreen filtration system.

Detection: filters were allowed to dry at 37° C., then 100 µl/well scintillant were added and $^{33}$P labeled histone H1 was detected by radioactivity counting in the Top-Count instrument.

Inhibition Assay Cdk4/Cyclin D1 Activity

Kinase reaction: 0.4 µM mouse GST-Rb (769-921) (#sc-4112 from Santa Cruz) substrate, 10 µM ATP (0.5 µCi P$^{33}$γ-ATP), 100 ng of baculovirus expressed GST-Cdk4/GST-Cyclin D1, suitable concentrations of inhibitor in a final volume of 50 µl buffer (TRIS HCl 10 mM pH 7.5, MgCl$_2$ 10 mM, 7.5 mM DTT+0.2 mg/ml BSA) were added to each well of a 96 U bottom well plate. After 40 min at 37° C. incubation, reaction was stopped by 20 µl EDTA 120 mM.

Capture: 60 µl were transferred from each well to Multiscreen plate, to allow substrate binding to phosphocellulose filter. Plates were then washed 3 times with 150 µl/well PBS Ca$^{++}$/Mg$^{++}$ free and filtered by Multiscreen filtration system.

Detection: filters were allowed to dry at 37° C., then 100 µl/well scintillant were added and $^{33}$P labeled Rb fragment was detected by radioactivity counting in the Top-Count instrument.

Inhibition Assay of Cdk5/p25 Activity

The inhibition assay of Cdk5/p25 activity was performed according to the following protocol.

Kinase reaction: 1.0 µM biotinylated histone peptide substrate, 0.25 µCi P$^{33}$γ-ATP, 4 nM Cdk5/p25 complex, 0-100 µM inhibitor in a final volume of 100 µl buffer (Hepes 20 mM pH 7.5, MgCl$_2$ 15 mM, 1 mM DTT) were added to each well of a 96 U bottom well plate. After 20 min at 37° C. incubation, the reaction was stopped by the addition of 500 µg SPA beads in phosphate-buffered saline containing 0.1% Triton X-100, 50 M ATP and 5 mM EDTA. The beads were allowed to settle, and the radioactivity incorporated in the 33P-labelled peptide was detected in a Top Count scintillation counter.

Results: Data were analyzed and expressed as % Inhibition using the formula:

$$100X(1-(\text{Unknown}-\text{Bkgd})/(\text{Enz. Control}-\text{Bkgd}))$$

IC50 values were calculated using a variation of the four parameter logistics equation:

$$Y=100/[1+10^\wedge((\log \text{EC50}-X)*\text{Slope})]$$

Where X=log(M) and Y=% Inhibition.

Method for AKT Kinase Inhibition Assay: Dowex Technique
General Principle for Kinase Inhibition Assays Specific peptide or protein substrates are trans-phosphorylated by their specific serine -threonine or tyrosine kinase, in the presence of ATP traced with $^{33}$Pγ-ATP, and in the presence of their own optimal buffer and cofactors.

At the end of the phosphorylation reaction, more than 98% cold ATP and radioactive ATP is captured by an excess of the ion exchange dowex resin; the resin then settles down to the bottom of the reaction plate by gravity.

Supernatant, containing the phosphorylated substrate, is subsequently withdrawn and transferred into a counting plate, then evaluated by β-counting.

Reagents/Assay Conditions
Dowex Resin Preparation 500 g of wet resin (SIGMA, custom prepared resin DOWEX 1×8 200-400 mesh, 2.5 Kg) are weighed out and diluted to 2 l in 150 mM sodium formate, pH 3.00.

The resin is allowed to settle down (some hours) and then the supernatant is discarded. After three washes as above over a couple of days, the resin is allowed to settle, the supernatant is discarded and two volumes of 150 mM sodium formate buffer are added per volume of pellet.

The pH is then measured and should be around 3.00.

The washed resin is stable for more than one week; the stock resin is kept at 4° C. before use.

Kinase Buffer (KB):
TRIS 50 mM, pH 7.5
$MgCl_2$ 10 mM
DTT 1 mM
$NaVO_3$ 3 M
BSA 0.2 mg/ml
Assay conditions (final concentrations) for AKT1
Enzyme concentration (AKT1)=5 nM
Substrate concentration (Aktide, 14 residues peptide, from PRIMM)=30 μM
ATP=132 μM
$^{33}$P-γ-ATP=0.88 nM
Robotized Dowex Assay The "test" mixture consisted of:
1) 3× Enzyme mix (done in Kinase Buffer 3×), 5 μl/well
2) 3× substrate and ATP mix (done in $DDH_2O$), together with $^{33}$P-γ-ATP, 5 μl/well
3) 3× test compounds (diluted into $DDH_2O$-3% DMSO)-5 μl/well Dilution of Compounds Test compounds are received as 100% DMSO solution at the indicated concentrations:

i—for % inhibition studies, individual dilution plates at 1 mM, 100 μM and 10 μM are prepared in 100% DMSO, then diluted at a 3× concentration (30, 3 and 0.3 μM) in $DDH_2O$, 3% DMSO. A Multimek 96 (Beckman) is used for dilutions and compound pipetting into the test plates ii—for $IC_{50}$ determination, compounds are received as 1 mM, 100% DMSO solutions, plated into the first column of a microtiter plate (A1 to G1), 100 μl.

Well H1 is left empty for the internal standard inhibitor, staurosporine.

A Biomek 2000 (Beckman) is used for serial 1:3 dilutions in water, 3% DMSO, from column A1 to A10 and for all the seven compounds in the plate. In a standard experiment, the highest concentration of all compounds is 30 μM, then diluted in the final test mixture down to 10 μM.

Columns 11 and 12 are left available for total activity reference and background evaluation.

Assay Scheme 384-well plates, V bottom (test plates) are prepared with 5 μl of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×).

At the start of the run, the robot aspirates 5 μl of ATP mix, makes an air gap inside the tips (3 μl) and aspirates 5 μl of AKT mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 μl of dowex resin suspension into the reaction mix. Three cycles of mixing are done immediately after the addition of the resin.

The resin suspension has to be carefully stirred during the whole step of reaction stop because its settling velocity is extremely high.

The resin suspension is very dense; in order to avoid tip clogging, wide bore tips are used to dispense it.

Another mixing cycle is performed after all the plates are stopped, this time using normal tips: the plates are then allowed to rest for about one hour in order to maximize ATP capture. At this point, 20 μl of the supernatant are transferred into 384-Optiplates (Perkin-Elmer), with 70 μl of Microscint 40 (Perkin-Elmer); after 5 min of orbital shaking the plates are read on a Perkin-Elmer Top Count radioactivity counter.

Data are analysed by an internally customized version of the SW package "Assay Explorer" that provides either % inhibition for primary assays or sigmoidal fittings of the ten-dilutions curves for IC50 determination, for the secondary assays/hit confirmation routines.

Analogously the inhibition assay of AKT2 or AKT3 activity were performed by employing the relative assay conditions:

Assay Conditions (Final Concentrations) for AKT2
Enzyme concentration (AKT2)=10 nM
Substrate concentration (Aktide, 14 residues peptide, from PRIMM)=8.5 M
ATP=396 μM
$^{33}$P-γ-ATP=0.88 nM
Assay Conditions (Final Concentrations) for AKT3
Enzyme concentration (AKT2)=2.5 nM
Substrate concentration (Aktide, 14 residues peptide, from PRIMM)=30 μM
ATP=180 μM
$^{33}$P-γ-ATP=0.88 nM GFP-Foxo3a Nuclear Translocation Assay using MCF7 GFP-Foxo3aDT cells
Cells MCF7 GFP-Foxo3aDT are MCF-7 human mammary adenocarcinoma cells (originating from ECACC, European Collection of Cell Cultures, Cat. #86012803) stably transfected with a mammalian expression vector (pEGFP-C, Clontech) encoding a fusion protein consisting of amino acid residues 1-593 of human FOXO3a fused in-frame to the C-terminus of EGFP (the complete nucleotide sequence of the vector is attached at the foot of this document in text form). The expressed fluorescent protein normally resides in the cytoplasm, but translocates to the nucleus in presence of inhibitors of the PI-3 kinase/AKT pathway.

MCF7 GFP-Foxo3aDT cells (clone 4-2A) are maintained in E-MEM+10% FCS+2 mM L-Glutamine+1% NEAA+400 μg/ml G418. Cultures are split approximately 1:3 twice weekly, seeding 1.5×10$^6$ cells in a total of 20 ml medium per T75 tissue culture flask.

Reagents
DAPI: 4',6-Diamidino-2-phenylindole, dilactate, Sigma
EMEM: Earle's modified Eagle's medium: Gibco
FBS, Foetal bovine serum: Euroclone
G418, geneticin: Gibco
Hoechst: Hoechst 33342 (bisBenzimide), Sigma
Leptomycin B: Sigma
L-glutamine, 200 mM (100× solution): Gibco
LY-294002: Sigma
NP-40, Nonidet P 40 nonionic detergent: Sigma
NEAA (Non essential Aminoacids, 100× solution): Gibco
Wortmannin: Sigma Assay Protocol 1) Trypsinise semi/near-confluent cultures of MCF7 GFP-Foxo3aDT cells and resuspend washed cell pellet in EMEM/10% FCS/1% NEAA at a density of $1.5 \times 10^5$ cells/ml. Plate 100 µl/well cell suspension in 96 well assay plate (Packard ViewPlate cat. #6005182) and incubate for 24 hours (37° C., 95% air/5% $CO_2$, 100% relative humidity) prior to treatment. After this incubation, cells should be in exponential growth phase.

2) Treat wells by addition of 50 µl EMEM/10% FCS/1% NEAA containing appropriate concentration of test compound (i.e. at 3× final desired concentration). As positive controls, set up separate wells using final concentration of 10 µM Wortmannin and/or 50 µM LY-294,002 (inhibitors of PI-3 kinase pathway), and 3 ng/ml Leptomycin B (inhibitor of nuclear export).

Return cells to incubator for 4 hours.

3) After incubation, gently remove the medium and slowly add 100 µl fixation solution (PBS/3.7% formaldehyde/0.3% NP-40: prepare fresh for each assay) containing 2 µg/ml DAPI for counterstaining of DNA. 2 µg/ml Hoechst 33342 can be used as an alternative to DAPI. Incubate at 37° C. for 15 min. Remove fixation solution, and wash plate twice with PBS.

4) After second wash, add 100 µl/well of PBS, and read plate on Cellomics ArrayScan instrument using the Cytoplasm to Nuclei translocation algorithm. In absence of ArrayScan Instrument, conventional fluorescence microscopy or equivalent technologies can be used for reading plates. We use filter sets with the following criteria:

| Staining | ABS max | Emission min | Color |
| --- | --- | --- | --- |
| Hoechst | 346 | 460 | Blue |
| DAPI | 359 | 461 | Blue |
| EGFP | 489 | 506 | Green |

Many compounds of formula (I) of the present invention showed $IC_{50}$ values on AKT-1 in the low micromolar range.

In particular, the compounds coded E11, E12, E14, E15, E21, G9, L6, L9 showed $IC_{50}$ values on AKT-1 below 500 nM.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 1000 mg per dose, from 1 to 10 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim to better illustrate the present invention, without posing any limitation to it, the following examples are now given.

EXAMPLES

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

General Methods

Flash Chromatography was performed on silica gel (Merck grade 9395, 60A). Where specified, chromatographic separations have been performed on a Biotage Horizon system. Microwave-assisted reactions were performed using Biotage/PersonalChemistry SmithCreator™. HPLC was performed on Waters X Terra RP 18 (4.6×50 mm, 3.5 m) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was $H_2O$/acetonitrile (5:95). Gradient from 10 to 90% B in 8 minutes, hold 90% B 2 minutes. UV detection at 220 nm and 254 nm. Flow rate 1 mL/min. Injection volume 10 L. Full scan, mass range from 100 to 800 amu. Capillary voltage was 2.5 KV; source temp, was 120° C.; cone was 10 V. Retention times (HPLC r.t.) are given in minutes at 220 nm or at 254 nm. Mass are given as m/z ratio. When necessary, compounds have been purified by preparative HPLC on a Waters Symmetry C18 (19×50 mm, 5 m) column using a Waters preparative HPLC 600 equipped with a 996 Waters PDA detector and a Micromass mod. ZMD single quadrupole mass spectrometer, electron spray ionization, positive mode. Mobile phase A was water 0.01% TFA, and Mobile phase B was acetonitrile. Gradient from 10 to 90% B in 8 min, hold 90% B 2 min. Flow rate 20 mL/min. Unless differently reported, $^1$H-NMR spectrometry was performed on a Mercury VX 400 operating at 400.45 MHz equipped with a 5 mm double resonance probe [1H (15N-31P) ID_PFG Varian] unless otherwise indicated. Chemical shifts are expressed as δ (ppm), coupling constants (J) are expressed in Hertz and the solvent is DMSO-$d_6$.

In these examples and elsewhere, abbreviations have the following meanings:
AcOH=glacial acetic acid
aq=aqueous
AN=acetonitrile
bd=broad doublet
BINAP=(R)-(+)-2,2'-bis(diphenylphosphino)-1,1'-binaphthyl
BnBr=benzylbromide
Boc=$^t$butoxycarbonyl
bs=broad singlet
bt=broad triplet
conc=concentrated
DCM=dichloromethane
DDQ=o-dichlorodicyanobenzoquinone
DIEA=diisopropylethylamine
DMF=N,N'-dimethylformamide
DMSO=dimethylsulfoxide
DMSO-D6=deuterated dimethylsulfoxide
EDCI=1-(3-dimethylaminopropyl)-3-ethylcarbodiimide hydrochloride
eq=equivalents
ES=electrospray ionization
Et=ethyl
h=hour(s)
HOBT=hydroxybenzotriazole
HOBT.$NH_3$=hydroxybenzotriazole ammonium salt
HPLC=high performance liquid chromatography
Me=methyl
Meldrum's acid=2,2-dimethyl-1,3-dioxane-4,6-dione
min=minutes
mL=milliliters
mmol=millimoles
mol=moles
MW=microwaves irradiation
NaH=sodium hydride, 60% in mineral oil
$Na_2SO_4$=anhydrous sodium sulphate
NBS=N-bromo-succinimide
NCS=N-chloro-succinimide
NIS=N-iodo-succinimide
rt=room temperature
TBAB=tetrabutylammonium bromide
TBTU=O-benzotriazol-1-yl-N,N,N',N'-tetramethyluronium tetrafluoroborate
TEA=triethylamine
TFA=trifluoroacetic acid
THF=tetrahydrofuran
Tr=trityl=triphenylmethyl
pTSA=p-toluenesulphonic acid monohydrate
μL=microliters
μM or uM=micromolar Example 1

7-Trityl-1,4,5,7-tetrahydro-1,6,7-triaza-as-indacene-2,3-dicarboxylic acid 2-tert-butyl ester 3-ethyl ester (V, $R_2$=COOtBu, $R'_3$=COOEt)

To a solution of oxo-(4-oxo-2-trityl-4,5,6,7-tetrahydro-2H-indazol-5-yl)-acetic acid ethyl ester (2.09 mmol) in dry toluene (15 mL), tetrarhodiumdodecacarbonyl (0.02 mmol) and t-butylisocyanoacetate (2.50 mmol) were added. The reaction mixture was heated at 80° C. for 4 h. The solvent was evaporated and the residue was purified by chromatography on silica gel (eluant: hexane/AcOEt 8:2). The title compound was obtained in 40% yield. ESI (+) MS: m/z 574 (MH$^+$). $^1$H NMR: 1.27 (t, J=7.02, 3H), 1.46 (s, 9H), 2.78 (bs, 4H), 4.20 (q, J=7.02, 2H), 7.06-7.16 (m, 6H), 7.33-7.44 (m, 9H), 7.66 (s, 1H), 13.43 (s, 1H).

Example 2

1-Methyl-7-trityl-1,4,5,7-tetrahydro-1,6,7-triaza-as-indacene-2,3-dicarboxylic acid 2-tert-butyl ester 3-ethyl ester (VI, $R_1$=methyl, $R_2$=COOtBu, $R'_3$=COOEt)

To a solution of 7-trityl-1,4,5,7-tetrahydro-1,6,7-triaza-as-indacene-2,3-dicarboxylic acid 2-tert-butyl ester 3-ethyl ester V (0.784 mmol) in dry DMF (15 mL), caesium carbonate (1.57 mmol) and methyl iodide (2.34 mmol) were added. The reaction mixture was heated at 70° C. in a sealed tube for 3 h then the solvent was evaporated. The residue was suspended in DCM, washed with water, dried ($Na_2SO_4$) and concentrated affording the title compound (98% yield). ESI (+) MS: m/z 588 (MH$^+$). $^1$H NMR: 1.28 (t, J=7.07, 3H), 1.48 (s, 9H), 2.78 (bs, 4H), 3.68 (s, 3H), 4.20 (q, J=7.07, 2H), 7.06-7.21 (m, 6H), 7.32-7.45 (m, 9H), 7.59 (s, 1H).

Example 3

1-Methyl-1,4,5,6-tetrahydro-1,6,7-triaza-as-indacene-3-carboxylic acid ethyl ester (A1)

To a mixture of 1-methyl-7-trityl-1,4,5,7-tetrahydro-1,6,7-triaza-as -indacene-2,3-dicarboxylic acid 2-tert-butyl ester 3-ethyl ester VI (2.4 mmol) in EtOH (60 mL), 2N HCl (6 mL) was added and the reaction was heated at 80° C. for 2 h. The solvent was evaporated and the residue was washed twice with DCM/hexane. The title product was obtained as a solid (98% yield). ESI (+) MS: m/z 246 (MH$^+$). $^1$H NMR: 1.27 (t, 3H), 2.78 (t, 2H), 2.97 (dt, 2H), 3.74 (s, 3H), 4.18 (q, 2H), 7.32 (s, 1H), 7.82 (s, 1H).

Example 4

1-Methyl-1,6-dihydro-1,6,7-triaza-as-indacene-2,3-dicarboxylic acid 2-tert-butyl ester 3-ethyl ester (C3)

To a solution of 1-methyl-7-trityl-1,4,5,7-tetrahydro-1,6,7-triaza-as-indacene-2,3-dicarboxylic acid 2-tert-butyl ester 3-ethyl ester VI (1.05 mmol) in 20 mL of dry dioxane under argon, DDQ (1.26 mmol) was added. The dark solution was heated at 100° C. for 4 h then the solvent was evaporated. The residue was dissolved in DCM, washed with water and with 20% aq sodium carbonate. The organic layers were dried (Na$_2$SO$_4$) and evaporated to dryness. The residue was purified by chromatography on silica gel (eluant: hexane/AcOEt 7:3) affording the title compound in 66% yield. ESI (+) MS: m/z 344 (MH$^+$). $^1$H NMR: 1.34 (t, J=7.09, 3H), 1.59 (s, 9H), 4.12 (s, 3H), 4.33 (q, J=7.09, 2H), 7.44 (d, J=9.02, 1H), 7.90 (d, J=9.02, 1H), 8.47 (s, 1H), 13.43 (bs, 1H).

Example 5

1-Methyl-1,6-dihydro-1,6,7-triaza-as-indacene-2,3-dicarboxylic acid 3-ethyl ester (C4)

To a solution of 1-methyl-1,6-dihydro-1,6,7-triaza-as-indacene-2,3-dicarboxylic acid 2-tert-butyl ester 3-ethyl ester C3 (0.68 mmol in DCM (10 mL), trifluoroacetic acid (1 mL) was added. The solution was stirred at rt for 2 h then the reaction mixture was evaporated to dryness affording the title compound in quantitative yield. ESI (+) MS: m/z 288 (MH$^+$); MS (ES$^-$) 286. $^1$H NMR: 1.35 (t, J=7.07, 3H), 4.18 (s, 3H), 4.33 (q, J=7.07, 2H), 7.47 (d, J=9.02, 1H), 7.91 (d, J=9.02, 1H), 8.51 (s, 1H), 13.46 (bs, 2H).

Example 6

1-Methyl-1,6-dihydro-1,6,7-triaza-as-indacene-3-carboxylic acid ethyl ester (B1)

To a mixture of 1-methyl-1,4,5,6-tetrahydro-1,6,7-triaza-as-indacene-3-carboxylic acid ethyl ester A1 (1.65 mmol) in dioxane (45 mL) under argon, DDQ (1.2 eq) was added and the reaction was kept at 100° C. for 2 h. The residue obtained after solvent evaporation was taken up with AcOEt and the organic phase was washed with water, dried (Na$_2$SO$_4$) and concentrated to give a crude product that was purified using the Biotage Horizon system (AcOEt/hexane 2:8). The title product was obtained as a solid (30% yield). ESI (+) MS: m/z 244 (MH$^+$). $^1$H NMR: 1.34 (t, 3H), 4.13 (s, 3H), 4.28 (q, 2H), 7.40 (d, 1H), 7.96 (s, 1H), 8.00 (d, 1H), 8.41 (s, 1H), 13.28 (bs, 1H).

Example 7

Benzyl-1-methyl-tetrahydro-1,6,7-triaza-as-indacene-3-carboxylic acid ethyl esters (VII, Pg=benzyl, R$_1$=methyl, R$_5$=ethyl)

To a solution of 1-methyl-1,4,5,6-tetrahydro-1,6,7-triaza-as-indacene-3-carboxylic acid ethyl ester A1 (2.85 mmol) in 35 mL of DMF, caesium carbonate (3.14 mmol) and benzyl bromide (3.14 mmol) were added. The suspension was stirred at rt for 24 h then the solvent was evaporated. The crude was suspended in DCM and washed with water. The organic phase was dried (Na$_2$SO$_4$) and concentrated. The mixture of regioisomers was chromatographed on silica gel (eluant: AcOEt/hexane 3:7) affording the title products (83% yield).

7-Benzyl-1-methyl-1,4,5,7-tetrahydro-1,6,7-triaza-as-indacene-3-carboxylic acid ethyl ester ESI (+) MS: m/z 336 (MH$^+$); $^1$H NMR: 1.25 (t, J=7.07, 3H), 2.72 (t, J=7.80, 2H), 2.94 (t, J=7.80, 2H), 3.71 (s, 3H), 4.15 (q, J=7.07, 2H), 5.26 (s, 2H), 7.25-7.39 (m, 6H), 7.97 (s, 1H).

6-Benzyl-1-methyl-1,4,5,6-tetrahydro-1,6,7-triaza-as-indacene-3-carboxylic acid ethyl ester ESI (+) MS: m/z 336 (MH$^+$).

Example 8

Benzyl-1-methyl-dihydro-1,6,7-triaza-as-indacene-3-carboxylic acid ethyl esters (VIII, Pg=benzyl, R$_1$=methyl, R$_5$=ethyl)

To a solution of the regioisomeric mixture of benzyl-1-methyl-tetrahydro-1,6,7-triaza-as-indacene-3-carboxylic acid ethyl esters VII (2.35 mmol) in 20 mL of dry dioxane under argon, DDQ (2.83 mmol) was added. The dark solution was heated at 100° C. for 30 min then the solvent was evaporated. The solid residue was dissolved in DCM, washed with water and with 20% aq sodium carbonate, dried (Na$_2$SO$_4$) and concentrated to dryness. Purification of the mixture of regioisomers by chromatography on silica gel (eluant: hexane/AcOEt 7:3) afforded the title compounds (89% yield).

7-Benzyl-1-methyl-1,7-dihydro-1,6,7-triaza-as-indacene-3-carboxylic acid ethyl ester ESI (+) MS: m/z 334 (MH$^+$); $^1$H NMR: 1.33 (t, J=7.07, 3H), 4.06 (s, 3H), 5.66 (s, 2H), 4.27 (q, J=7.07, 2H), 7.27-7.40 (m, 6H), 7.90 (s, 1H), 7.90 (d, J=9.27, 1H), 8.84 (s, 1H).

6-Benzyl-1-methyl-1,6-dihydro-1,6,7-triaza-as-indacene-3-carboxylic acid ethyl ester ESI (+) MS: m/z 334 (MH$^+$).

Example 9

7-Benzyl-1-methyl-1,7-dihydro-1,6,7-triaza-as-indacene-3-carboxylic acid and 6-benzyl-1-methyl-1,6-dihydro-1,6,7-triaza-as-indacene-3-carboxylic acid (IX, Pg=benzyl, R$_1$=methyl, R$_5$=H)

To a solution of the regioisomeric mixture of benzyl-1-methyl-tetrahydro-1,6,7-triaza-as-indacene-3-carboxylic acid ethyl esters VIII (2.05 mmol) in 95% EtOH (20 mL), KOH (5 eq) was added. The solution was heated to reflux for 12 h then was cooled to rt and the solvent was evaporated. The residue was dissolved in 20 mL of water and the solution was acidified to pH 2 with 2N HCl. The precipitate was filtered, washed with water, dried (Na$_2$SO$_4$) and concentrated affording the title regioisomers as a mixture (95% yield). ESI (+) MS: m/z 306 (MH$^+$); MS (ES$^-$) 304.

Employing the same methodology but starting from the suitable ester B1, the following compound was obtained:

1-Methyl-1,6-dihydro-1,6,7-triaza-as-indacene-3-carboxylic acid (B2)

ESI (+) MS: m/z 216 (MH$^+$); MS (ES$^-$) 214. $^1$H NMR: 4.12 (s, 3H), 7.35 (d, J=8.90, 1H), 7.89 (s, 1H), 8.03 (d, J=8.90, 1H), 8.40 (s, 1H), 11.94 (bs, 1H), 13.25 (bs, 1H).

Example 10

Benzyl-1-methyl-dihydro-1,6,7-triaza-as-indacene-3-carboxylic acid amides (X, Pg=benzyl, R$_1$=methyl, R$_5$=H)

To a solution of the regioisomeric mixture of benzyl-1-methyl-dihydro-1,6,7-triaza-as-indacene-3-carboxylic acids IX (1.74 mmol) in dry DMF (20 mL), HOBT.NH$_3$ (3.48 mmol), TBTU (3.48 mmol) and DIEA (1.1 mL) were added. The mixture was stirred at rt for 24 h, concentrated, suspended in 20 mL of 10% aq Na$_2$CO$_3$ and extracted with DCM. The organic layers were collected, dried (Na$_2$SO$_4$) and evaporated to dryness. Chromatography on silica gel (eluant: DCM/MeOH 20:1) afforded the title compounds (85% yield).

6-Benzyl-1-methyl-1,6-dihydro-1,6,7-triaza-as-indacene-3-carboxylic acid amide

ESI (+) MS: m/z 305 (MH$^+$); $^1$H NMR: 4.08 (s, 3H), 5.72 (s, 2H), 6.82 (bs, 2H), 7.18-7.31 (m, 5H), 7.43 (d, J=9.0, 1H), 7.86 (s, 1H), 8.18 (d, J=9.0, 1H), 8.44 (s, 1H).

7-Benzyl-1-methyl-1,7-dihydro-1,6,7-triaza-as-indacene-3-carboxylic acid amide

ESI (+) MS: m/z 305 (MH$^+$).

Example 11

1-Methyl-1,7-dihydro-1,6,7-triaza-as-indacene-3-carboxylic acid amide (B3)

To a solution of the regioisomeric mixture of benzyl-1-methyl-dihydro-1,6,7-triaza-as-indacene-3-carboxylic acid amides X (1.64 mmol) in dry DMSO (1 mL), 1M potassium tert-butoxide (11.5 mmol) in THF was added. The solution was bubbled with dry air for 5 h. Chromatography on silica gel (eluant: DCM/MeOH 20:1) afforded the title compound (70% yield). ESI (+) MS: m/z 215 (MH$^+$). $^1$H NMR: 4.08 (s, 3H), 7.05 (bs, 2H), 7.28 (d, J=8.90, 1H), 7.83 (s, 1H), 8.17 (d, J=8.90, 1H), 8.38 (s, 1H), 13.19 (bs, 1H).

Example 12

1-Methyl-1,7-dihydro-1,6,7-triaza-as-indacene-3-carboxylic acid amide (B3)

To a solution of 1-methyl-1,6-dihydro-1,6,7-triaza-as-indacene-3-carboxylic acid B2 (0.232 mmol) dry DMF (2 mL), HOBT.NH$_3$ (0.464 mmol), TBTU (0.464 mmol) and DIEA (0.08 mL) were added. The mixture was stirred at rt for 24 h. The reaction mixture was concentrated and the residue was chromatographed on silica gel (eluant: DCM/MeOH 20:1). The title compound was obtained in 60% yield.

Example 13

5-Bromo-2,5,6,7-tetrahydro-indazol-4-one (2B)

To a solution of 2,5,6,7-tetrahydro-indazol-4-one (5.28 mmol), optionally protected as the trityl derivative, in Et$_2$O (20 mL) and AcOH (15 mL), at 0° C., a solution of Br$_2$ (10.56 mmol) in AcOH (20 mL) was slowly added dropwise. The solution was then heated at 60° C. for 1h then the organic solvents were evaporated to dryness and the white precipitate was suspended in Et$_2$O, filtered and dried. The title compound was obtained in 80% yield. ESI (+) MS: m/z 216 (MH$^+$).

Example 14

Benzyl-5-bromo-tetrahydro-indazol-4-ones (2C)

To a solution of 5-bromo-2,5,6,7-tetrahydro-indazol-4-one 2B (9.8 mmol) in 20 mL of dry dimethylformamide under argon, caesium carbonate (14.7 mmol) and benzylbromide (14.7 mmol) were added. The reaction mixture was stirred for 12 h then the white solid was removed by filtration and the solution obtained was used in the next step without purification. ESI (+) MS: m/z 216 (MH$^+$).

Example 15

(Benzyl-4-oxo-tetrahydro-indazol-5-yl)-cyano-acetic acid ethyl esters (2D)

To a solution of benzyl-5-bromo-tetrahydro-indazol-4-ones 2C (9.8 mmol) in DMF (20 mL), ethyl cyanoacetate (78.4 mmol) and potassium carbonate (19.6 mmol) were added. The reaction mixture was heated at 50° C. for 3 h then the solvent was evaporated. The residue was dissolved in ethyl acetate, washed with 20% aq NaH$_2$PO$_4$, dried (Na$_2$SO$_4$) and evaporated to dryness. Purification by chromatography (eluant: hexane/AcOEt 3:7) afforded 2 g of the title compounds (60% yield). ESI (+) MS: m/z 338 (MH$^+$).

Example 16

Benzyl-2-chloro-tetrahydro-1,6,7-triaza-as-indacene-3-carboxylic acid ethyl esters (XI, Pg=benzyl, R$_2$=chloro, R$_5$=ethyl)

To a solution of (benzyl-4-oxo-tetrahydro-indazol-5-yl)-cyano-acetic acid ethyl esters 2D (5.9 mmol) in 5 mL of dry dioxane, 20 mL of 4M HCl in dioxane were added. The reaction mixture was stirred for 8 h. Nitrogen was then bubbled into the mixture then the solvent was evaporated. The residue was dissolved in ethylacetate, washed with water, dried (Na$_2$SO$_4$) and evaporated to dryness. Purification by chromatography (eluant: hexane/AcOEt 1:1) afforded the title compounds in 48% yield. ESI (+) MS: m/z 356 (MH$^+$).

Example 17

Benzyl-2-chloro-1-methyl-tetrahydro-1,6,7-triaza-as-indacene-3-carboxylic acid ethyl esters (XII, Pg=benzyl, R$_1$=methyl, R$_2$=chloro, R$_5$=ethyl)

To a solution of benzyl-2-chloro-tetrahydro-1,6,7-triaza-as-indacene-3-carboxylic acid ethyl ester XI (1.4 mmol) in dry THF (10 mL), caesium carbonate (4.2 mmol) and methyl iodide (2.1 mmol) were added. The reaction mixture was heated at 60° C. in a sealed tube for 3 h then the solvent was evaporated. The residue was suspended in AcOEt, washed with water, dried (Na$_2$SO$_4$) and concentrated affording the title compounds (yield: quantitative). Purification of the mixture of regioisomers by chromatography on silica gel (eluant: hexane/AcOEt 4:1) afforded the title compounds.

7-Benzyl-2-chloro-1-methyl-1,4,5,7-tetrahydro-1,6, 7-triaza-as-indacene-3-carboxylic acid ethyl ester ESI (+) MS: m/z 370 (MH$^+$); $^1$H NMR: 1.28 (t, J=7.07, 3H), 2.74 (t, J=7.80, 2H), 2.95 (t, J=7.80, 2H), 3.67 (s, 3H), 4.20 (q, J=7.07, 2H), 5.26 (s, 2H), 7.24-7.38 (m, 5H), 8.07 (s, 1H).

6-Benzyl-2-chloro-1-methyl-1,4,5,6-tetrahydro-1,6, 7-triaza-as-indacene-3-carboxylic acid ethyl ester ESI (+) MS: m/z 370 (MH$^+$); $^1$H NMR: 1.27 (t, J=7.07, 3H), 2.84 (t, J=7.80, 2H), 2.97 (t, J=7.80, 2H), 3.72 (s, 3H), 4.19 (q, J=7.07, 2H), 5.34 (s, 2H), 7.13-7.36 (m, 5H), 7.74 (s, 1H).

Example 18

Benzyl-2-chloro-1-methyl-dihydro-1,6,7-triaza-as-indacene-3-carboxylic acid ethyl esters (XIII, Pg=benzyl, R$_1$=methyl, R$_2$=chloro, R$_5$=ethyl)

To a solution of the regioisomeric mixture of benzyl-2-chloro-1-methyl-tetrahydro -1,6,7-triaza-as-indacene-3-carboxylic acid ethyl ester XII (0.42 mmol) in 10 mL of dry dioxane under argon, DDQ (0.50 mmol) was added. The solution was heated at 100° C. for 30 min then the solvent was evaporated. The solid residue was dissolved in AcOEt, washed with water and with 20% aq sodium carbonate, dried (Na$_2$SO$_4$) and concentrated to dryness. Purification of the mixture of regioisomers by chromatography on silica gel (eluant: hexane/AcOEt 8:2) afforded the title compounds (71% yield).

7-Benzyl-2-chloro-1-methyl-1,7-dihydro-1,6,7-triaza-as-indacene-3-carboxylic acid ethyl ester ESI (+) MS: m/z 368 (MH$^+$); $^1$H NMR: 1.37 (t, J=7.07, 3H), 4.03 (s, 3H), 4.33 (q, J=7.07, 2H), 5.66 (s, 2H), 7.21-7.39 (m, 5H), 7.43 (d, J=9.15, 1H), 7.93 (d, J=9.15, 1H), 8.95 (s, 1H).

6-Benzyl-2-chloro-1-methyl-1,6-dihydro-1,6,7-triaza-as-indacene-3-carboxylic acid ethyl ester ESI (+) MS: m/z 368 (MH$^+$); $^1$H NMR: 1.37 (t, J=7.07, 3H), 4.09 (s, 3H), 4.33 (q, J=7.07, 2H), 5.74 (s, 2H), 7.19-7.32 (m, 5H), 7.59 (d, J=9.02, 1H), 8.04 (d, J=9.02, 1H), 8.53 (s, 1H).

Example 19

Benzyl-2-chloro-1-methyl-dihydro-1,6,7-triaza-as-indacene-3-carboxylic acids (XIV, Pg=benzyl, R$_1$=methyl, R$_2$=chloro)

To a solution of benzyl-2-chloro-1-methyl-dihydro-1,6,7-triaza-as-indacene -3-carboxylic acid ethyl esters XIII (2.11 mmol) in 95% EtOH (20 mL) KOH (3.89 mmol) was added. The solution was heated to reflux for 18 h then it was cooled to rt and the solvent was evaporated. The residue was dissolved in 20 mL of water and the solution was washed with dichloromethane. The water solution was acidified to pH 2 with 2N HCl. The precipitate was filtered, washed with water and dried, affording the title compounds (60% yield). ESI (+) MS: m/z 340 (MH$^+$); MS (ES$^-$) 338.

Example 20

Benzyl-2-chloro-1-methyl-dihydro-1,6,7-triaza-as-indacene-3-carboxylic acid amides (XV, Pg=benzyl, R$_1$=methyl, R$_2$=chloro, R$_5$=H)

To a solution of benzyl-2-chloro-1-methyl-dihydro-1,6,7-triaza-as-indacene -3-carboxylic acids XIV (0.29 mmol) in dry DMF (10 mL), HOBT.NH$_3$ (0.59 mmol), TBTU (0.59 mmol) and DIEA (0.2 mL) were added. The mixture was stirred at rt for 24 h. The reaction mixture was concentrated and the residue was suspended in dichloromethane and washed with Na$_2$CO$_3$ solution. The organic phase was dried (Na$_2$SO$_4$) and evaporated to dryness, affording the title compounds (92% yield). Chromatography (eluant: hexane/AcOEt 8:2) afforded the title compounds (78% yield).

7-Benzyl-2-chloro-1-methyl-1,7-dihydro-1,6,7-triaza-as-indacene-3-carboxylic acid amide ESI (+) MS: m/z 339.

6-Benzyl-2-chloro-1-methyl-1,6-dihydro-1,6,7-triaza-as-indacene-3-carboxylic acid amide ESI (+) MS: m/z 339; $^1$H NMR: 4.06 (s, 3H), 5.73 (s, 2H), 7.18-7.31 (m, 5H), 7.37 (bs, 2H), 7.50 (d, J=8.96, 1H), 7.97 (d, J=8.96, 1H), 8.51 (s, 1H).

Example 21

2-Chloro-1-methyl-1,6-dihydro-1,6,7-triaza-as-indacene-3-carboxylic acid amide (C1)

To a solution of benzyl-2-chloro-1-methyl-dihydro-1,6,7-triaza-as-indacene -3-carboxylic acid amides XV (0.9 mmol) in dry DMSO (0.2 mL) 1M potassium tert-butoxide (1.85 mmol) in THF was added. The solution was bubbled with dry air for 2 h. Chromatography (eluant: DCM/MeOH 23:2) afforded the title compound (78% yield). ESI (+) MS: m/z 249 (MH$^+$). $^1$H NMR: 4.07 (s, 3H), 7.20 (bs, 2H), 7.36 (d, J=8.90, 1H), 7.90 (d, J=8.90, 1H), 8.47 (s, 1H), 13.31 (bs, 1H).

Example 22

Benzyl-1-methyl-2-phenyl-dihydro-1,6,7-triaza-as-indacene-3-carboxylic acid amides (XVI, Pg=benzyl, R$_1$=methyl, R$_2$=phenyl, R$_5$=H)

A suspension of benzyl-2-chloro-1-methyl-dihydro-1,6,7-triaza-as-indacene-3-carboxylic acid amides XV (0.41 mmol), Na$_2$CO$_3$ (1.52 mmol), 5% Pd/C (0.041 mmol), TBAB (0.41 mmol) and phenylboronic acid (0.54 mmol) in water (4 mL) was heated at 120° C. (simultaneous cooling) for 40 min with microwave irradiation. After evaporation to dryness, the residue was purified by chromatography on silica gel (eluant: DCM/MeOH 98:2) affording the title compound (36% yield). ESI (+) MS: m/z 381 (MH$^+$). $^1$H NMR: 3.74 (s, 3H), 5.5 (s, 2H) 6.00 (bs, 1H) 6.80 (bs, 1H), 7.30-7.80 (m, 10H), 8.77 (s, 1H).

Example 23

1-Methyl-2-phenyl-1,7-dihydro-1,6,7-triaza-as-indacene-3-carboxylic acid amide (C2)

To a solution of benzyl-1-methyl-2-phenyl-dihydro-1,6,7-triaza-as-indacene -3-carboxylic acid amides XVI (0.118 mmol) in dry DMSO (0.1 mL), 1M potassium tert-butoxide (0.83 mmol) in THF was added. The solution was bubbled with dry air for 10 min. Volatiles were removed, the residue was suspended in DCM, washed with water, dried ($Na_2SO_4$), filtered and the solvent evaporated. Chromatography on silica gel (eluant: DCM/MeOH 95:5) afforded the desired compound (70% yield). ESI (+) MS: m/z 291 ($MH^+$). $^1H$ NMR: 3.82 (s, 3H), 6.02 (bs, 1H), 6.95 (bs, 1H), 7.34 (dd, J=8.90, 0.73, 1H), 7.51-7.65 (m, 5H), 8.03 (d, J=8.90, 1H), 8.41 (s, 1H), 13.24 (bs, 1H).

Example 24

2-Trityl-2,5,6,7-tetrahydro-indazol-4-one oxime (3B)

To a solution of 2-trityl-2,5,6,7-tetrahydro-indazol-4-one (1.32 mmol) in ethanol (5 mL) and pyridine (0.16 mL), hydroxylamine hydrochloride (1.2 eq) was added and the mixture was stirred at 55° C. for 1.5 h. After cooling to rt, the mixture was diluted with water and filtered. The solid was washed with water and dried. Obtained the title compound in 90% yield. ESI (+) MS: m/z 394 ($MH^+$). $^1H$ NMR: 1.69-1.88 (m, 2H), 2.07-2.25 (m, 2H), 2.59-2.67 (m, 1H), 2.77-2.86 (m, 1H), 6.99 (s, 1H), 7.19-7.31 (m, 15H), 9.94 (s, 1H).

Example 25

3-[2-Trityl-2,5,6,7-tetrahydro-indazol-(4E)-ylidene-aminooxy]-acrylic acid methyl ester (3C)

To a solution of 2-trityl-2,5,6,7-tetrahydro-indazol-4-one oxime 3B (0.51 mmol) in dry DMSO (1 mL) and a catalytic amount of pyridine, methylpropiolate (1.1 eq) was added and the reaction mixture was stirred at rt for 1.5 h. The mixture was poured into water and the slurry was extracted with AcOEt. The organic layer was washed with brine, dried ($Na_2SO_4$) and concentrated to yield the title compound (94%). ESI (+) MS: m/z 478 ($MH^+$). $^1H$ NMR: 1.73-1.93 (m, 2H), 2.10-2.28 (m, 2H), 2.52-2.60 (m, 1H), 2.71-2.79 (m, 1H), 3.83 (s, 3H), 5.40 (d, J=12, 1H), 7.03 (s, 1H), 7.20-7.31 (m, 15H), 8.50 (d, J=12, 1H).

Example 26

7-Trityl-1,4,5,7-tetrahydro-1,6,7-triaza-as-indacene-2-carboxylic acid methyl ester (XVII, Pg=Trityl, $R_2$=COOMe)

3-[2-Trityl-2,5,6,7-tetrahydro-indazol-(4E)-ylideneaminooxy]-acrylic acid methyl ester 3C (6.8 mmol) was heated at 150° C. with stirring under argon for 15 h. The crude material was chromatographed on silica gel (eluant: hexane/AcOEt 7:3) providing the title compound in 20% yield. ESI (+) MS: m/z 460 ($MH^+$). $^1H$ NMR (300 MHz): 2.50-2.92 (m, 4H), 3.80 (s, 3H), 6.53 (s, 1H), 7.11-7.31 (m, 15H), 7.83 (s, 1H), 11.82 (s, 1H).

Example 27

1-Methyl-7-trityl-1,4,5,7-tetrahydro-1,6,7-triaza-as-indacene-2-carboxylic acid methyl ester (XVIII, Pg=trityl, $R_1$=methyl, $R_2$=COOMe)

To a solution of 7-trityl-1,4,5,7-tetrahydro-1,6,7-triaza-as-indacene-2-carboxylic acid methyl ester XVII (1.1 mmol) in dry DMF (5 mL), NaH (2 eq) was added, the mixture was stirred at rt for 15 min then methyl iodide (2 eq) was added and the mixture was stirred at rt for 2 h. The mixture was poured into aq saturated $NaH_2PO_4$, extracted with AcOEt and the organic layer washed with water, dried ($Na_2SO_4$) and concentrated. The crude material was triturated with ethanol and filtered. Obtained the title compound (76% yield). ESI (+) MS: m/z 474 ($MH^+$). $^1H$ NMR (300 MHz): 2.48-2.59 (m, 1H), 2.62-2.92 (m, 3H), 3.79 (s, 3H), 3.89 (s, 3H), 6.44 (s, 1H), 7.11-7.31 (m, 15H), 7.61 (s, 1H).

Example 28

1-Methyl-1,4,5,6-tetrahydro-1,6,7-triaza-as-indacene-2-carboxylic acid methyl ester (A2)

1-Methyl-7-trityl-1,4,5,7-tetrahydro-1,6,7-triaza-as-indacene-2-carboxylic acid methyl ester XVIII (0.74 mmol) was suspended in 3% HCl in MeOH (7 mL) and the mixture was stirred at rt for 4 h. After solvent removal the crude material was chromatographed on silica gel (eluant: AcOEt/hexane 1:1, then AcOEt and AcOEt/MeOH 4:1). Obtained the title compound in 80% yield. ESI (+) MS: m/z 232 ($MH^+$). $^1H$ NMR: 2.80 (m, 2H), 2.94 (m, 2H), 3.79 (s, 3H), 3.88 (s, 3H), 6.82 (s, 1H), 7.76 (s, 1H).

Example 29

1-Methyl-1,6-dihydro-1,6,7-triaza-as-indacene-2-carboxylic acid methyl ester (D1)

A mixture of 1-methyl-1,4,5,6-tetrahydro-1,6,7-triaza-as-indacene-2-carboxylic acid methyl ester A2 (1.03 mmol) and DDQ (1 eq) in dry dioxane (15 mL) was refluxed for 1.5 h with stirring. After solvent removal the slurry was treated with water under vigorous stirring. The precipitate was filtered, washed with water and dried. Obtained the title compound (67%). ESI (+) MS: m/z 230 ($MH^+$). $^1H$ NMR (300 MHz): 3.89 (s, 3H), 4.34 (s, 3H), 7.17 (d, J=8.71, 1H), 7.26 (s, 1H), 7.28 (d, J=8.71, 1H), 8.38 (s, 1H), 13.32 (s, 1H).

Example 30

1-Methyl-1,6-dihydro-1,6,7-triaza-as-indacene-2-carboxylic acid (D2)

1-Methyl-1,6-dihydro-1,6,7-triaza-as-indacene-2-carboxylic acid methyl ester D1 (0.67 mmol) was dissolved in 2N sodium hydroxide in MeOH and refluxed for 2.5 h. After solvent removal the slurry was treated with excess 2N hydrochloric acid under vigorous stirring. The precipitate was filtered, washed with water and dried. Obtained the title compound (97%). ESI (+) MS: m/z 216 ($MH^+$); MS ($ES^-$) 214. $^1H$ NMR: 4.35 (s, 3H), 7.30 (d, J=9.75, 1H), 7.34 (s, 1H), 7.58 (d, J=8.90, 1H), 8.49 (s, 1H), 12.61 (bs, 1H), 13.36 (bs, 1H).

Example 31

1-Methyl-1,6-dihydro-1,6,7-triaza-as-indacene-2-carboxylic acid amide (D3)

To a solution of 1-methyl-1,6-dihydro-1,6,7-triaza-as-indacene-2-carboxylic acid D2 (0.46 mmol) in dry acetonitrile (6 mL) and triethylamine (0.13 mL), first TBTU (2 eq) and, after 10 min, 30% aq ammonium hydroxide solution (2 eq) were added under stirring at rt. After 2 h at rt, the mixture was poured into water and the slurry was extracted with AcOEt. The organic layer was washed with brine, dried ($Na_2SO_4$) and concentrated to yield a crude product that was purified by chromatography on silica gel (eluant: MeOH/DCM 1:9). Obtained the title compound (10%). ESI (+) MS: m/z 215 ($MH^+$). $^1$H NMR: 4.36 (s, 3H), 6.95 (bs, 2H), 7.29 (s, 1H), 7.31 (d, J=8.73, 1H), 7.58 (d, J=8.73, 1H), 8.73 (s, 1H), 13.32 (s, 1H).

Example 32

N-Benzhydrylidene-N'-isoquinolin-5-yl-hydrazine (4A)

To a suspension of 5-bromoisoquinoline (32 mmol), benzophenone hydrazone (32 mmol), BINAP (0.32 mmol) and palladium acetate (0.32 mmol) in dry and degassed toluene (15 mL), sodium tert-butoxide (44.9 mmol) was added together with 16 mL of dry, degassed toluene. The mixture was heated at 80° C. for 4 h, cooled to rt and filtered through a celite pad, rinsing with diethyl ether. The crude product was purified by semi-automatic liquid chromatography on silica gel (eluant: hexane/AcOEt 7:3) affording the title compound (65% yield). ESI (+) MS: m/z 324 ($MH^+$). $^1$H NMR: 7.36 (d, J=6.10, 1H), 7.38-7.45 (m, 2H), 7.48-7.53 (m, 2H), 7.58 (m, 8H), 7.88 (d, J=6.34, 1H), 8.39 (d, J=5.97, 1H), 8.76 (s, 1H), 9.24 (s, 1H).

Example 33

2-Phenyl-1H-pyrrolo[2,3-f]isoquinoline (XIXA, $R_2$=phenyl)

To a solution of N-benzhydrylidene-N'-isoquinolin-5-yl-hydrazine 4A (1.4 mmol) and acetophenone (2.1 mmol) in EtOH (7 mL), pTSA (5.6 mmol) was added and the mixture was submitted to microwaves at 120° C. for 1 h. The solvent was removed, the residue was dissolved in DCM and washed with aq saturated $NaHCO_3$. The organic layer was dried ($Na_2SO_4$) and concentrated. The crude material was then purified by chromatography on silica gel (eluant: hexane/AcOEt 4:6) affording the title compound (58% yield). ESI (+) MS: m/z 245 ($MH^+$). $^1$H NMR (500 MHz): 7.16 (d, J=2.20, 1H), 7.37 (t, J=7.45, 1H), 7.53 (t, J=7.81, 2H), 7.63 (d, J=8.79, 1H), 7.83 (d, J=8.79, 1H), 8.00 (d, J=7.32, 2H), 8.44 (d, J=5.62, 1H), 8.56 (d, J=5.62, 1H), 9.22 (bs, 1H), 12.40 (bs, 1H).

By working in an analogous way and starting from the proper (Het)arylethanones the following compounds were prepared:

2-(4-Bromo-phenyl)-1H-pyrrolo[2,3-f]isoquinoline (XIXB, $R_2$=4-bromo-phenyl)

ESI (+) MS: m/z 324 ($MH^+$). $^1$H NMR: 7.43 (d, J=2.07, 1H), 7.78-7.83 (m, 2H), 8.00-8.05 (m, 2H), 8.17 (d, J=8.66, 1H), 8.74 (d, J=6.58, 1H), 8.91 (d, J=6.58, 1H), 9.68 (s, 1H), 13.02 (s, 1H).

2-Pyridin-4-yl-1H-pyrrolo[2,3-f]isoquinoline (XIXC, $R_2$=pyridin-4-yl)

ESI (+) MS: m/z 246 ($MH^+$). $^1$H NMR: 7.42 (s, 1H), 7.65 (d, J=8.66, 1H), 7.86 (d, J=8.66, 1H), 7.99 (d, J=6.10, 2H), 8.48 (d, J=5.73, 1H), 8.60 (d, J=5.73, 1H), 8.67 (d, J=6.22, 2H), 9.25 (s, 1H), 12.82 (bs, 1H).

Example 34

2-[4-(4-Methyl-piperazin-1-yl)-phenyl]-1H-pyrrolo[2,3-f]isoquinoline (XXA, $R_2$=4-methyl-piperazin-1-yl-phenyl)

To 2-(4-bromo-phenyl)-1H-pyrrolo[2,3-f]isoquinoline XIXB (1.54 mmol), 2-(dicyclohexylphosphino)biphenyl (0.154 mmol), palladium acetate (0.154 mmol) and 1-methylpiperazine (15.46 mmol), degassed DMF (5 mL) and sodium tert-butoxide (4.62 mmol) were added. The mixture was submitted to microwaves at 150° C. for 15 min, the solvent was removed and the crude was purified by chromatography on silica gel (eluant: DCM/MeOH/30% aq $NH_3$ 92:8:1) affording the title compound (79% yield). ESI (+) MS: m/z 343 ($MH^+$). $^1$H NMR: 2.24 (s, 3H), 2.45-2.50 (m, 4H), 3.20-3.26 (m, 4H), 6.96 (d, J=1.46, 1H), 7.07 (d, J=8.90, 2H), 7.58 (d, J=8.54, 1H), 7.78 (d, J=8.54, 1H), 7.85 (d, J=8.90, 2H), 8.43 (d, J=5.85, 1H), 8.50 (d, J=5.73, 1H), 9.18 (s, 1H), 12.33 (s, 1H).

By working in an analogous way and employing morpholine, the following compound was prepared:

2-(4-Morpholin-4-yl-phenyl)-1H-pyrrolo[2,3-f]isoquinoline (XXB, $R_2$=4-morpholin-4-yl-phenyl)

ESI (+) MS: m/z 330 ($MH^+$). $^1$H NMR: 3.20-3.25 (m, 4H), 3.75-3.80 (m, 4H), 7.06 (d, J=2.07, 1H), 7.10 (d, J=8.90, 2H), 7.71 (d, J=8.66, 1H), 7.89 (d, J=8.90, 3H), 8.52-8.61 (m, 2H), 9.33 (s, 1H), 12.41 (s, 1H).

Example 35

2-Phenyl-1H-pyrrolo[2,3-f]isoquinoline-3-carbaldehyde (G1)

To a solution of 2-phenyl-1H-pyrrolo[2,3-f]isoquinoline XIXA (2.75 mmol) in DCM (13 mL) and nitromethane (13 mL), cooled to 0° C., aluminum chloride (8.25 mmol) and dichloromethylmethylether (5.5 mmol) were added dropwise. The mixture was kept at 4° C. overnight and poured dropwise into stirred ice-cooled water. The solid product was filtered and the layers were separated. The aqueous layer was extracted with DCM and AcOEt. The combined organic layers, washed with water, dried ($Na_2SO_4$) and concentrated, were joined to the previously described solid affording the title compound in 51% yield. ESI (+) MS: m/z 273 ($MH^+$). $^1$H NMR: 7.66-7.71 (m, 3H), 7.91-7.96 (m, 2H), 8.19 (d, J=8.79, 1H), 8.71 (d, J=8.55, 1H), 8.79 (d, J=6.35, 1H), 8.93 (d, J=6.35, 1H), 9.77 (s, 1H), 10.12 (s, 1H), 13.80 (bs, 1H).

By working in an analogous way and starting from the proper pyrroloisoquinolines, respectively XIXB, XXB and XIXC, the following aldehydes were prepared:

2-(4-Bromo-phenyl)-1H-pyrrolo[2,3-f]isoquinoline-3-carbaldehyde (G4)

ESI (+) MS: m/z 352 ($MH^+$). $^1$H NMR: 7.89 (s, 4H), 8.16 (d, J=8.79, 1H), 8.68 (d, J=8.79, 1H), 8.78 (d, J=6.15, 1H), 8.83 (d, J=6.45, 1H), 9.71 (s, 1H), 10.12 (s, 1H), 13.72 (s, 1H).

2-(4-Morpholin-4-yl-phenyl)-1H-pyrrolo[2,3-f]iso-quinoline -3-carbaldehyde (G7)

ESI (+) MS: m/z 358 (MH+). $^1$H NMR: 3.25-3.34 (m, 4H), 3.73-3.83 (m, 4H), 7.18 (d, J=8.90, 2H), 7.75 (d, J=8.78, 2H), 7.85 (d, J=8.66, 1H), 8.45 (d, J=8.66, 1H), 8.46 (d, J=5.49, 1H), 8.59 (d, J=5.85, 1H), 9.31 (s, 1H), 10.06 (s, 1H), 13.09 (bs, 1H).

2-Pyridin-4-yl-1H-pyrrolo[2,3-f]isoquinoline-3-car-baldehyde (H1)

ESI (+) MS: m/z 274 (MH+). $^1$H NMR: 7.90 (d, J=5.98, 2H), 7.92 (d, J=8.40, 1H), 8.43 (d, J=5.73, 1H), 8.48 (d, J=8.78, 1H), 8.66 (d, J=5.73, 1H), 8.84 (d, J=5.73, 2H), 9.36 (s, 1H), 10.16 (s, 1H), 13.45 (bs, 1H).

Example 36

2-Phenyl-1H-pyrrolo[2,3-f]isoquinoline-3-carboxylic acid (G2)

To a suspension of 2-phenyl-1H-pyrrolo[2,3-f]isoquinoline-3-carbaldehyde G1 (0.55 mmol) in dioxane (6.8 mL) and water (2.4 mL), sulfamic acid (0.9 mmol) and sodium dihydrogen phosphate (2.33 mmol) were added. The mixture was cooled to 0° C. and sodium chlorite (0.95 mmol, dissolved in the minimum amount of water) was added. Other two additions of an equal amount of oxidant were made during 24 h of stirring, then the reaction was filtered and the solid product was washed with water and dried, resulting in 94% yield of the title compound. ESI (+) MS: m/z 289 (MH+); MS (ES−) 287. $^1$H NMR: 7.35-7.41 (m, 1H), 7.45-7.56 (m, 4H), 7.96 (d, J=9.00, 1H), 8.58 (d, J=9.00, 1H), 8.68 (d, J=5.17, 1H), 8.78 (d, J=5.17, 1H), 9.57 (s, 1H), 11.47 (bs, 1H), 13.54 (bs, 1H).

By working in an analogous way and starting from the appropriate aldehydes, respectively G4 and H1, the following acids were prepared:

2-(4-Bromo-phenyl)-1H-pyrrolo[2,3-f]isoquinoline-3-carboxylic acid (G5)

ESI (+) MS: m/z 368 (MH+); MS (ES−) 366. $^1$H NMR: 7.74-7.83 (m, 4H), 8.13 (d, J=8.90, 1H), 8.63 (d, J=8.90, 1H), 8.77 (d, J=6.46, 1H), 8.86 (d, J=6.46, 1H), 9.74 (s, 1H), 13.53 (s, 1H).

2-Pyridin-4-yl-1H-pyrrolo[2,3-f]isoquinoline-3-carboxylic acid (H2)

ESI (+) MS: m/z 290 (MH+); MS (ES−) 288. $^1$H NMR: 7.59 (d, J=5.51, 2H), 7.96 (d, J=9.00, 1H), 8.58 (d, J=9.00, 1H), 8.60 (d, J=5.51, 2H), 8.68 (d, J=5.17, 1H), 8.78 (d, J=5.17, 1H), 9.57 (s, 1H), 11.47 (bs, 1H), 13.54 (bs, 1H).

Example 37

2-Phenyl-1H-pyrrolo[2,3-f]isoquinoline-3-carboxylic acid amide (G3)

To a suspension of 2-phenyl-1H-pyrrolo[2,3-f]isoquinoline-3-carboxylic acid G2 (0.25 mmol) in THF (3 mL), DIEA (0.75 mmol) was added. The mixture was cooled to 0° C., EDCI hydrochloride (0.38 mmol) and HOBT.NH$_3$ (0.38 mmol) were added and stirring at rt was maintained overnight. Ethylacetate and water were added, the layers were separated, the aqueous layer was extracted with ethylacetate and the combined organic layers were washed with water and with 1N NaOH. They were then dried (Na$_2$SO$_4$), filtered and evaporated. Treatment with a small amount of methanol caused precipitation of the product, which was filtered affording the title compound. The amide was suspended in methanol and treated with 4M HCl in dioxane until pH was 1. Solvent was removed, the residue was treated with diethylether and the resulting solid was filtered, washed with diethylether and dried, affording the hydrochloric salt of the title compound (43% yield). ESI (+) MS: m/z 288 (MH+). $^1$H NMR: 7.36 (bd, J=39.63, 2H), 7.50-7.55 (m, 1H), 7.56-7.62 (m, 2H), 7.82-7.87 (m, 2H), 7.96 (d, J=8.78, 1H), 8.24 (d, J=8.78, 1H), 8.69 (d, J=6.34, 1H), 8.77 (d, J=6.34, 1H), 9.59 (s, 1H), 13.07 (s, 1H).

By working in an analogous way and starting from the suitable carboxylic acid, respectively G5 and H2, the following compounds were prepared:

2-(4-Bromo-phenyl)-1H-pyrrolo[2,3-f]isoquinoline-3-carboxylic acid amide (G6)

ESI (+) MS: m/z 367 (MH+). $^1$H NMR: 7.53 (bs, 2H), 7.75-7.86 (m, 4H), 8.06 (d, J=8.90, 1H), 8.29 (d, J=8.78, 1H), 8.76 (d, J=6.46, 1H), 8.96 (t, J=6.22, 1H), 9.73 (s, 1H), 13.34 (bs, 1H).

2-Pyridin-4-yl-1H-pyrrolo[2,3-f]isoquinoline-3-carboxylic acid amide (H3)

ESI (+) MS: m/z 289 (MH+). $^1$H NMR: 7.80 (bd, J=74.50, 2H), 8.10 (d, J=8.90, 1H), 8.19 (d, J=5.49, 2H), 8.27 (d, J=8.78, 1H), 8.82 (d, J=6.46, 1H), 8.89 (d, J=6.34, 2H), 9.26 (d, J=6.58, 1H), 9.79 (s, 1H), 13.99 (bs, 1H).

Example 38

{(S)-3-Phenyl-2-[(2-phenyl-1H-pyrrolo[2,3-f]iso-quinoline-3-carbonyl)-amino]-propyl}-carbamic acid tert-butyl ester (G8)

To a suspension of 2-phenyl-1H-pyrrolo[2,3-f]isoquinoline-3-carboxylic acid G2 (0.087 mmol) in DMF (1 mL), DIEA (0.26 mmol) and ((S)-2-amino-3-phenyl-propyl) -carbamic acid tert-butyl ester (0.13 mmol) were added. The mixture was cooled to 0° C., EDCI hydrochloride (0.13 mmol) and HOBT (0.13 mmol) were added and stirring was kept overnight at rt. The suspension was filtered and the solid was washed with aq saturated NaHCO$_3$ and with water. After drying, the title compound was isolated in 43% yield. ESI (+) MS: m/z 521 (MH+). $^1$H NMR: 1.40 (s, 9H) 2.80-2.89 (m, 1H) 3.00-3.11 (m, 2H) 3.12-3.21 (m, 1H) 4.18-4.30 (m, 1H) 6.91-6.97 (m, 1H) 7.00-7.06 (m, 1H) 7.16-7.23 (m, 1H) 7.25-7.34 (m, 4H) 7.37-7.43 (m, 1H) 7.49-7.56 (m, 2H) 7.88 (d, J=7.62, 2H) 8.00 (d, J=9.00, 1H) 8.31 (d, J=9.00, 1H) 8.72 (s, 2H) 9.51 (s, 1H) 11.72 (bs, 1H).

Example 39

2-Phenyl-1H-pyrrolo[2,3-f]isoquinoline-3-carboxylic acid ((S)-2-amino-1-benzyl-ethyl-amide (G9)

{(S)-3-phenyl-2-[(2-phenyl-1H-pyrrolo[2,3-f]isoquinoline-3-carbonyl)-amino]-propyl}-carbamic acid tert-butyl ester G8 (0.03 mmol) was dissolved with a 1:1 mixture TFA/DCM. After 20 min stirring the solvent was removed and the residue was treated with MeOH and 1.25 M HCl in methanol for the counterion exchange. After concentration, diethylether was added and the resulting solid was filtered, washed with diethylether and dried, affording the hydrochloric salt of the title compound (95% yield). ESI (+) MS: m/z 421 (MH$^+$). $^1$H NMR: 2.82-3.15 (m, 4H), 4.53-4.66 (m, 1H), 7.26-7.40 (m, 7H), 7.66-7.71 (m, 3H), 7.89 (d, J=7.90, 1H), 7.97 (d, J=7.90, 1H), 8.10 (bs, 3H), 8.21 (d, J=8.41, 1H), 8.41 (bd, J=35.97, 1H), 8.74 (d, J=6.58, 1H), 9.01 (d, J=6.10, 1H), 9.70 (s, 1H), 13.37 (bs, 1H).

Comparison Example 40

1H-Pyrrolo[2,3-f]isoquinoline-2-carboxylic acid ethyl ester (L7)

To a solution of N-benzhydrylidene-N'-isoquinolin-5-yl-hydrazine 4A (0.12 mmol) and ethyl piruvate (0.27 mmol) in EtOH (1 mL), 3 drops of 96% sulfuric acid were added and the mixture was submitted to microwaves at 150° C. for 15 min. The solvent was removed and the residue was treated with AcOEt and 1N NaOH. The layers were separated, the aqueous layer was extracted with AcOEt and the combined organic layers were washed with water, dried (Na$_2$SO$_4$) and evaporated. The crude was purified by chromatography on silica gel (eluant: DCM/MeOH/acetone 95:2.5:2.5) providing the title compound (35% yield). ESI (+) MS: m/z 241 (MH$^+$). $^1$H NMR: 1.38 (t, J=7.03, 3H), 4.40 (q, J=7.03, 2H), 7.37 (s, 1H), 7.67 (d, J=8.79, 1H), 7.87 (d, J=8.50, 1H), 8.61 (d, J=1.17, 2H), 9.27 (s, 1H), 13.10 (bs, 1H).

Example 41

7,8-Dihydroisoquinolin-5(6H)-one, oxime (5B)

Potassium tert-butoxyde (20 mmol) was added to dry THF (20 mL) and the mixture was stirred until a clear solution was obtained. A solution of 5,6,7,8-tetrahydroisoquinoline (10 mmol) in THF (25 mL) was added rapidly and the mixture was stirred for 15 h. The reaction was then cooled in an ice bath and tert-butyl nitrite (30 mmol) was added dropwise in 30 min. The ice bath was removed and the reaction mixture was stirred for 20 h at rt. Brine was added (10 mL) and the mixture was extracted with AcOEt. The combined extracts were dried (Na$_2$SO$_4$), concentrated and the crystalline residue was triturated with toluene. Filtration gave the crude product which was recrystallized from 50% aq EtOH to give the title compound (83% yield). ESI (+) MS: m/z 164 (MH$^+$). $^1$H-NMR: 1.7-1.9 (m, 2H), 2.6-2.8 (m, 4H), 7.7 (d, 1H), 8.45 (s, 1H), 11.65 (s, 1H).

Example 42

Methyl (2E,E)-3-{[(5Z,E)-7,8-dihydroisoquinolin-5 (6H)-ylideneamino]oxy}acrylate (5C)

To a solution of 7,8-dihydroisoquinolin-5(6H)-one, oxime 5B (0.62 mmol) in dry DMSO (5 mL) containing several drops of TEA, methylpropiolate (1.23 mmol) was added. The reaction mixture was stirred at rt overnight. The resulting solution was poured into crushed ice and the aqueous layer was extracted with DCM. The organic phase was collected, washed with water, dried (Na$_2$SO$_4$) and concentrated to give a brown residue. Purification by chromatography on silica gel (eluant: cyclohexane/AcOEt 8:2) afforded the title compound (80% yield) as a mixture of (E,E) and (Z,E) isomers. ESI (+) MS: m/z 247 (MH$^+$). $^1$H-NMR: 1.86 (tt, J=5.97, 6.58, 2H), 2.81 (t, J=5.97, 2H), 2.89 (t, J=6.58, 2H), 3.63 (s, 3H, Z), 3.68 (s, 3H, E), 5.80 (d, J=12.56, 1H), 7.86 (d, J=5.24, 1H), 8.05 (d, J=12.56, 1H), 8.48 (d, J=5.24, 1H), 8.58 (s, 1H).

Example 43

Methyl 4,5-dihydro-1H-pyrrolo[2,3-f]isoquinoline-3-carboxylate (E1) and methyl 4,5-dihydro-1H-pyrrolo[2,3-f]isoquinoline-2-carboxylate (L1)

Methyl (2E,E)-3-{[(5Z,E)-7,8-dihydroisoquinolin-5(6H)-ylideneamino]oxy}acrylate 5C (1.87 mmol) was dissolved in 30 mL of toluene and the resulting solution was heated at 150° C. under stirring for 16 h pTSA (0.1 mmol) was added and the reaction mixture was maintained in the same conditions for 4 h. The solvent was evaporated, the residue dissolved with DCM and washed with diluted aq NH$_3$. The organic layer was dried (Na$_2$SO$_4$) and evaporated to yield XXI. Separation by chromatography on silica gel (eluant: DCM/MeOH 50:1) afforded E1 (0.5 mmol) and L1 (0.27 mmol). ESI (+) MS: m/z 229 (MH$^+$).

E1—$^1$H NMR: 2.88 (m, 2H), 2.94 (M, 2H), 3.72 (s, 3H), 7.40 (d, J=5.00, 1H), 7.61 (s, 1H), 8.35 (d, J=5.00, 1H), 8.35 (s, 1H), 12.96 (bs, 1H).

L1—$^1$H NMR: 2.71 (t, J=7.58, 2H), 2.86 (t, J=7.58, 2H), 3.80 (s, 3H), 6.72 (d, J=1.83, 1H), 7.77 (d, J=5.01, 1H), 8.38 (d, J=5.01, 1H), 8.39 (bs, 1H), 12.47 (s, 1H).

Example 44

4,5-Dihydro-1H-pyrrolo[2,3-f]isoquinoline-2-carboxamide (L3)

A solution of methyl 4,5-dihydro-1H-pyrrolo[2,3-f]isoquinoline-2-carboxylate L1 (0.44 mmol) in DMF (5 mL), MeOH (5 ml) and 30% aq NH$_3$ (10 mL) was heated at 80° C. in a close vessel for 8 h. The solvent was evaporated, the residue was dissolved with DCM and washed with water. The organic layer was dried (Na$_2$SO$_4$) and concentrated to provide, after trituration with diethylether, the title compound (50% yield). ESI (+) MS: m/z 214 (MH$^+$). $^1$H NMR: 2.69 (m, 2H), 2.84 (m, 2H), 6.72 (d, J=2.19, 1H), 7.08 (bs, 1H), 7.74 (d, J=5.12, 1H), 8.33-8.44 (2m, 2H), 12.01 (s, 1H).

Example 45

Methyl 1-(2,2,2-trifluoroethyl)-4,5-dihydro-1H-pyrrolo[2,3-f]isoquinoline-3-carboxylate (E3)

To a solution of methyl 4,5-dihydro-1H-pyrrolo[2,3-f]isoquinoline-3-carboxylate E1 (0.44 mmol) in dry DMF (5 mL) NaH (0.52 mmol) was added. The reaction mixture was stirred at rt for 2 h. After cooling to 0° C., trifluoroethyl triflate (0.52 mmol) in DMF (5 mL) was added dropwise. The mixture was maintained at rt overnight and then poured into icy water and extracted with DCM. The organic layer was dried (Na$_2$SO$_4$) and concentrated. Purification by chromatography on silica gel (eluant: DCM/acetone 9:1) afforded the title compound (65% yield). ESI (+) MS: m/z 311 (MH$^+$). $^1$H NMR: 2.82 (t, J=7.70, 2H), 2.92 (t, J=7.70, 2H), 3.76 (s, 3H), 5.41 (q, J=8.90, 2H), 7.56 (d, J=5.24, 1H), 7.75 (s, 1H), 8.41 (d, J=5.24, 1H), 8.44 (s, 1H).

Employing the same methodology but using the appropriate alkyl halide or triflate the following compounds were prepared:

Methyl 1-(2-amino-2-oxoethyl)-4,5-dihydro-1H-pyrrolo[2,3-f]isoquinoline-3-carboxylate (E4)

ESI (+) MS: m/z 286 (MH$^+$). $^1$H NMR: 2.80 (m, 2H), 2.92 (m, 2H), 3.73 (s, 3H), 4.94 (s, 2H), 7.17 (d, J=5.24, 1H), 7.38 (bs, 1H), 7.68 (bs, 1H), 8.36 (d, J=5.24, 1H), 8.40 (s, 1H).

Methyl 1-{3-[(tert-butoxycarbonyl)amino]propyl}-4,5-dihydro-1H-pyrrolo[2,3-f]isoquinoline-3-carboxylate (E5)

ESI (+) MS: m/z 386 (MH$^+$). $^1$H NMR: 1.83 (tt, J=6.71, 6.71, 2H), 2.81 (m, 2H), 2.85-2.95 (m, 4H), 3.72 (s, 3H), 4.31 (t, J=6.95, 2H), 6.95 (t, J=5.37, 1H), 7.39 (d, J=5.30, 1H), 7.67 (s, 1H), 8.37 (d, J=5.39, 1H), 8.40 (s, 1H).

Methyl 1-[2-(tetrahydro-2H-pyran-2-yloxy)ethyl]-4,5-dihydro-1H-pyrrolo[2,3-f]isoquinoline-3-carboxylate (E17)

ESI (+) MS: m/z 357 (MH$^+$). $^1$H NMR: 2.76-2.83 (m, 2H), 2.86-2.94 (m, 2H), 3.68-3.73 (m, 1H), 3.74 (s, 3H), 3.84-3.97 (m, 1H), 4.49-4.57 (m, 3H), 7.55 (d, J=5.24, 1H), 7.68 (s, 1H), 8.39 (d, J=5.37, 1H), 8.42 (s, 1H).

Methyl 1-(2,2,2-trifluoroethyl)-4,5-dihydro-1H-pyrrolo[2,3-f]isoquinoline-2-carboxylate (L10)

ESI (+) MS: m/z 311 (MH$^+$). $^1$H NMR: 2.67 (m, 2H), 2.83 (m, 2H), 3.74 (s, 3H), 5.49 (bs, 2H), 7.03 (s, 1H), 7.48 (d, J=5.13, 1H), 8.54 (s, 1H), 8.62 (d, J=4.95, 1H).

Example 46

1-(2,2,2-Trifluoroethyl)-4,5-dihydro-1H-pyrrolo[2,3-f]isoquinoline-3-carboxylic acid (E7)

To a solution of methyl 1-(2,2,2-trifluoroethyl)-4,5-dihydro-1H-pyrrolo[2,3-f]isoquinoline-3-carboxylate E3 (0.13 mmol) in THF/water/MeOH 8:1:1 lithium hydrate monohydrate (0.39 mmol) was added. The reaction mixture was refluxed for 8 h then the solvent was removed under reduced pressure. The residue was dissolved in water, the solution was neutralized with diluted aq potassium hydrogenosulphate and extracted with DCM/water 9:1. The organic layer was dried (Na$_2$SO$_4$) and evaporated to dryness. Trituration with diethylether provided the title compound. The aqueous layer was concentrated and the residue was cromatographed on silica gel (eluant: DCM/MeOH/30% NH$_3$ 90:9:1). The title compound was isolated in 60% overall yield. ESI (+) MS: m/z 297 (MH$^+$). MS (ES$^-$) 295. $^1$H NMR: 5.43 (q, J=8.98, 2H), 7.70 (d, J=5.73, 1H), 7.76 (s, 1H), 8.48 (d, J=5.61, 1H), 8.51 (s, 1H), 12.32 (s, 1H).

Employing the same methodology but using the corresponding esters, the following compounds were prepared:

4,5-Dihydro-1H-pyrrolo[2,3-f]isoquinoline-3-carboxylic acid (E6)

ESI (+) MS: m/z 215 (MH$^+$); MS (ES$^-$) 213. $^1$H NMR: 2.86 (m, 2H), 2.94 (m, 2H), 7.21 (bs, 1H), 7.42 (d, J=5.24, 1H), 7.52 (d, J=2.56, 1H), 8.34 (s, 1H), 8.36 (d, J=5.24, 1H), 12.96 (bs, 1H).

4,5-Dihydro-1H-pyrrolo[2,3-f]isoquinoline-2-carboxylic acid (L2)

ESI (+) MS: m/z 215 (MH$^+$); MS (ES$^-$) 213. $^1$H NMR: 2.70 (dd, J=8.00, 7.00, 2H), 2.85 (t, J=7.56, 2H), 6.65 (d, J=2.07, 1H), 7.76 (d, J=5.00, 1H), 8.37 (d, J=5.00, 1H), 8.38 (bs, 1H).

1-(2,2,2-Trifluoroethyl)-4,5-dihydro-1H-pyrrolo[2,3-f]isoquinoline-2-carboxylic acid (L4)

ESI (+) MS: m/z 299 (MH$^+$); MS (ES$^-$) 297. $^1$H NMR: 2.64 (m, 2H), 2.80 (m, 2H), 5.81 (bs, 2H), 6.96 (s, 1H), 7.69 (d, J=5.24, 1H), 8.46 (d, J=4.75, 1H), 8.49 (s, 1H), 12.84 (bs, 1H).

1-(2-Hydroxyethyl)-4,5-dihydro-1H-pyrrolo[2,3-f]isoquinoline-3-carboxylic acid (E18)

ESI (+) MS: m/z 259 (MH$^+$); MS (ES$^-$) 257. $^1$H NMR: 2.82-2.89 (m, 2H), 2.90-2.97 (m, 2H), 3.72-3.79 (m, 2H), 4.36 (t, J=5.55 Hz, 2H), 5.07 (bs, 1H), 7.64-7.70 (m, 2H), 8.46 (d, J=5.85 Hz, 1H), 8.49 (s, 1H), 12.08 (bs, 1H).

1-(Carboxymethyl)-4,5-dihydro-1H-pyrrolo[2,3-f]isoquinoline-3-carboxylic acid (E8)

ESI (+) MS: m/z 273 (MH$^+$); MS (ES$^-$) 271. $^1$H NMR: 2.82 (t, 2H, J=7.56, 2H), 2.94 (t, J=7.56, 2H), 5.18 (s, 2H), 7.19 (m, 1H), 7.62 (s, 1H), 8.42 (m, 2H).

1-{3-[(tert-Butoxycarbonyl)amino]propyl}-4,5-dihydro-1H-pyrrolo[2,3-f]isoquinoline-3-carboxylic acid (E9)

ESI (+) MS: m/z 372 (MH$^+$); MS (ES$^-$) 370. $^1$H NMR: 1.37 (s, 9H), 1.83 (qd, J=6.79, 6.58, 2H), 2.78 (t, J=7.50, 2H), 2.90 (t, J=7.50, 2H), 2.94 (q, J=6.10, 2H), 4.29 (t, J=7.01, 2H), 6.96 (t, J=5.06, 1H), 7.37 (d, J=5.24, 1H), 7.59 (s, 1H), 11.94 (bs, 1H).

Example 47

1-[2-(Tetrahydro-2H-pyran-2-yloxy)ethyl]-4,5-dihydro-1H-pyrrolo[2,3-f]isoquinoline-3-carboxylic acid (E19)

To a solution of methyl 1-[2-(tetrahydro-2H-pyran-2-yloxy)ethyl]-4,5-dihydro-1H-pyrrolo[2,3-f]isoquinoline-3-carboxylate E17 (1.4 mmol) in 30 mL of a mixture THF/MeOH/H$_2$O 8:1:1, lithium hydroxide monohydrate (2.8 mmol) was added. The resulting solution was stirred at reflux for 6 h. The solvent was removed, the residue redissolved in water and neutralized with aq KH$_2$PO$_4$. The desired product was extracted with DCM/methanol 9:1 and the organic layer was dried (Na$_2$SO$_4$) and evaporated to give, after trituration with diethylether, the title compound (63% yield). ESI (+) MS: m/z 343 (MH$^+$); MS (ES$^-$) 341. $^1$H NMR: 1.30-1.55 (m, 6H), 2.79-2.86 (m, 2H), 2.87-2.97 (m, 2H), 3.31-3.51 (m, 2H), 3.68-3.75 (m, 1H), 3.86-3.94 (m, 1H), 4.49-4.57 (m, 3H), 7.63-7.67 (m, 1H), 7.68 (s, 1H), 8.44 (d, J=5.61, 1H), 8.47 (s, 1H), 12.06 (bs, 1H).

Example 48

4,5-Dihydro-1H-pyrrolo[2,3-f]isoquinoline-3-carboxylic acid amide (E10)

A mixture of 4,5-dihydro-1H-pyrrolo[2,3-f]isoquinoline-3-carboxylic acid E6 (0.093 mmol), HOBT.NH$_3$ (0.374 mmol), TBTU (0.186 mmol) and DIEA (0.374 mmol) in DMF (5 mL) was stirred 4 h at rt. The solvent was evaporated and the crude residue was purified by preparative HPLC (Phase A: 0.05% NH$_4$OH pH10/AN 95/5, Phase B: AN; gradient phase B 0_50% 8 min, yield 30%). ESI (+) MS: m/z 214 (MH$^+$). $^1$H NMR: 2.83 (t, J=7.93, 2H), 2.98 (t, J=8.05, 2H), 6.61-7.28 (m, 2H), 7.33 (d, J=5.00, 1H), 7.56 (d, J=2.80, 1H), 8.28-8.38 (m, 2H), 11.85 (bs, 1H).

Employing the same methodology but using the appropriate carboxylic acid L2 the following compound were prepared:

4,5-Dihydro-1H-pyrrolo[2,3-f]isoquinoline-2-carboxylic acid amide (L3)

ESI (+) MS: m/z 214 (MH$^+$). $^1$H NMR: 2.69 (m, 2H), 2.84 (m, 2H), 6.72 (d, J=2.19, 1H), 7.08 (bs, 1H), 7.74 (d, J=5.12, 1H), 8.33-8.44 (2m, 2H), 12.01 (s, 1H).

Example 49

Tert-Butyl [(2S)-3-phenyl-2-({[1-(2,2,2-trifluoroethyl) -4,5-dihydro-1H-pyrrolo[2,3-f]isoquinolin-3-yl]carbonyl}amino)propyl]carbamate (E12)

To a solution of 1-(2,2,2-trifluoroethyl)-4,5-dihydro-1H-pyrrolo[2,3-f]isoquinoline-3-carboxylic acid E7 (0.34 mmol) in 20 mL of dry DMF (20 mL) N-dimethylaminopropyl-N'-ethylamine hydrochloride (0.51 mmol) and TBTU (0.51 mmol) were added. The reaction mixture was stirred at rt overnight then the solvent was removed under reduced pressure. The residue was dissolved in DCM, the organic layer was washed with saturated aq NaHCO$_3$, dried (Na$_2$SO$_4$) and concentrated. Purification by chromatography on silica gel (eluant: DCM/MeOH 98:2) provided the title compound (65% yield). ESI (+) MS: m/z 529 (MH$^+$). $^1$H NMR: 1.35 (s, 9H), 3.09 (m, 4H), 4.18 (m, 1H), 5.31 (q, J=9.15, 2H), 6.86 (t, J=5.12, 1H), 7.16 (m, 1H), 7.23-7.24 (m, 4H), 7.48 (d, J=5.24, 1H), 7.51 (bs, 1H), 7.61 (d, J=8.29, 1H), 8.39 (m, 2H).

Employing the same methodology but using the corresponding carboxylic acids the following compounds were prepared:

tert-Butyl {(2S)-2-[(4,5-dihydro-1H-pyrrolo[2,3-f]isoquinolin-3-ylcarbonyl)amino]-3-phenylpropyl}carbamate (E11)

ESI (+) MS: m/z 447 (MH$^+$). $^1$H NMR: 4.17 (m, 1H), 6.86 (t, J=5.55, 1H), 7.31 (d, J=5.00, 1H), 7.40 (d, J=8.29, 1H), 7.47 (d, J=2.80, 1H), 8.30 (s, 1H), 8.32 (d, J=5.12, 1H), 11.84 (bs, 1H).

tert-Butyl {(2S)-2-[(4,5-dihydro-1H-pyrrolo[2,3-f]isoquinolin-2-ylcarbonyl)amino]-3-phenylpropyl}carbamate (L5)

ESI (+) MS: m/z 447 (MH$^+$). $^1$H NMR: 1.36 (s, 9H), 2.68 (m, 2H), 2.83 (m, 2H), 4.20 (m, 1H), 6.89 (t, J=5.55, 1H), 7.69 (d, J=5.00, 1H), 7.82 (d, J=8.78, 1H), 8.31 (d, J=5.12, 1H), 8.33 (s, 1H), 11.97 (s, 1H).

tert-Butyl [(2S)-3-phenyl-2-({[1-(2,2,2-trifluoroethyl) -4,5-dihydro-1H-pyrrolo[2,3-f]isoquinolin-2-yl]carbonyl}amino)propyl]carbamate (L8)

ESI (+) MS: m/z 529 (MH$^+$). $^1$H NMR: 1.36 (s, 9H), 2.61 (m, 2H), 3.10 (m, 2H), 4.21 (m, 1H), 5.75 (m, 2H), 7.60 (d, J=5.37, 1H), 8.09 (d, J=8.66, 1H), 8.40 (d, J=5.24, 1H), 8.45 (s, 1H).

tert-Butyl {3-[3-({(1S)-1-benzyl-2-[(tert-butoxycarbonyl)amino]ethyl}carbamoyl)-4,5-dihydro-1H-pyrrolo[2,3-f]isoquinolin-1-yl]propyl}carbamate (E13)

ESI (+) MS: m/z 604 (MH$^+$). $^1$H NMR: 1.35 (s, 1H), 1.37 (s, 1H), 1.84 (tt, J=7.30, 7.30, 2H), 2.98 (m, 2H), 3.07 (t, J=6.34, 2H), 4.13 (m, 1H), 4.21 (t, J=7.44, 2H), 6.84 (t, J=6.34, 1H), 6.95 (t, J=5.97, 1H), 7.15 (m, 1H), 7.20-7.28 (m, 4H), 7.39 (d, J=8.54, 1H), 7.45 (s, 1H), 8.33 (d, J=5.61, 1H), 8.35.

tert-Butyl {(2S)-3-phenyl-2-[({1-[2-(tetrahydro-2H-pyran-2-yloxy)ethyl]-4,5-dihydro-1H-pyrrolo[2,3-f]isoquinolin-3-yl}carbonyl)amino]propyl}carbamate (E20)

ESI (+) MS: m/z 575 (MH$^+$). $^1$H NMR: 1.36 (s, 9H), 3.08 (t, J=5.79, 2H), 3.65-3.74 (m, 1H), 3.86-3.94 (m, 1H), 4.15 (tq, J=6.93, 1H), 6.84 (q, J=5.24, 1H), 7.43 (d, J=8.29, 1H), 7.46 (d, J=5.24, 1H), 7.50 (s, 1H), 8.34 (d, J=5.37, 1H), 8.36 (s, 1H).

Example 50

N-[(1S)-2-Amino-1-benzylethyl]-1-(2,2,2-trifluoroethyl)-4,5-dihydro-1H-pyrrolo[2,3-f]isoquinoline-3-carboxamide (E14)

To a solution of tert-butyl[(2S)-3-phenyl-2-({[1-(2,2,2-trifluoroethyl)-4,5-dihydro-1H-pyrrolo[2,3-f]isoquinolin-3-yl]carbonyl}amino)propyl]carbamate L8 (0.38 mmol) in dry dioxane (20 mL), 4M HCl in dioxane (5 mL) was added. The reaction mixture was stirred at rt overnight. The solvent was removed and the residue dissolved with DCM and washed with aq NaHCO$_3$. The organic layer was dried (Na$_2$SO$_4$) and concentrated. Purification by chromatography on silica gel (eluant: DCM/MeOH 19:1) gave, after trituration with diethylether, the title compound (75% yield). ESI (+) MS: m/z 429 (MH$^+$). $^1$H-NMR: 4.06-4.18 (m, 1H), 5.32 (q, J=8.98, 2H), 7.18 (m, 1H), 7.48 (d, J=5.24, 1H), 7.57 (s, 1H), 7.71 (d, J=8.41, 1H), 8.38 (d, J=5.24, 1H), 8.40 (s, 1H).

Employing the same methodology but using the corresponding protected amide the following compounds were prepared:

N-[(1S)-2-Amino-1-benzylethyl]-4,5-dihydro-1H-pyrrolo[2,3-f]isoquinoline-3-carboxamide (E15)

ESI (+) MS: m/z 347 (MH$^+$). $^1$H NMR: 4.36 (M, 1H), 7.15-7.30 (m, 5H), 7.97 (bs, 3H), 7.84 (m, 1H), 8.53 (s, 1H), 8.58 (d, J=6.22, 1H), 12.72 (bs, 1H).

N-[(1S)-2-Amino-1-benzylethyl]-4,5-dihydro-1H-pyrrolo[2,3-f]isoquinoline-2-carboxamide (L6)

ESI (+) MS: m/z 347 (MH$^+$). $^1$H NMR: 2.73 (d, J=4.27, 2H), 2.81 (m, 2H), 3.01 (m, 2H), 4.43 (m, 1H), 6.87 (s, 1H), 7.15-7.35 (m, 5H), 8.04 (bs, 3H), 8.20 (d, J=6.22, 1H), 8.38 (bs, 1H), 8.5-8.7 (m, 3H), 12.74 (s, 1H).

N-[(1S)-2-Amino-1-benzylethyl]-1-(2,2,2-trifluoroethyl)-4,5-dihydro-1H-pyrrolo[2,3-f]isoquinoline-2-carboxamide (L9)

ESI (+) MS: m/z 429 (MH$^+$). $^1$H NMR: 4.03 (m, 1H), 5.75 (m, 2H), 6.81 (bs, 1H), 7.1-7.3 (m, 5H), 7.60 (d, J=5.30, 1H), 8.12 (d, J=8.41, 1H), 8.40 (d, J=5.30, 1H), 8.45 (s, 1H).

N-[(1S)-2-Amino-1-benzylethyl]-1-(2-hydroxy-
ethyl)-4,5-dihydro-1H-pyrrolo[2,3-f]isoquinoline-3-
carboxamide (E21)

ESI (+) MS: m/z 391 (MH$^+$). $^1$H NMR: 3.79 (t, J=5.37, 2H), 4.37 (t, J=5.43, 2H), 5.20 (bs, 1H), 7.91 (s, 1H), 7.93 (d, J=6.46, 1H), 7.99 (bs, 1H), 8.06 (d, J=8.41, 1H), 8.55 (d, J=6.34, 1H), 8.58 (s, 1H), 14.97 (bs, 1H).

N-[(1S)-2-Amino-1-benzylethyl]-1-(3-aminopropyl)-
4,5-dihydro-1H-pyrrolo[2,3-f]isoquinoline-3-car-
boxamide (E16)

ESI (+) MS: m/z 404 (MH$^+$). $^1$H NMR: 2.08 (m, 2H), 4.46 (t, J=7.19, 2H), 7.15-7.35 (m, 5H), 7.88 (d, J=6.46, 1H), 8.00-8.20 (3 bs, 7H), 8.23 (d, J=8.41, 1H), 8.57 (d, J=6.46, 1H), 8.60 (s, 1H).

Example 51

7,8-Dihydro-6H-isoquinolin-5-one hydrochloride
(8A)

A solution of 7,8-dihydro-6H-isoquinolin-5-one oxime (50 mmol) in acetone (400 mL) and 6N HCl (160 mL) was heated to reflux for 15 h. Solvents were removed and the residue was taken up with ethanol. The solid obtained was filtered and washed with ethanol and diethylether. The title compound was recovered in 95% yield. ESI (+) MS: m/z 148 (MH$^+$). $^1$H NMR: 2.10 (q, J=12.53, 6.23, 1H), 2.70 (d, J=6.19, 1H), 2.98 (t, J=6.10, 2H), 7.75 (d, J=5.12, 1H), 8.65 (d, J=5.12, 1H), 8.78 (s, 1H).

Example 52

6-Bromo-7,8-dihydro-6H-isoquinolin-5-one
hydro-bromide (8B)

A suspension of 7,8-dihydro-6H-isoquinolin-5-one 8A (13.3 mmol) and pyridinium bromide perbromide (13.3 mmol) were suspended in glacial acetic acid (15 mL), and heated to 100° C. with microwave irradiation for 15 min. The solid formed was filtered to give the title compound as a yellow solid in 83% yield. ESI (+) MS: m/z 227 (MH$^+$). $^1$H NMR: 2.39-2.62 (m, 2H), 3.00-3.15 (m, 2H), 4.43 (dd, J=12.50, 4.94, 1H), 7.72-7.83 (m, 1H), 8.61-8.74 (m, 1H), 8.75-8.85 (m, 1H).

Example 53

Cyano-(5-oxo-5,6,7,8-tetrahydro-isoquinolin-6-yl)-
acetic acid ethyl ester (8C)

To a stirred, cold (4° C.) solution of ethyl cyanoacetate (52.2 mmol) and 6-bromo-7,8-dihydro-6H-isoquinolin-5-one 8B (6.5 mmol) in DMF (10 mL), DIEA (19.5 mmol) was added. The mixture was brought to rt and stirred for 4 h. Solvent was removed and the residue, dissolved in DCM, was repeatedly washed with water. The organic layer was dried (Na$_2$SO$_4$) and concentrated. Purification by chromatography on silica gel (DCM/MeOH 98:2) provided the title compound in 95% yield. ESI (+) MS: m/z 259 (MH$^+$). $^1$H NMR: 1.15-1.32 (m, 3H), 1.98-2.44 (m, 2H), 3.59-3.82 (m, 3H), 4.20-4.28 (m, 2H), 4.70 (s, 1H), 7.67-7.73 (m, 1H), 8.64-8.68 (m, 1H), 8.75-8.78 (m, 1H).

Example 54

2-Bromo-4,5-dihydro-1H-pyrrolo[2,3-f]isoquinoline-
3-carboxylic acid ethyl ester hydrobromide (F1)

To stirred, cold (4° C.) 33% HBr in acetic acid (27 mL), cyano-(5-oxo-5,6,7,8-tetrahydro-isoquinolin-6-yl)-acetic acid ethyl ester 8C (7 mmol), dissolved in acetic acid (22 mL) and diethyl ether (22 mL), was added dropwise. The mixture was stirred at rt for 15 h. The yellow precipitate was filtered and repeatedly washed with diethyl ether affording the title product in 89% yield. ESI (+) MS: m/z 322 (MH$^+$). $^1$H NMR: 1.32 (t, J=7.19, 3H), 3.02-3.33 (m, 4H), 4.17-4.31 (m, 2H), 7.89 (d, J=6.22, 1H), 8.61-8.64 (m, 1H), 8.65-8.70 (m, 1H), 13.49 (bs, 1H).

Example 55

2-o-Tolyl-4,5-dihydro-1H-pyrrolo[2,3-f]isoquino-
line-3-carboxylic acid ethyl ester (F3)

To a suspension of 2-bromo-4,5-dihydro-1H-pyrrolo[2,3-f]isoquinoline-3-carboxylic acid ethyl ester F1 (0.497 mmol) in toluene (4 mL) and ethanol (4 mL), o-tolylboronic acid (0.75 mmol), LiCl (1.49 mmol), Na$_2$CO$_3$.10H$_2$O (1.74 mmol) and (PPh$_3$)$_2$PdCl$_2$ (3.5 mg) were added. The mixture was heated at 150° C. for 15 min with microwave irradiation then evaporated to dryness. Chromatography on silica gel (eluant: DCM/MeOH 95:5) afforded the title compound (85% yield). ESI (+) MS: m/z 333 (MH$^+$). $^1$H NMR: 1.03 (d, J=7.07, 3H), 2.18 (s, 3H), 2.93 (t, J=7.40, 2H), 3.03 (t, J=7.30, 2H), 4.00 (q, J=7.07, 2H), 7.22-7.39 (m, 4H), 7.45 (d, J=5.12, 1H), 8.34 (d, J=5.00, 1H), 8.36 (s, 1H), 12.18 (bs, 1H). Employing the same methodology but using phenylboronic acid the following compound was prepared:

2-Phenyl-4,5-dihydro-1H-pyrrolo[2,3-f]isoquinoline-
3-carboxylic acid ethyl ester (F2)

ESI (+) MS: m/z 319 (MH$^+$). $^1$H NMR: 1.15 (t, J=7.07, 3H), 2.84-2.94 (m, 2H), 2.95-3.03 (m, 2H), 4.11 (q, J=7.07, 2H), 7.39-7.48 (m, 3H), 7.52-7.60 (m, 3H), 8.33-8.38 (m, 2H), 12.13 (bs, 1H).

Example 56

4,5-Dihydro-1H-pyrrolo[2,3-f]isoquinoline-3-car-
boxylic acid ethyl ester (E2)

A mixture of 2-bromo-4,5-dihydro-1H-pyrrolo[2,3-f]isoquinoline-3-carboxylic acid ethyl ester F1 (0.5 mmol), LiCl (1.49 mmol), Na$_2$CO$_3$.10H$_2$O (1.74 mmol) and (Ph$_3$P)$_2$PdCl$_2$ (0.005 mmol) in EtOH (4 mL) and toluene (4 mL) was heated with microwave irradiation to 150° C. for 20 min. The solvents were removed, DCM was added and the mixture washed with water. The organic layer was dried (Na$_2$SO$_4$), filtered and the solvent evaporated. The crude obtained was purified by chromatography on silica gel (DCM/MeOH 95:5). The title compound was obtained in 50% yield. ESI (+) MS: m/z 243 (MH$^+$). $^1$H NMR: 1.29 (t, J=7.07, 3H), 2.83-3.00 (m, 4H), 4.20 (q, J=7.07, 2H), 7.42 (d, J=5.00, 1H), 7.59 (d, J=3.17, 1H), 8.29-8.42 (m, 2H), 12.22 (bs, 1H).

Example 57

4,5-Dihydro-1H-pyrrolo[2,3-f]isoquinoline-3-car-
boxylic acid (E6)

To a solution of 4,5-dihydro-1H-pyrrolo[2,3-f]isoquinoline-3-carboxylic acid ethyl ester E2 (0.165 mmol) in ethanol (3 mL), 2N KOH (20 eq) was added and the mixture was heated at 60° for 4 h. After solvent removal the solution was neutralized with 1N HCl and the precipitate was filtered and dried, providing the title compound in 56% yield.

Example 58

7-Benzyl-3-ethoxycarbonyl-2-o-tolyl-4,5-dihydro-1H-pyrrolo[2,3-f]isoquinolin-7-ium; bromide (XXIIA, $R_2$=o-tolyl, $R_5$=ethyl)

A solution of 2-o-tolyl-4,5-dihydro-1H-pyrrolo[2,3-f]isoquinoline-3-carboxylic acid ethyl ester F3 (0.33 mmol) and benzyl bromide (0.27 mmol) in THF (5 mL) was heated to 120° C. with microwave irradiation for 30 min. The volatiles were removed, diethyl ether was added to the mixture and the title compound was isolated as a solid in 78% yield. ESI (+) MS: m/z 424 (MH$^+$).

Employing the same methodology but starting from bromoester F1 the following compound was prepared:

2-Bromo-4,5-dihydro-1H-pyrrolo[2,3-f]isoquinoline-3-carboxylic acid ethyl ester (XXIIB, $R_2$=bromo, $R_5$=ethyl)

ESI (+) Ms: m/z 413 (MH$^+$).

Example 59

7-Benzyl-3-ethoxycarbonyl-1-methyl-2-o-tolyl-4,5-dihydro-1H-pyrrolo[2,3-f]isoquinolin-7-ium; bromide (XXIIIA, $R_1$=methyl, $R_2$=o-tolyl, $R_5$=ethyl)

A mixture of 7-benzyl-3-ethoxycarbonyl-2-o-tolyl-4,5-dihydro-1H-pyrrolo[2,3-f]isoquinolin-7-ium; bromide XXIIA (0.32 mmol), $Cs_2CO_3$ (0.99 mmol) and methyl iodide (0.99 mmol) in THF (15 mL) was stirred to rt for 48 h. The crude title compound obtained was used as such without any further purification. ESI (+) MS: m/z 437 (MH$^+$).

Example 60

7-benzyl-2-bromo-3-ethoxycarbonyl-1-methyl-4,5-dihydro-1H-pyrrolo[2,3-f]isoquinolin-7-ium; bromide (XXIIIB, $R_1$=methyl, $R_2$=bromo, $R_5$=ethyl)

A mixture of 2-bromo-4,5-dihydro-1H-pyrrolo[2,3-f]isoquinoline-3-carboxylic acid ethyl ester XXIIB (1.6 mmol), NaH (3.2 mmol) and benzyl bromide (2.4 mmol) in THF (15 mL), was stirred at rt for 48 h. The resulting crude reaction product [9A, ESI (+) MS: m/z 413 (MH$^+$)], was used as such in the subsequent step, thus treating with NaH (1.6 mmol) and methyl iodide (1.6 mmol) with stirring for 15 h. The solvent was evaporated, the residue dissolved in DCM, washed with brine, dried ($Na_2SO_4$), filtered and concentrated, yielding crude title compound (1.64 mmol). ESI (+) MS: m/z 427 (MH$^+$).

Example 61

1-Methyl-2-o-tolyl-4,5-dihydro-1H-pyrrolo[2,3-f]isoquinoline-3-carboxylic acid ethyl ester (F4)

To a solution of 7-benzyl-3-ethoxycarbonyl-1-methyl-2-o-tolyl-4,5-dihydro-1H-pyrrolo[2,3-f]isoquinolin-7-ium; bromide XXIIIA (1.64 mmol) in dry DMSO (1 mL), 1M potassium tert-butoxide (11.5 mmol) in THF was added. The solution was bubbled with dry air overnight. Volatiles were removed, the residue was suspended in DCM, washed with water, dried ($Na_2SO_4$), filtered and the solvent evaporated. Chromatography on silica gel (eluant: DCM/MeOH 20:1) afforded the title compound. ESI (+) MS: m/z 347 (MH$^+$). $^1$H NMR: 1.1 (t, J=7.1, 3H), 2.15 (s, 3H), 2.9 (m, 2H), 3.02 (m, 2H), 4.05 (q, J=7.1, 2H), 4.2 (s, 3H), 7.2-7.4 (m, 4H), 7.48 (d, J=5.1, 1H), 8.36 (d, J=5.1, 1H), 8.4 (s, 1H).

Analogously, starting from the corresponding N-benzyl-isoquinolinium bromide (XXIIIB), the following product was obtained:

2-Bromo-1-methyl-4,5-dihydro-1H-pyrrolo[2,3-f]isoquinoline-3-carboxylic acid ethyl ester (F6)

ESI (+) MS: m/z 336 (MH$^+$). $^1$H NMR: 1.32 (t, J=7.19, 3H), 3.02-3.33 (m, 4H), 4.1 (s, 3H), 4.17-4.31 (m, 2H), 7.89 (d, J=6.22, 1H), 8.61-8.64 (m, 1H), 8.65-8.70 (m, 1H).

Example 62

7-Benzyl-3-carboxy-1-methyl-2-o-tolyl-4,5-dihydro-1H-pyrrolo[2,3-f]isoquinolin-7-ium; bromide (XXIV, $R_1$=methyl, $R_2$=o-tolyl)

To a solution of 7-benzyl-3-ethoxycarbonyl-1-methyl-2-o-tolyl-4,5-dihydro-1H-pyrrolo[2,3-f]isoquinolin-7-ium; bromide XXIIIA (0.4 mmol) in 95% EtOH (20 mL), 25% NaOH solution in water (0.6 mL) was added. The solution was heated at 60° C. for 3 h then cooled to rt and the solvent was evaporated. The residue was dissolved in 20 mL of water and the solution was acidified to pH 6 with 2N HCl. The precipitate was filtered, washed with water and dried (53% yield). ESI (+) MS: m/z 409 (MH$^+$).

Example 63

7-Benzyl-3-carbamoyl-1-methyl-2-o-tolyl-4,5-dihydro-1H-pyrrolo[2,3-f]isoquinolin-7-ium; bromide (XXV, $R_1$=methyl, $R_2$=o-tolyl, $R_5$=H)

To a solution of the 7-benzyl-3-carboxy-1-methyl-2-o-tolyl-4,5-dihydro-1H-pyrrolo[2,3-f]isoquinolin-7-ium; bromide XXIV (0.2 mmol) in dry DMF (20 mL), HOBT.NH$_3$ (0.816 mmol), TBTU (0.41 mmol) and DIEA (0.14 mL) were added. The mixture was stirred at rt for 24 h, concentrated, diluted with DCM, washed with water. The organic layers were collected, dried ($Na_2SO_4$) and evaporated to dryness. The crude obtained was used as such with no further purification. ESI (+) MS: m/z 408 (MH$^+$).

Example 64

1-Methyl-2-o-tolyl-4,5-dihydro-1H-pyrrolo[2,3-f]isoquinoline-3-carboxylic acid amide (F5)

To a solution of 7-benzyl-3-carbamoyl-1-methyl-2-o-tolyl-4,5-dihydro-1H-pyrrolo[2,3-f]isoquinolin-7-ium; bromide XXV (1.64 mmol) in dry DMSO (1 mL), 1M potassium tert-butoxide (11.5 mmol) in THF was added. The solution was bubbled with dry air overnight. Volatiles were removed, the residue was suspended in DCM, washed with water, dried ($Na_2SO_4$), filtered and the solvent evaporated. Chromatography on silica gel (eluant: DCM/MeOH 20:1) afforded the desired compound.

ESI (+) MS: m/z 318 (MH$^+$); $^1$H NMR: 2.15 (s, 3H), 2.85 (m, 2H), 3.0 (m, 2H), 4.1 (s, 3H), 6.1 (bs, 1H), 6.95 (bs, 1H), 7.1-7.3 (m, 4H), 7.5 (d, J=5.3, 1H), 8.4 (d, J=5.3, 1H), 8.6 (s, 1H).

Example 65

7-Oxo-4,5,6,7-tetrahydro-1H-indole-2,3-dicarboxylic acid 2-tert-butyl ester 3-ethyl ester (12B, R$_2$=COOtBu, R$_5$=ethyl)

To a solution of (3-ethoxy-2-oxo-cyclohex-3-enyl)-oxoacetic acid ethyl ester (20.8 mmol) in dry toluene (100 mL), tetrarhodiumdodecacarbonyl (0.32 mmol) and t-butylisocyanoacetate (25 mmol) were added. The reaction mixture was heated at 80° C. for 4 h. The solvent was evaporated and to the residue, dissolved in 30 mL of dichloromethane, 1 mL of glacial acetic acid was added. The solution was stirred at rt for 1 h then the organic solvents were evaporated to dryness. Chromatography on silica gel (eluant: hexane/AcOEt 8:2) provided the title compound in 24% yield. ESI (+) MS: m/z 308 (MH$^+$).

Employing the same methodology but using the suitable isocyanate, the following compound were obtained:

7-Oxo-4,5,6,7-tetrahydro-1H-indole-2,3-dicarboxylic acid diethyl ester (12D, R$_2$=COOEt, R$_5$=ethyl)

ESI (+) MS: m/z 280 (MH$^+$).

Example 66

1-Methyl-7-oxo-4,5,6,7-tetrahydro-1H-indole-2,3-dicarboxylic acid 2-tert-butyl ester 3-ethyl ester (XXVIA, R$_1$=methyl, R$_2$=COOtBu, R$_5$=ethyl)

To a solution of 7-oxo-4,5,6,7-tetrahydro-1H-indole-2,3-dicarboxylic acid 2-tert-butyl ester 3-ethyl ester 12B (0.72 mmol) in dry DMF (10 mL), caesium carbonate (1.44 mmol) and methyl iodide (2.16 mmol) were added. The reaction mixture was heated at 60° C. in a sealed tube for 1 h then the solvent was evaporated. The residue was dissolved in DCM, washed with water, dried (Na$_2$SO$_4$) and concentrated, affording the title compound in quantitative yield. ESI (+) MS: m/z 322 (MH$^+$).

Employing the same methodology on 12D, the following compound was obtained:

1-Methyl-7-oxo-4,5,6,7-tetrahydro-1H-indole-2,3-dicarboxylic acid diethyl ester (XXVIB, R$_1$=methyl, R$_2$=COOEt, R$_5$=ethyl)

ESI (+) MS: m/z 294 (MH$^+$).

Example 67

8-Amino-1-methyl-4,5-dihydro-1H-1,7,9-triaza-cyclopenta[a]naphthalene-2,3-dicarboxylic acid 2-tert-butyl ester 3-ethyl ester (N6)

To a solution of 1-methyl-7-oxo-4,5,6,7-tetrahydro-1H-indole-2,3-dicarboxylic acid 2-tert-butyl ester 3-ethyl ester XXVIA (4.67 mmol) in DMF (20 mL), N,N-dimethylformamide di-tert-butyl acetal (2 mL) was added and the solution was stirred at 100° C. overnight. After cooling to rt guanidine hydrochloride (14 mmol) and K$_2$CO$_3$ (14 mmol) were added and the mixture was heated at 100° C. for 24 h. The organic solvent was evaporated to dryness. Chromatography on silica gel (AcOEt/hexane 1:1) afforded the title compound (80% yield). ESI (+) MS: m/z 373 (MH$^+$). $^1$H NMR: 1.28 (t, J=7.07, 3H), 1.55 (s, 9H), 2.68 (t, J=7.80, 2H), 2.79 (t, J=7.80, 2H), 4.18 (s, 3H), 4.23 (q, J=7.07, 2H), 6.40 (bs, 2H), 7.97 (s, 1H).

Employing the same methodology on XXVIB, the following compound was obtained:

8-Amino-1-methyl-4,5-dihydro-1H-1,7,9-triaza-cyclopenta[a]naphthalene-2,3-dicarboxylic acid diethyl ester (N5)

ESI (+) MS: m/z 345 (MH$^+$). $^1$H NMR: 1.26 (t, J=7.07, 3H), 1.30 (t, J=7.07, 3H), 2.69 (t, J=7.80, 2H), 2.80 (t, J=7.80, 2H), 4.20 (s, 3H), 4.21 (q, J=7.07, 2H), 4.32 (q, J=7.07, 2H), 6.42 (bs, 2H), 8.08 (s, 1H).

Example 68

8-Amino-1-methyl-4,5-dihydro-1H-1,7,9-triaza-cyclopenta[a]naphthalene-2,3-dicarboxylic acid 3-ethyl ester (N7)

To a solution of 8-amino-1-methyl-4,5-dihydro-1H-1,7,9-triaza-cyclopenta[a]naphthalene-2,3-dicarboxylic acid 2-tert-butyl ester 3-ethyl ester N6 (3.76 mmol) in 20 mL of EtOH, 2N HCl (2 mL) was added. The solution was stirred at reflux for 5 h then the solvent was evaporated, affording the title compound in quantitative yield. ESI (+) MS: m/z 317 (MH$^+$), MS (ES$^-$) 315. $^1$H NMR: 1.27 (t, J=7.08, 3H), 2.79 (t, J=7.68, 2H), 2.93 (t, J=7.68, 2H), 4.15 (s, 3H), 4.23 (q, J=7.08, 2H), 7.96 (bs, 1H), 8.11 (s, 1H), 8.38 (bs, 1H).

Example 69

8-Amino-2-iodo-1-methyl-4,5-dihydro-1H-1,7,9-triaza-cyclopenta[a]naphthalene-3-carboxylic acid ethyl ester (N1)

To a solution of 8-amino-1-methyl-4,5-dihydro-1H-1,7,9-triaza-cyclopenta[a]naphthalene-2,3-dicarboxylic acid 3-ethyl ester N7 (3.16 mmol) in a mixture of DCM (10 mL) and water (10 mL), under vigorous stirring at 50° C., NaHCO$_3$ (9.48 mmol) and an aqueous solution (4 mL) of iodine (4.1 mmol) and potassium iodide (7.58 mmol) was added. The mixture was heated at 50° C. for 3 h, cooled to rt and the organic layer was separated and washed with aq NaHSO$_3$. The organic phase was dried (Na$_2$SO$_4$) and evaporated to dryness. Chromatography on silica gel (eluant: AcOEt/hexane 7:3) afforded the title compound (30% yield). ESI (+) MS: m/z 399 (MH$^+$). $^1$H NMR: 1.32 (t, J=7.07, 3H), 2.65 (t, J=7.68, 2H), 2.91 (t, J=7.68, 2H), 4.21 (s, 3H), 4.24 (q, J=7.07, 2H), 6.34 (bs, 2H), 8.02 (s, 1H).

Example 70

8-Amino-1-methyl-4,5-dihydro-1H-1,7,9-triaza-cyclopenta[a]naphthalene-3-carboxylic acid ethyl ester (M1)

To a solution of 8-amino-2-iodo-1-methyl-4,5-dihydro-1H-1,7,9-triaza-cyclopenta[a]naphthalene-3-carboxylic acid ethyl ester N1 (0.62 mmol) in DMF (5 mL) and under argon, HCOONa (1.4 mmol) and Pd(Ph3P)$_4$ (0.04 mmol) were added and the mixture was heated at 100° C. for 4 h. The mixture was cooled to rt, diluted with dichloromethane and washed with water. The organic phase was dried (Na$_2$SO$_4$)

Example 71

8-Amino-1-methyl-4,5-dihydro-1H-1,7,9-triaza-cyclopenta[a]naphthalene-3-carboxylic acid (M2)

To a solution of 8-amino-1-methyl-4,5-dihydro-1H-1,7,9-triaza-cyclopenta[a]naphthalene-3-carboxylic acid ethyl ester M1 (0.51 mmol) in 95% EtOH (10 mL), KOH (1.54 mmol) was added. The mixture was heated to reflux for 10 h then cooled and evaporated to dryness. The residue was dissolved in 30 mL of water, acidified with glacial AcOH and the precipitate was filtered and washed with water. The product was dried affording the title compound (75% yield). ESI (+) MS: m/z 245 (MH$^+$). $^1$H NMR: 2.65 (t, J=7.80, 2H), 2.92 (t, J=7.80, 2H), 4.15 (s, 3H), 6.39 (bs, 2H), 7.78 (s, 1H), 8.01 (s, 1H), 12.30 (bs, 1H).

Example 72

8-Amino-1-methyl-4,5-dihydro-1H-1,7,9-triaza-cyclopenta[a]naphthalene-3-carboxylic acid amide (M3)

To a solution of 8-amino-1-methyl-4,5-dihydro-1H-1,7,9-triaza-cyclopenta[a]naphthalene-3-carboxylic acid M2 (0.08 mmol) in dry DMF (4 mL), HOBT.NH$_3$ (0.164 mmol), TBTU (0.164 mmol) and DIEA (0.328 mmol) were added. The mixture was stirred at rt for 24 h then the solvent was evaporated. The residue was suspended in 10 mL of water, filtered, washed with water and dried in vacuo, providing the title compound (55% yield). ESI (+) MS: m/z 244 (MH$^+$). $^1$H NMR: 2.73 (t, J=7.44, 2H), 3.00 (t, J=7.44, 2H), 4.04 (s, 3H), 6.94 (bs, 1H), 7.35 (bs, 1H), 7.73 (s, 1H), 7.96 (s, 1H), 7.76 (bs, 3H).

Example 73

8-Amino-2-iodo-1-methyl-4,5-dihydro-1H-1,7,9-triaza-cyclopenta[a]naphthalene-3-carboxylic acid (N2)

To a solution of 8-amino-2-iodo-1-methyl-4,5-dihydro-1H-1,7,9-triaza-cyclopenta[a]naphthalene-3-carboxylic acid ethyl ester N1 (1.28 mmol) in 95% EtOH (30 mL) 4M NaOH (1.2 mL) was added. The mixture was heated to reflux for 10 h then cooled and evaporated to dryness. The residue was dissolved in 30 mL of water, acidified with glacial AcOH and the precipitate was filtered and washed with water. The product was dried affording the title compound (95% yield). ESI (+) MS: m/z 371 (MH$^+$). $^1$H NMR: 2.63 (t, J=7.80, 2H), 2.90 (t, J=7.80, 2H), 4.18 (s, 3H), 6.33 (bs, 2H), 8.00 (s, 1H), 12.26 (bs, 1H).

Example 74

8-Amino-2-iodo-1-methyl-4,5-dihydro-1H-1,7,9-triaza-cyclopenta[a]naphthalene-3-carboxylic acid amide (N3)

To a solution of 8-amino-2-iodo-1-methyl-4,5-dihydro-1H-1,7,9-triaza-cyclopenta[a]naphthalene-3-carboxylic acid N2 (0.6 mmol) in dry DMF (10 mL), HOBT.NH$_3$ (1.19 mmol), TBTU (1.19 mmol) and DIEA (0.4 mL) were added. The mixture was stirred at rt for 24 h then the solvent was evaporated. The residue was suspended in 20 mL of water, filtered and washed with water and then dried providing the title compound (60% yield). ESI (+) MS: m/z 370 (MH$^+$). $^1$H NMR: 2.62 (t, J=7.60, 2H), 2.75 (t, J=7.60, 2H), 4.13 (s, 3H), 6.28 (bs, 2H), 7.07 (bs, 1H), 7.18 (bs, 1H), 7.98 (s, 1H).

Example 75

8-Amino-1-methyl-2-phenyl-4,5-dihydro-1H-1,7,9-triaza-cyclopenta[a]naphthalene-3-carboxylic acid amide (N4)

To a suspension of 8-amino-2-iodo-1-methyl-4,5-dihydro-1H-1,7,9-triaza-cyclopenta[a]naphthalene-3-carboxylic acid amide N3 (0.34 mmol) in 15 mL of DMF under argon, phenylboronic acid (0.5 mmol), LiCl (1 mmol), Na$_2$CO$_3$ (0.85 mmol), water (1 mL) and (PPh$_3$)$_2$PdCl$_2$ (7 mg) were added. The mixture was heated at 100° C. for 10 h then evaporated to dryness. Chromatography on silica gel (eluant: DCM/MeOH 20:1) afforded the title compound (74% yield). ESI (+) MS: m/z 320 (MH$^+$). $^1$H NMR: 2.68 (t, J=7.80, 2H), 2.84 (t, J=7.80, 2H), 3.86 (s, 3H), 6.21 (bs, 2H), 6.27 (bs, 1H), 6.91 (bs, 1H), 7.41-7.54 (m, 5H), 7.99 (s, 1H).

Example 76

8-Amino-1-methyl-2-phenyl-1H-1,7,9-triaza-cyclopenta[a]naphthalene-3-carboxylic acid amide (N10)

A suspension of 8-amino-1-methyl-2-phenyl-4,5-dihydro-1H-1,7,9-triaza-cyclopenta[a]naphthalene-3-carboxylic acid amide N4 (0.25 mmol) and 10% Pd on carbon (50 mg) in 10 mL of xilene was heated to reflux for 15 days. The mixture was filtered through a celite pad and the solvent evaporated to dryness affording the title compound (85% yield). ESI (+) MS: m/z 318 (MH$^+$). $^1$H NMR: 4.21 (s, 3H), 6.15 (bs, 1H), 6.76 (bs, 2H), 7.08 (bs, 1H), 7.42 (d, J=8.50, 1H), 7.52-7.65 (m, 5H), 7.83 (d, J=8.50, 1H), 9.03 (s, 1H).

Example 77

8-Amino-2-phenyl-1H-1,7,9-triaza-cyclopenta[a]naphthalene-3-carboxylic acid ethyl ester (N8)

To a solution of 5-(2-amino-5-bromo-pyrimidin-4-yl)-4-iodo-2-phenyl-1H-pyrrole-3-carboxylic acid ethyl ester (XXVIIA, R$_2$=phenyl, R$_3$=COOEt, 0.099 mmol) in dioxane (4 mL), under argon, vinyltributyltin (0.099 mmol), 2,6-di-tert-butyl-4-methylphenol (0.0045 mmol) and Pd(Ph$_3$P)$_4$ (0.01 mmol) were added. The reaction mixture was heated at 110° C. for 3 h, cooled to rt, the precipitate filtered through a celite pad and the resulting solution evaporated to dryness. The residue was chromatographed on silica gel (eluant: AcOEt/hexane 4:1) affording the title compound (0.03 mmol, 30% yield), ESI (+) MS: m/z 333 (MH$^+$). $^1$H NMR: 1.20 (t, J=7.03, 3H), 4.19 (q, J=7.03, 2H), 6.55 (bs, 2H), 7.50 (d, J=8.60, 1H), 7.53-7.70 (m., 5H), 7.90 (d, J=8.60, 1H), 9.07 (s, 1H), 12.93 (s, 1H), and 5-amino-8-methylene-2-phenyl-3,8-dihydro-3,4,6-triaza-cyclopenta[a]indene-1-carboxylic acid ethyl ester (0.024 mmol) (XXVIII, R$_2$=phenyl, R$_3$=COOEt), ESI (+) MS: m/z 333 (MH$^+$). $^1$H NMR: 1.14 (t, J=7.07 Hz, 3H), 4.16 (q, J=7.07 Hz, 2H), 6.02 (d, J=1.32, 1H), 6.43 (d, J=1.32, 1H), 6.57 (bs, 2H), 7.40-7.46 (m, 2H), 7.52-7.66 (m, 3H), 8.44 (s, 1H), 12.74 (s, 1H).

Employing the same methodology but starting from 5-(2-amino-5-bromo -pyrimidin-4-yl)-4-iodo-2-phenyl-1H-pyrrole-3-carboxylic acid amide (XXVIIB, $R_2$=phenyl, $R_3$=$CONH_2$), the following compounds were obtained:

8-Amino-2-phenyl-1H-1,7,9-triaza-cyclopenta[a]naphthalene-3-carboxylic acid amide (N9)

ESI (+) MS: m/z 304 (MH$^+$). $^1$H NMR: 6.50 (bs, 2H), 7.20 (bs, 2H), 7.40-7.52 (m, 5H), 7.47 (d, J=8.50, 1H), 7.62 (d, J=8.50, 1H), 9.04 (s, 1H), 11.40 (s, 1H), and 5-Amino-8-methylene-2-phenyl-3,8-dihydro-3,4,6-triaza -cyclopenta[a]indene-1-carboxylic acid amide (XXVIII, $R_2$=phenyl, $R_3$=$CONH_2$)

ESI (+) MS: m/z 304 (MH$^+$). $^1$H NMR: 5.87 (s, 1H), 5.97 (s, 1H), 6.53 (bs, 2H), 7.25 (bs, 2H), 7.35 (t, J=7.35, 1H), 7.43 (bt, J=7.35, 2H), 7.65 (bd, J=7.35, 2H), 8.38 (s, 1H), 12.38 (s, 1H).

Example 78

8-Amino-1-methyl-2-phenyl-1H-1,7,9-triaza-cyclopenta[a]naphthalene-3-carboxylic acid amide (N10)

To a solution of 8-amino-2-phenyl-1H-1,7,9-triaza-cyclopenta[a]naphthalene-3-carboxylic acid amide N9 (0.16 mmol) in dry DMF (5 mL), caesium carbonate (0.7 mmol) and methyl iodide (0.7 mmol) were added. The reaction mixture was heated at 70° C. in a sealed tube for 1 h then the solvent was evaporated. The solid residue was washed with water and dried, giving the title compound (78% yield). ESI (+) MS: m/z 391 (MH$^+$). $^1$H NMR: 4.21 (s, 3H), 6.15 (bs, 1H), 6.76 (bs, 2H), 7.08 (bs, 1H), 7.42 (d, J=8.50, 1H), 7.52-7.65 (m, 5H), 7.83 (d, J=8.50, 1H), 9.03 (s, 1H).

The invention claimed is:
1. A compound of the formula (I):

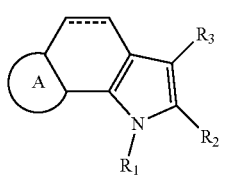

(I)

wherein the ring A represents a fused heterocycle of the formula IIa, IIb, III or IV:

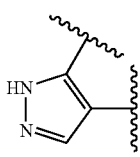

(IIa)

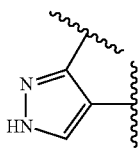

(IIb)

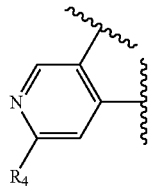

(III)

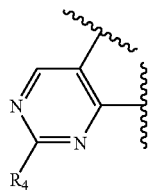

(IV)

$R_1$ represents hydrogen atom or an optionally substituted group selected from alkyl, cycloalkyl, alkenyl, alkynyl, heterocyclyl, aryl, heterocyclyloxy-alkyl and alkoxycarbonyl group;

$R_2$ is hydrogen or halogen atom or a group of formula —$COOR_5$ or —$CONHR_5$, wherein $R_5$ represents one of the meanings above defined for $R_1$, or an optionally substituted aryl or heterocyclyl group;

$R_3$ is hydrogen atom or a group of formula —CHO, —$COOR_5$ or —$CONHR_5$, wherein $R_5$ is as defined above;

$R_4$ is hydrogen atom or $NHR_6$, wherein $R_6$ is hydrogen atom or an optionally substituted alkyl, aryl or heterocyclyl group;

----- means either single or double Carbon-Carbon bond (—$CH_2$—$CH_2$— or —CH=CH—);

or a pharmaceutically acceptable salt thereof; with the provisos that if $R_2$ is hydrogen or halogen atom or an optionally substituted aryl or heterocyclyl group, then $R_3$ is not hydrogen atom, and if the ring A is a fused heterocycle of the formula III, $R_3$ and $R_4$ are hydrogen atoms, and ----- means double Carbon-Carbon bond (—CH=CH—), then $R_2$ is not COOH, COO-Alkyl, the compound 1H-pyrrolo[2,3-f]isoquinoline-3-carboxaldehyde is excluded.

2. A compound of formula (I) as defined in claim 1 wherein $R_2$ represents hydrogen or halogen atom or an optionally substituted aryl or heterocyclyl group or a —C(O)NHR$_5$ group and $R_3$ represents hydrogen atom or a —CONHR$_5$ group, wherein $R_5$ is as defined in claim 1.

3. A compound of formula (I) as defined in claim 1 wherein $R_1$ represents hydrogen atom or an optionally substituted alkyl; $R_2$ represents hydrogen atom or an optionally substituted aryl or heterocyclyl group or a —CONHR$_5$ group, wherein $R_5$ represents (S)-3-phenyl-propane-1-amino-2-yl group; $R_3$ represents hydrogen atom or a —CONHR$_5$ group, wherein $R_5$ represents hydrogen atom or (S)-3-phenyl-propane-1-amino-2-yl group; $R_4$ represents hydrogen atom or $NH_2$.

4. A compound of formula (I) as defined in claim 1 or a pharmaceutically acceptable salt thereof, which is selected from the group consisting of:
1-methyl-1,6-dihydro-1,6,7-triaza-as-indacene-3-carboxylic acid;
1-methyl-1,7-dihydro-1,6,7-triaza-as-indacene-3-carboxylic acid amide;

2-chloro-1-methyl-1,6-dihydro-1,6,7-triaza-as-indacene-3-carboxylic acid amide;
1-methyl-2-phenyl-1,7-dihydro-1,6,7-triaza-as-indacene-3-carboxylic acid amide;
4,5-dihydro-1H-pyrrolo[2,3-f]isoquinoline-3-carboxylic acid;
1-(2,2,2-trifluoroethyl)-4,5-dihydro-1H-pyrrolo[2,3-f] isoquinoline-3-carboxylic acid;
4,5-dihydro-1H-pyrrolo[2,3-f]isoquinoline-3-carboxylic acid amide; tert-butyl {(2S)-2-[(4,5-dihydro-1H-pyrrolo[2,3-f]isoquinolin-3-ylcarbonyl)amino]-3-phenylpropyl}carbamate;
tent-butyl [(2S)-3-phenyl-2-({[1-(2,2,2-trifluoroethyl) - 4,5-dihydro-1H-pyrrolo[2,3-*f*]isoquinolin-3-yl] carbonyl}amino)propyl]carbamate;
N-[(1S)-2-amino-1-benzylethyl]-1-(2,2,2-trifluoroethyl) - 4,5-dihydro-1H-pyrrolo[2,3-*f*]isoquinoline-3-carboxamide;
N-[(1S)-2-amino-1-benzylethyl]-4,5-dihydro-1H-pyrrolo[2,3-f]isoquinoline-3-carboxamide;
N-[(1S)-2-amino-1-benzylethyl]-1-(2-hydroxyethyl)-4,5-dihydro-1H-pyrrolo[2,3-f]isoquinoline-3-carboxamide;
2-bromo-4,5-dihydro-1H-pyrrolo[2,3-f]isoquinoline-3-carboxylic acid ethyl ester;
1-methyl-2-o-tolyl-4,5-dihydro-1H-pyrrolo[2,3-f]isoquinoline-3-carboxylic acid amide;
2-phenyl-1H-pyrrolo[2,3-f]isoquinoline-3-carboxylic acid amide;
2-(4-bromo-phenyl)-1H-pyrrolo[2,3-f]isoquinoline-3-carboxylic acid;
2-(4-bromo-phenyl)-1H-pyrrolo[2,3-f]isoquinoline-3-carboxylic acid amide;
2-(4-morpholin-4-yl-phenyl)-1H-pyrrolo[2,3-f]isoquinoline-3-carbaldehyde;
2-phenyl-1H-pyrrolo[2,3-f]isoquinoline-3-carboxylic acid ((S)-2-amino-1-benzyl-ethyl) amide;
2-pyridin-4-yl-1H-pyrrolo[2,3-f]isoquinoline-3-carbaldehyde;
2-pyridin-4-yl-1H-pyrrolo[2,3-f]isoquinoline-3-carboxylic acid amide;
4,5-dihydro-1H-pyrrolo[2,3-f]isoquinoline-2-carboxylic acid;
N-[(1S)-2-amino-1-benzylethyl]-4,5-dihydro-1H-pyrrolo[2,3-7]isoquinoline-2-carboxamide;
N-[(1S)-2-amino-1-benzylethyl]-1-(2,2,2-trifluoroethyl)-4,5-dihydro-1H-pyrrolo[2,3-f]isoquinoline-2-carboxamide;
8-amino-1-methyl-2-phenyl-4,5-dihydro-1H-1,7,9-triaza-cyclopenta[a]naphthalene-3-carboxylic acid amide;
8-amino-2-phenyl-1H-1,7,9-triaza-cyclopenta[a]naphthalene-3-carboxylic acid amide; and
8-amino-1-methyl-2-phenyl-1H-1,7,9-triaza-cyclopenta[a]naphthalene-3-carboxylic acid amide.

5. A method for treating a cell proliferative disorder selected from the group consisting of gliosarcoma, ovary cancer, breast cancer and colorectal cancer comprising:
administering to a mammal in need thereof an effective amount of a compound of formula (I) as defined in claim 1.

6. The method according to claim 5 wherein the cell proliferative disorder is caused by an altered Cdc7 or AKT kinase.

7. The method according to claim 5 further comprising subjecting the mammal in need thereof to a radiation therapy or chemotherapy regimen in combination with at least one cytostatic or cytotoxic agent.

8. The method according to claim 5 wherein the mammal in need thereof is a human.

9. A method for inhibiting Cdc7 or AKT kinase activity which comprises contacting the said kinase with an effective amount of a compound as defined in claim 1.

10. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

11. A product or kit comprising a compound of formula (I) or a pharmaceutically acceptable salt thereof, as defined in claim 1, or pharmaceutical compositions thereof comprising a therapeutically effective amount of said compound of formula (I) or a pharmaceutically acceptable salt thereof, and at least one pharmaceutically acceptable excipient, carrier and/or diluent, and one or more chemotherapeutic agents, as a combined preparation for simultaneous, separate or sequential use.

12. A compound of formula (I) or a pharmaceutically acceptable salt thereof, as defined in claim 1, for use as a medicament for treating a cell proliferative selected from the group consisting of gliosarcoma, ovary cancer, breast cancer, and colorectal cancer.

13. A compound of formula (I) or a pharmaceutically acceptable salt thereof, as defined in claim 1, for use as a medicament for treating a cell proliferative disorder caused by an altered Cdc7 or AKT kinase, wherein the cell proliferative disorder is selected from the group consisting of gliosarcoma, ovary cancer, breast cancer, and colorectal cancer.

* * * * *